US009913836B2

(12) United States Patent
Clarence-Smith et al.

(10) Patent No.: US 9,913,836 B2
(45) Date of Patent: *Mar. 13, 2018

(54) ANTICHOLINERGIC NEUROPROTECTIVE COMPOSITION AND METHODS

(71) Applicant: Chase Pharmaceuticals Corporation, Washington, DC (US)

(72) Inventors: Kathleen E. Clarence-Smith, Washington, DC (US); Thomas N. Chase, Washington, DC (US)

(73) Assignee: Chase Pharmaceuticals Corporation, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/377,344

(22) Filed: Dec. 13, 2016

(65) Prior Publication Data
US 2017/0087142 A1 Mar. 30, 2017

Related U.S. Application Data

(63) Continuation of application No. 14/426,022, filed as application No. PCT/US2013/058172 on Sep. 5, 2013, now Pat. No. 9,561,218.

(60) Provisional application No. 61/697,069, filed on Sep. 5, 2012, provisional application No. 61/697,039, filed on Sep. 5, 2012, provisional application No. 61/697,021, filed on Sep. 5, 2012, provisional application No. 61/696,978, filed on Sep. 5, 2012.

(51) Int. Cl.
A61K 31/46 (2006.01)
A61K 31/4465 (2006.01)
A61K 31/40 (2006.01)
A61K 31/4178 (2006.01)
A61K 31/439 (2006.01)
A61K 31/166 (2006.01)
A61K 31/325 (2006.01)
A61K 31/454 (2006.01)

(52) U.S. Cl.
CPC ............ A61K 31/46 (2013.01); A61K 31/166 (2013.01); A61K 31/325 (2013.01); A61K 31/40 (2013.01); A61K 31/4178 (2013.01); A61K 31/439 (2013.01); A61K 31/4465 (2013.01); A61K 31/454 (2013.01)

(58) Field of Classification Search
CPC .. A61K 2300/00; A61K 31/445; A61K 31/55; A61K 31/27; A61K 31/4747; A61K 31/454; A61K 45/06; A61K 31/439; A61K 31/4709; A61K 31/166; A61K 31/325; A61K 31/46; A61K 31/473; A61K 31/197; A61K 31/40; A61K 31/4178; A61K 9/206
See application file for complete search history.

(56) References Cited

U.S. PATENT DOCUMENTS

| 5,854,270 | A | 12/1998 | Gambhir |
| 6,906,081 | B2 | 6/2005 | Hey et al. |
| 8,404,701 | B2 | 3/2013 | Chase et al. |
| 2003/0036549 | A1 | 2/2003 | Mangel et al. |
| 2005/0010259 | A1 | 1/2005 | Gerber |
| 2005/0065176 | A1 | 3/2005 | Field et al. |
| 2005/0222165 | A1 | 10/2005 | Wyllie |
| 2006/0293356 | A1 | 12/2006 | Aberg |
| 2007/0053982 | A1 | 3/2007 | Ogorka et al. |
| 2007/0093519 | A1* | 4/2007 | Sandage, Jr. ........ A61K 31/192 514/290 |
| 2007/0249869 | A1 | 10/2007 | Sellstedt et al. |
| 2008/0114014 | A1 | 5/2008 | Rich |
| 2009/0062372 | A1 | 3/2009 | Baxter |
| 2011/0021503 | A1 | 1/2011 | Chase et al. |
| 2011/0071135 | A1 | 3/2011 | Chase et al. |
| 2011/0201597 | A1 | 8/2011 | Chase et al. |

FOREIGN PATENT DOCUMENTS

| EP | 0236684 | 2/1987 |
| EP | 0976404 | 2/2000 |
| JP | 62215527 | 9/1967 |
| JP | 2000143541 | 5/2000 |
| JP | 2007517905 | 7/2007 |
| JP | 2011518776 | 6/2011 |

(Continued)

OTHER PUBLICATIONS

Glenmark Generics (Trospium Chloride, https://dailymed.nlm.nih.gov/dailymed/archives/fdaDrugInfo.cfm?archiveid=50850, Feb. 2011, publication date indicated on the product data sheet).*
DailyMed (Glycopyrrolate tablets information, Updated on Dec. 1, 2011, US National Library of Medicine, https://dailymed.nlm.nih.gov/dailymed/drugInfo.cfm?setid=bd65ee5e-2000-423c-b0a6-72eb213455c4).*
Jappinen et al (Pharmacy World and Science, 1999, vol. 21, pp. 272-274).*
Chapple et al., "Solifenacin significantly improves all symptoms of overactive bladder syndrome", Int. J. Clin. Pract., 60(8):959-966 (2006).
Communication for European Patent 13836121.7 dated Mar. 15, 2016, with Supplementary European Search Report (dated Mar. 7, 2016).

(Continued)

Primary Examiner — Mark V Stevens
(74) Attorney, Agent, or Firm — Sughrue Mion, PLLC

(57) ABSTRACT

The present invention relates to a pharmaceutical composition comprising propiverine, trospium or glycopyrrolate; and a non-anticholinergic antiemetic agent. It is also related to a pharmaceutical composition comprising a high dose of solifenacin or a pharmaceutically acceptable salts thereof; and a non-anticholinergic antiemetic agent. Pharmaceutical compositions containing high dose of nsPAChA for use for increasing the AChEI blood concentrations and for combating neurodegeneration are also described. The invention also relates to a method for inducing neuroprotection and combating neurodegeneration in a patient suffering from Alzheimer type dementia as well as to a method for increasing the blood levels of an acetyl choline esterase inhibitor (AChEI) in a human subject treated with an AChEI dose.

11 Claims, No Drawings

(56) References Cited

FOREIGN PATENT DOCUMENTS

| WO | 2004069246 | 8/2004 |
|----|------------|--------|
| WO | 2005073198 | 8/2005 |
| WO | 200803329  | 3/2008 |
| WO | 2009120277 | 10/2009 |

OTHER PUBLICATIONS

Doody et al., "Safety and Tolerability of Donepezil at Doses up to 20 mg/day", Drugs & Aging, 25(2):163-174 (2008).
Examination Report for PCT/US2009/001662 dated Oct. 15, 2015.
Forette et al., "A phase II study in patients iwht Alzheimer's disease to assess the preliminary efficacy and maximum tolerated dose of rivastigmine (Exelon)", European Journal of Neurology, 6:423-429 (1999).
Hikasa et al., "Antagonism of the emetic action of xylazine by alpha-adrenoceptor blocking agents", European Journal of Pharmacology, 130:229-235 (1986).
Honma et al, "Current status and prospects of therapeutic agents for Alzheimer—from mechanisms thereof", Japanese Journal of Geriatric Psychiatry, 17(1):23-32 (2006).
Isik et al., "Trospium and Cognition in Patients with Late Onset Alzheimer Disease", The Journal of Nutrition, Health & Aging, 13(8):672-676 (2009).
Jhee et al., Letter to the Editor, "Centrally acting antiemetics mitigate nausea and vomiting in patients with alzheimer's disease who receive rivastigmine", Clinical Neuropharmacology, 25(2):122-123 (2002).
Kobayashi, "Treatment of dementia in United States, Guidelines for case and problems", Japanese Journal of Geriatric Psychiatry, 20(4):399-406 (2009).
Lockhart et al., "Safety and Tolerability of Donepezil, Rivastiglmne and Galantamine for Patients with Alzheimer's Disease: Systematic Review of the 'Real-World' Evidence", Dementia and Geriatric Cognitive Disorders, 28:389-403 (2009).
Notification of Reasons for Rejection for Japanese Patent Application No. 2012-529733 dated Apr. 12, 2016.
Scarzella, "Domperidone is effective in teh prevention of rivastigmine-related gastrointestinal disturbances", Functional Neurology, 22(2):101-104 (2007).
Zhang et al., "Peripheral cholinoceptor antagonist anisodamine counteracts cholinergic adverse effects and facilitates cognitive amelioration of rivastigmine", J. Neural. Transm., 116(12):1643-1649 (2009).
Wilcock et al., "Efficacy and safety of galantamine in patients with mild to moderate Alzheimer's disease: multicentre fandomised controlled trial", doi:http//dx.doi.org/10.1136/bjm.322.7274.1445 BJM, 321:1145 (2000).
Cappon et al., "Tolterodine does not affect memory assessed by passive-avoidance response test in mice", European Journal of Pharmacology, 579:225-228 (2008).
Jann et al., "Clinical Pharmacokinetics and Pharmacodynamics of Cholinestrase Inhibitors", Clinical Pharmacokinet., 41(10):719-739 (2002).
Takeda et al., "Effects of Anti-Cholinergics on Cognitive Functions, Urinary Symptoms, Urinary Functions, and Impacts of Caregiver in Elderly Dementia Patients with Urinary Incontience—A Prospective Randomized Study", Ann. Meet. Int. Continence Soc., Abstract 166 (Oct. 5-9, 2003).
Magari et al., "Therapeutic Effects of Solifenacin Succinate on OAB: QOL Assessments using VAS in Cases with Pretreatment", The Japanese Journal of Urology, 99(2):323 (2008).
Bennett et al., "Cognitive Deficits in Rats after Forebrain Cholinergic Depletion are reversed by a novel NO Mimetic Nitrate Ester", Neuropsychopharmacology, 32:505-513 (2007).
Siegler et al., "Treatment of urinary incontinence with anticholinergics in patients taking cholinesterase inhibitors for dementia", Clinical Pharmacology and Therapeutics, 75(5):484-488 (2004).
Faber et al., "Enhancing the Tolerability of Tacrine with Propantheline", Am. J. Psychiatry, 156(1):156 (1999).
Sakakibara et al., "Care of OAB in elderly patients with dementia: therapy using a combination of donepezil and propiverine", The Japanese Journal of Urology, 99(2):323 (2008).
Cutler et al., "Antiemetic therapy for Alzheimer's patients receiving the cholinesterase inhibitor SDZ ENA 713", Clinical Pharmacology and Therapeutics, 63(2):188 (1998).
Novartis Pharmaceutical Corporation, "Exelon", Abstract XP002689197 dated Aug. 11, 2006, retrieved from http://www.pharma.us.novartis.com/cs/www.pharma.us.novartis.com/product/pi/pdf/exelon.pdf (retrieved on Dec. 13, 2012).
Fu et al., "Propantheline Attenuates the Peripheral Side Effects of Donepezil without Affecting Its Antiamnestic Properties in Cerebral Ischemic Mice", Journal of Health Science, 54(4):409-415 (2008).
Letters to the Editor, American J. Psychiatry, 156(1):156-161 (Jan. 1999).
Ikeda et al., Overactive Bladder Induced by Higher Dose of Donepezil Hydrochloride in a Patient with Senile Dementia of Alzheimer Type, Neurological Therapeutics, 25:609-612 (2008).
Notification of Reasons for Rejection for Japanese Application No. 2012-529733 dated Jul. 17, 2014.
Diez-Ariza et al., "Flumazenil and tacrine increase the effectiveness of ondansetron on scopolamine-induced impairment of spatial learning in rats", Psychopharmacology, 169:35-41 (2003).
Glycopyrrolate tablet, Daily Med (Currently Medical Information), [West-ward Pharmaceutical Corp] Human Prescription Drug Label, retrieved at http://dailymed.nim.nih.gov/dailymed/druginfo.cfm?id=65407, pp. 1-5 (Jun. 5, 2012).
Aricept(R) (Donepezil Hydrocholride Tablets) NDA 20-690/S-026, pp. 3-30 (2010).
Suzuki et al., "Effect of antimuscarinic drugs used for overactive bladder on learning in a rat passive avoidance response test", European Journal of Pharmacology, 557:154-158 (2007).
Extended Search Report issued in corresponding European Application No. 09726036.8 dated Apr. 19, 2011.
Anghelescu et al., "Acetylcholinesterasehemmer bei Demenz Lohnt die antidementive Therapie", MMW Fortschritte der Medizin, 149(2):76-78 (2007).
Scheife et al., "Central Nervous System Safety of Anticholinergic Drugs for the Treatment of Overactive Bladder in the Elderly", Clinical Therapeutics, 2(2):144-153 (2005).
Madersbacher, "Orale Anticholinergika bei uberaktiver Blase [Oral anticholinergics in overactive bladder]", Der Urologe. Ausg. A, 45(7):830-834 (2006).
Schultz-Lampel, "Blasendysfunktion bei Demenz und M. Alzheimer [Bladder disorders in patients with dementia]", Urologe A., 42(12):1579-1587 (2003).
Gottfries, "Alzheimer's disease and senile dementia: Biochemical characteristics and aspects of treatment", Psychopharmacology, 86:245-252 (1985).
Ropper, "A rational approach to dementia", CMA Journal, 121:1175-1190 (1979).
Martin et al., "Office evaluation of dementia: How to arrive at a clear diagnosis and choose appropriate therapy", Dementia, 84(3):176-187 (1988).
"Guidance for Industry: Estimating the Maximum Safe Starting Dose in Initial Clinical Trials for Therapeutics in Adult Healthy Volunteers", Pharmacology and Toxicology, pp. 1-27 (2005).
Notification of Reasons for Rejection for JPA 2011501792 dated May 16, 2014.

\* cited by examiner

ANTICHOLINERGIC NEUROPROTECTIVE COMPOSITION AND METHODS

This application is a Continuation of U.S. application Ser. No. 14/426,022 filed Mar. 4, 2015 (now allowed); which is a National Stage of International Application No. PCT/2013/058172 filed Sep. 5, 2013, which claims benefit of U.S. Provisional Application No. 61/696,978 filed Sep. 5, 2012; U.S. Provisional Application No. 61/697,021 filed Sep. 5, 2012; U.S. Provisional Application No. 61/697,039 filed Sep. 5, 2012; and U.S. Provisional Application No. 61/697,069 filed Sep. 5, 2012; the contents of all of which are incorporated herein by reference in their entirety.

FIELD OF THE INVENTION

The invention relates to a pharmaceutical composition comprising (a) a high dose of a non-selective peripheral anticholinergic agent (nsPAChA) selected from the group consisting of propiverine and pharmaceutically acceptable salts thereof, trospium and pharmaceutically acceptable salts thereof, glycopyrrolium and pharmaceutically acceptable salts thereof, and solifenacine and pharmaceutically acceptable salts thereof; (b) a non-anticholinergic antiemetic agent (naAEA); in admixture with a pharmaceutical carrier; and (c) a high dose of an aceytlcholine esterase inhibitor (AChEI). This composition is useful for safely increasing the blood levels of an acetylcholinesterase inhibitor (AChEI) in a human treated with said AChEI, thus reaching neuroprotective concentrations of the AChEI.

The invention provides the above pharmaceutical composition for use for safely increasing AChEI plasma concentrations in a human subject suffering from Alzheimer type dementia in the treatment of said subject with said AChEI, thus inducing neuroprotection. The invention also provides a pharmaceutical composition containing an nsPAChA dose from more than 2- to 8-times the dose used in the anticholinergic therapy, in admixture with a pharmaceutical carrier. Said composition is useful for inducing neuroprotection and combating neurodegeneration in a patient treated with an AChEI dose of from 2.5 to 7 times the maximal recommended dose of said AChEI.

The invention is related to a pharmaceutical composition containing a nsPAChA dose from 100% to 800% the dose of said nsPAChA used in the anticholinergic therapy, in admixture with a pharmaceutical carrier, for use for increasing the AChEI blood levels in humans. The invention also provides a pharmaceutical composition comprising (a) a high dose of a non-selective peripheral anticholinergic agent (nsPAChA) selected from the group consisting of solifenacin and pharmaceutically acceptable salts thereof; (b) a non anticholinergic antiemetic agent (naAEA); in admixture with a pharmaceutical carrier. This composition is useful for safely increasing the blood levels of an acetylcholinesterase inhibitor (AChEI) in a human treated with said AChEI, thus assuring neuroprotection.

The invention is also related to the above pharmaceutical composition for use for safely increasing AChEI blood levels in a human subject suffering from Alzheimer type dementia in the treatment of said subject with said AChEI, thus reaching neuroprotective concentrations of the AChEI.

The invention is related to a method for safely increasing AChEI blood levels in a human subject by administering to said subject the above composition in combination with an overdose of said AChEI, said human subject possibly being a patient suffering from Alzheimer type dementia.

The invention also provides a method for inducing neuroprotection in a patient suffering from Alzheimer type dementia, thus combating neurodegeneration and slowing disease progression, by administering to said patient a dose of a non-selective, peripheral anticholinergic agent (nsPAChA) which is more than twice the dose of said nsPAChA used in the anticholinergic therapy, in combination with an overdose of an acetylcholinesterase inhibitor (AChEI), said overdose being from 2.5 to 7 times the maximal recommended dose of said AChEI.

The invention also relates to a method for increasing the blood levels of an acetylcholinesterase inhibitor (AChEI) in a human subject by administering to said subject an overdose of said AChEI which is from 2.5 times to 7 times its maximum recommended dose, in combination with a dose of a non-selective, peripheral anticholinergic agent (nsPAChA) which is from 100% to 800% the dose of said nsPAChA used in the anticholinergic therapy, said human subject possibly being a patient suffering from Alzheimer type dementia.

The invention also provides a method for safely increasing AChEI blood levels in a human subject by administering to said subject the above composition in combination with an overdose of said AChEI, said human subject possibly being a patient suffering from Alzheimer type dementia.

DEFINITIONS

"AChE": Acetyl Choline Esterase.

"AChEI(s)": Acetyl Choline Esterase Inhibitor(s).

"nsPAChA(s)": non-selective, peripheral AntiCholinergic Agent(s).

"naAEA(s)": non-anticholinergic AntiEmetic Agent(s).

"Non-selective" (or non selective): referred to nsPAChAs, applies to anticholinergic agents exhibiting inhibitory activity broadly across the various subtypes of muscarinic M-receptors, namely the M1-M5 receptors, as currently identified.

"Peripheral": referred to nsPAChAs, applies to anticholinergics that are largely unable (have a limited ability) to enter the central nervous system following systemic administration and thus do not affect brain function to a clinically appreciable degree. These drugs can include both quaternary and tertiary ammonium anticholinergic agents, especially those having low lipid solubility.

"MTD": maximum (or maximal) tolerated dose, i.e. the highest dose of a drug or treatment that does not cause unacceptable side effects. The maximum tolerated dose is determined in clinical trials by testing increasing doses on different groups of people until the highest dose with acceptable side effects is found (NCI Drug Dictionary).

"AChEI overdose": an AChEI dose administered to a human subject, which is at least 2.5 times the MTD or maximum recommended dose in said human subject.

"Anticholinergic therapy": the treatment with an anticholinergic agent of gastro-intestinal cramping, nausea, retching, vomiting, fecal incontinence, bladder spasms, urinary incontinence, overactive bladder, asthma, motion sickness, muscular spasms, and smooth muscle contractive disorders or the treatment with an anticholinergic agent of side effects caused by AChEIs including, but not limited to gastro-intestinal cramping, nausea, retching, vomiting, fecal incontinence, bladder spasms, urinary incontinence, overactive bladder, asthma, motion sickness, muscular spasms, and smooth muscle contractive disorders.

"CNS": Central Nervous System.

"CSF": Cerebrospinal Fluid.

"PNS": Peripheral Nervous System.

"IR": Immediate Release of the active ingredient from a composition.

"ER": Extended Release (or sustained release) of the active ingredient from a composition by any administration route.

BACKGROUND OF THE INVENTION

Reduced levels of neurotransmitters including acetylcholine have been reported in dementias of the Alzheimer type. In particular, a deficit in acetylcholine-mediated transmission is thought to contribute to the cognitive and the neurobehavioral abnormalities associated with these disorders. Accordingly, drugs known to augment cholinergic transmission in the CNS are the mainstay of current therapy.

AChEIs are now not only part of the standard of care for patients suffering from a dementia of the Alzheimer type, but are also widely used off-label for various other chronic progressive disorders of cognitive function. AChEIs have the enhancement of acetylcholine-mediated neurotransmission as a general mechanism of action. All act in the human CNS to increase and prolong the availability of acetylcholine by inhibiting its degradatory enzyme acetylcholinesterase (AChE). Four AChEIs have been approved by the U.S. FDA for the treatment of Alzheimer's disease and for Parkinson's disease dementia: tacrine, donepezil [Aricept®], rivastigmine [Exelon®] and galantamine [Razadyne®]. AChEIs are available in various formulations including immediate release forms such as tablets, capsules and solutions as well as rapid dissolving and extended release forms for oral administration as well as those for parenteral (e.g. transdermal) administration.

In particular, tacrine is presented in capsules containing 10, 20, 30, 40 mg/capsule and is used at recommended daily dosages of from 40 to 160 mg (divided into 4 doses); donepezil is presented, as hydrochloride, in orally disintegrating tablets or in tablets to be swallowed containing 5 or 10 mg/tablet to be administered once a day and is used at recommended daily dosages of from 5 to 10 mg, and as a dose formulation containing 23 mg of donepezil HCl in a matrix type tablet to be administered once a day; rivastigmine is presented in capsules containing the hydrogen tartrate in amounts corresponding to 1.5, 3, 4.5 and 6 mg of rivastigmine base, as oral solution containing the tartrate corresponding to 2 mg of rivastigmine base and in form of a transdermal patch releasing rivastigmine at 4.6 mg/24 hours or 9.5 mg/24 hours, the recommended daily dosage for the IR forms being of from 6 to 12 mg, divided into 2 doses and the maximal studied patch dose being 13.3 mg/24 hours the maximal recommended patch dose being 18 mg/24 hours; and galantamine is available in ER capsules of 8 mg, 16 mg and 24 mg containing 10.253 mg, 20.506 mg and 30.758 mg, respectively, of galantamine hydrobromide, or in IR tablets containing 5.126, 10.253, and 15.379 mg of galantamine hydrobromide, respectively, corresponding to 4 mg, 8 mg and 12 mg, respectively, of galantamine base and as a 4 mg/mL oral solution, the recommended daily dosage being from 16 mg to 32 mg, in the United States of America the maximum recommended daily dose having been reduced to 24 mg divided into 2 doses.

Brief reviews of the efficacy of the AChEIs rivastigmine, donepezil and galantamine for the treatment of dementia diseases, by Angelescu et al., have been published in MMW-Fortschr. Med. Sonderheit, 2007, 149, 76-78 ("Angelescu 2007") and in the Cochrane Database Syst Review, 2006, Jan. 25(1): CD005593 ("Birks, 2006").

Other AChEIs, in particular tacrine analogs, such as ipidacrine; phenserine and their analogs; icopezil; and zanapezil are under evaluation. For example, phenserine is administered in IR 15 mg tablets and has been studied at a daily dose of 30 mg.

AChEIs vary in their pharmacological profiles and in their affinities for acetylcholinesterase and butyrylcholinesterase. Donepezil and galantamine are 1000- and 50-fold, respectively, more selective for acetylcholinesterase than for butyrylcholinesterase, whereas rivastigmine inhibits both enzymes with similar affinity (Thomsen et al., Life Scie. 1990, 46, 1553-58) and certain analogs of phenserine are more selective for butyrylcholinesterase (see for example Qian-sheng Yu et al., J Med Chem, 1997, 40(18), 2895-2898 and U.S. Pat. No. 6,683,105).

Carefully conducted clinical trials of donepezil (Rogers et al., Neurology 1998, 50, 136-45; Winblad et al. Neurology. 2001 Aug. 14; 57(3):489-95), rivastigimine (Rösler et al., Brit. Med. J. 1999, 318, 633-38; Farlow et al. Eur. Neurol., 2000, 44, 236-41) and galantamine (Raskind et al., Neurology, 2000, 54, 2261-68; Tariot et al., Neurology, 2000, 54, 2269-76) in patients with dementias of the Alzheimer type demonstrated small, but statistically significant, benefits on cognitive and global measures relevant to dementia. The magnitude of the effect in pivotal clinical trials was on the order of a 2.8 point improvement on the 70-point cognitive subscale of the Alzheimer's Disease Assessment Scale (ADAS-Cog), or 1-1.5 point improvement on the 30-point Mini-Mental Status Examination (MMSE) compared to placebo over six months. Differences in global measures assessed by the 7-point Clinician Interview-Based Impression of Change scale (CIBIC) were on the order of 0.3-0.5 points in patients receiving an AChEI compared to those receiving placebo. Efficacy was similar for the three commonly used AChEIs. AChEIs also appear to have a beneficial effect on the behavioral and neuropsychiatric symptoms in patients with Alzheimer type dementias. Moreover, rivastigmine was given open-label to patients with Parkinson's disease (PD) at an initial dose of 1.5 mg twice a day and the dose was increased after 4 weeks to 3 mg twice daily, after 8 weeks to 4.5 mg twice daily and after 12 weeks to a maximal dose of 6 mg twice daily by trying to keep the dose of rivastigmine constant at the maximal tolerated dose, between weeks 12 and 26 of the trial. According to the Authors, rivastigmine may improve the cognitive functions in PD patients with dementia with no worsening of motor function. (Giladi et al., Acta Neurol Scand 2003, 108, 368-373).

Unfortunately, however, none of the currently available medications offer more than modest clinical benefit for some patients suffering from any of the aforementioned dementing disorders, even when these medications are administered at their maximum safe and tolerated doses. This is the first problem limiting the success of current AChEI therapy of Alzheimer type dementias.

A second problem limiting the success of current AChEI therapy of Alzheimer type dementias is that, even at recommended amounts, all these drugs produce dose limiting adverse reactions, mainly by over-stimulating peripheral cholinergic receptors of the muscarinic type. As a result, signs and symptoms of untoward gastrointestinal, pulmonary, cardiovascular, urinary, and other systems dysfunction occur. These side effects commonly include, for the aforementioned AChEIs tacrine, donepezil, rivastigmine and galantamine: anorexia, nausea, vomiting, diarrhea, abdominal pain, weight loss; increased bronchial secretions, dyspnea, bronchoconstriction and bronchospasm; bradycardia, supraventricular cardiac conduction abnormalities, vasodilation, hypotension, dizziness and syncope; urinary bladder spasm, increased urinary frequency, and incontinence; flushing and diaphoresis; fatigue, headache, lacrymation, miosis, and loss of binocular vision (Physicians' Desk Reference 2008, Thomson PDR, Montvale, N.J.).

Adverse events attending the use of AChEIs appear to primarily reflect the excessive stimulation of peripheral cholinergic receptors, especially those of the muscarinic type (mAChRs). Five subtypes of muscarinic receptors, M1 through M5, have now been identified. Ongoing research has begun to map the distribution and physiologic role of these receptors as well as determine the binding affinity of drugs to them. For example, M1 receptors are found in sympathetic postganglionic neurons (autonomic ganglia), in gastric tissue and in the myenteric plexus; they are involved in secretions from salivary glands and the gastrointestinal tract. M2 receptors are present in cardiac and smooth muscle and have been implicated in the regulation of contractile forces of the atrial cardiac muscle and the conduction velocity of the atrioventricular node and thus heart rate. M2 receptors are also present on gastrointestinal smooth muscle as well as on detrusor smooth muscle cells and other structures within the bladder wall. M3 receptors are the predominant muscarinic receptor subtype mediating contraction of the stomach fundus, urinary bladder, and trachea. They are also expressed on glandular cells including gastric parietal cells and on vascular smooth muscle as well as detrusor smooth muscle and other structures within the bladder wall. M3 receptors are involved in exocrine gland secretion, smooth muscle contractility, emesis, pupil dilatation, food intake and weight gain.

It is also known that the degree to which AChEIs can attenuate the activity of this enzyme (acetylcholinesterase, AChE) in the CNS can be estimated by assays of AChE activity and related protein levels in the CSF and by use of cerebral imaging technology. It is reported that recommended maximal dose levels of these drugs typically achieve only about 35% AChE inhibition (without a concomitant increase in AChE protein levels) in the CNS of Alzheimer disease patients (Brannan S et al. ACNP 46th Annual Meeting, Program No. 4. Boca Raton Fla., Dec. 10, 2007—"Brannan 2007"; Farlow M et al AAN Poster 2008; Davidsson P et al Neurosci Lett 2001; 300:157-60; Amici S et al Mech Ageing Dev 2001; 122:2057-62) and that inhibition of AChE activity and cognitive improvement are significantly correlated (Giacobini et al. J Neural Transm. 2002 July; 109(7-8): 1053-65; Darreh-Shori T et al, J Neural Trans 2006; 113:1791-801) and that, ordinarily, a higher degree of enzyme blockade must be attained for maximum functional effect (Jann et al., Clin Pharmacokinet, 2002; 41(10):719-39—"Jann 2002").

On the other hand, doubling the dose of rivastigmine, which became clinically practical when AChEI administration by immediate release tablets was replaced by skin patches, which diminished side effects by blunting peak blood levels, significantly increased the amount of cognitive improvement in patients with Alzheimer's disease without increasing side effects. Similarly, a 23 mg dose of donepezil formulated in a matrix type tablet that tends to smooth out the sharp rise in peak drug concentrations following once daily administration and facilitates the tolerable administration of a 23 mg dose, produces a significantly greater cognitive benefit in Alzheimer Disease (AD) patients than the earlier 10 mg immediate-release dose formulation (Farlow et al, 2010).

The precise causes of the vomiting and related gastrointestinal symptoms so frequently induced by AChEI therapy are not established. Presumably, they reflect cholinergic receptor hyperstimulation attending AChEI administration. Vomiting is coordinated in a center located at the base of the brain. The vomiting center communicates with the nearby chemoreceptor trigger zone, whose stimulation can lead to such complaints of gastrointestinal distress as anorexia, nausea and vomiting.

By virtue of being dose limiting, adverse effects also constrain the efficacy of AChEI therapy. Studies in animal models of human cognitive dysfunction indicate a direct dose-response relation between the amount of acetyl choline esterase inhibition and the degree of cognitive improvement (Bennett B M et al., Neuropsychopharmacology. 2007 March; 32(3):505-513). Similar conclusions have been drawn regarding AChEI effects on cognitive and behavioral symptoms in human patients with Alzheimer's disease (Jann 2002; Winblad B. Cummings J, Andreasen N, Grossberg G, Onofrj M, Sadowsky C, Zechner S, Nagel J, Lane R. Int J Geriatr Psychiatry. 2007 May; 22(5): 456-67).

As set forth above, use of an AChEI to treat dementias of the Alzheimer type combined with a nsPAChA, which alleviates the peripheral cholinergic side effects of the AChEI, or combined with a naAEA, which alleviates nausea and vomiting caused by the AChEI, fails to realize the full potential benefits of this approach to therapy. While potentially lessening side effects and thereby enabling the use of higher and thus more effective doses of the AChEI, merely employing the concomitant use of antiemetics, such as domperidone and others, or of anticholinergics such as propantheline, oxybutynin, tolterodine and others, falls short of achieving the utmost therapeutic advantages of AChEIs in the treatment Alzheimer type dementias. Further implementation of this concept will confer far greater advantage to individuals suffering from these disorders.

An improvement in the treatment of Alzheimer type dementia is attained by a combined therapy associating an nsPAChA, at a dose of from 20% to 200% the current daily doses, with an AChEI, at a dose up to 4 times the maximal tolerated dose of said AChEI when administered alone, as disclosed in WO 2009/120277. By such a treatment, a higher acetylcholinesterase inhibition in the CNS is achieved and greater relief of the symptoms of Alzheimer type dementia is enabled, by concomitantly decreasing concurrent adverse effects.

Similarly, WO 2011/034568 discloses an improvement in the treatment of Alzheimer type dementia which is attained by a combined therapy associating a non-anticholinergic-antiemetic agent, at a dose of from 50% to 300% the current IR daily doses, with an AChEI, at a dose up to 3 times the recommended doses of said AChEI when administered alone.

Notwithstanding the real progress achieved by treating Alzheimer disease patients with up to 200% of the nsPAChA currently used doses in IR or ER forms or with up to 300% of the naAEAs currently used doses in IR forms together with AChEIs, there is a need for further increasing AChE inhibition in the CNS of said patients.

There is substantial evidence from preclinical studies that AChEIs may affect basic processes that have been implicated in Alzheimer Disease (AD) pathogenesis, suggesting that these drugs could have both disease-modifying and neuroprotective effects in humans. The evidence seems to be strongest in relation to donepezil (reviewed in Jacobson and Sabbagh, 2008). There is also evidence from studies in Alzheimer patients that these treatments could slow disease progression. For example Roundtree et al, (2009) report on 20-year retrospective study conducted at an Academic center in 641 Alzheimer patients. In a linear model, greater anti-dementia drug use was significantly associated with slower rate of decline as measure on the Mini Mental State Examination (MMSE; p<0.0001), the ADAS-Cog (p<0.01), the Physical Self-Maintenance Scale (PMS; p<0.05), the Instrumental Activities of Daily Living (IADL; p<0.0001) and the Clinical Dementia Rating-Sum of Boxes (CDR-SB; p<0.001). The magnitude of the treatment effect, however, was small. Rate of change in mean scores indicated that treated patients would have declined less on the rating scales: 1 point/year on the MMSE, 0.4 points/year on the PMS, 1.4 point/year on the IADL, and 0.6 point/year on the CDR-SB. Although clinically and statistically significant, these treatment effects remain modest (Shanks et al, *Cholinesterase inhibition: is there evidence for disease-modifying effects?* Curr Med Res Opin. 2009, 25: 2439-46).

Studies in animal models of AD show a dose-response for neuro-protection and suggest that the doses currently used in patients may be too low for disease modification (i.e, slowing of disease progression). For example, a study by Dong et al (Hongxin Dong, Carla M. Yuede, Carolyn A. Coughlan, Keely M. Murphy, and John G. Csernansky. *Effects of Donepezil on Amyloid-β and Synapse Density in the Tg2576 Mouse Model of Alzheimer's Disease Brain Res.* 2009 December 15; 1303: 169-178) examined a possible neuro-protective effect of donepezil in a transgenic mouse model of AD, the Tg2576 mouse model of AD. This model overexpresses the human amyloid precursor protein (hAPP), and is one of the most well characterized mouse models of AD. In this model, at approximately 9 months of age, A-beta deposits appear in cortical and limbic brain regions and indications of cellular inflammation and behavioral deficits emerge (reviewed in Dong et al, 2009). In a previous study, Dong et al, (Hongxin Dong, Cynthia A. Csernansky, Maureen V. Martin, Amy Bertchume, Dana Vallera, and John G. Csernansky. *Acetylcholinesterase inhibitors ameliorate behavioral deficits in the Tg2576 mouse model of Alzheimer's disease.* Psychopharmacology (Berl). 2005 August; 181(1): 145-152) had shown that donepezil (0.1, 0.3 and 1.0 mg/kg for 6 weeks) improved learning and memory functions in Tg2576 mice, but did not affect A-beta deposition. In the "neuroprotective study," (Dong et al, 2009), higher doses of donepezil (0, 1, 2, and 4 mg/kg/day) were administered chronically in drinking water to Tg2576 mice beginning at 3 months and ending at 9 months of age, when A-beta deposits and behavioral deficits usually become apparent. Concentrations of A-beta, synaptic protein (synaptophysin) and synapse density in the hippocampus were measured following the long-term administration of donepezil. Results showed that administration of 4 mg/kg/day of donepezil, as compared to vehicle, significantly reduced brain tissue soluble A-beta 1-40 and 1-42, A-beta plaque number and burden. Furthermore, donepezil 4 mg/kg also significantly increased synaptic density in the molecular layer of the dentate gyrus of Tg2576 mice. Lower doses of donepezil (1 and 2 mg/kg) were not effective on these parameters. Taken together the results of the study show that a dose of 4 mg/kg/day of donepezil is neuroprotective in a mouse model of AD, but lower doses were not effective. Thus, in Alzheimer patients, the administration of doses higher than the currently approved doses of donepezil should be neuroprotective and should slow disease progression. A similar dose-related neuroprotective effect has also been observed with rivastigmine and other AChEIs (Shanks et al. *Cholinesterase inhibition: is there evidence for disease-modifying effects?* Curr Med Res Opin 2009, October; 25 (10): 2439-46).

Thus, by further increasing the safe and tolerable dose of an AChEI it will be possible to take advantage of their enhanced pharmacological activity not only in relation to palliative effects but also in relation to neuroprotective effects, thus retarding progression of the underlying dementing disorder.

However, as set forth above, even by using the method disclosed in WO 2009/120277 or WO 2011/034568, it is presently not possible to increase also beyond 4-times the therapeutic dose of AChEI to be administered to a patient without inducing intolerable cholinergic or emetic, from any origin, adverse effects, as those described above.

In particular, the increase of the AChEI doses by the concurrent suppression of the peripheral cholinergic adverse effects, including emesis, does not completely suppress vomiting caused by AChEI overdoses and, in any case, an antiemetic agent must be added to the AChEI. By consequence, if the AChEI doses are increased, the treated subject should take either a triple nsPAChA/AChEI/naAEA combination or an nsPAChA/AChEI fixed combination and an antiemetic. Under these conditions, on one side, it could be difficult to adjust the AChEI doses in function of both the co-administered nsPAChA and antiemetic agent, and, on the other side, the administration of a triple combination providing concurrent or sequential, but separate AChEI, nsPAChA and antiemetic administrations could give rise to dangerous and even fatal mistakes in said administrations, especially in the context of the population suffering from a dementia of Alzheimer type.

The present invention is directed to overcoming these and other deficiencies in the art.

SUMMARY OF THE INVENTION

The present invention is based on the realistic hypothesis that (a) the results of Dong 2009 and Meunier 2006 (Meunier et al. *The anti-amnestic and neuroprotective effects of donepezil against amyloid beta 25-35 peptide-induced toxicity in mice involve interaction with the signal receptor.* Br. J. Pharmacol, 2006, December; 149: 998-1012) are applicable to humans, (b) there is a dose-effect relationship and (c) by increasing the dose of donepezil, or of another AChEI, a neuroprotective effect is induced.

By applying the results of Dong et al. and others to humans, it has been observed that the maximum recommended daily doses of the used AChEIs do not achieve the neuroprotective threshold for AChEIs. Even the recent matrix type 23 mg dose of donepezil does not allow the attainment of said threshold neuroprotective levels.

It has now been found that the Dong et al. results are applicable to humans and that it is possible to safely reach and go above the neuroprotective threshold in the CNS. In fact, it has now been discovered that the nsPAChAs, when administered to a human being who is treated with a given dose of an AChEI, induce blood levels of said AChEI which are higher than the blood levels achieved in the same individual after administration of the same dose of said AChEI given alone.

As set forth above, an nsPAChA is able to increase the maximum tolerated dose of an AChEI up to 4-fold; but, surprisingly, it has been found that the increase in AChEI blood concentrations in a subject treated with the nsPAChA/AChEI combination and in whom the maximum tolerated dose increased, for example, by two or three times the maximum tolerated AChEI dose reached with the AChEI alone, was much higher than expected, given that the increase in plasma concentrations with AChEIs administered alone has been shown to be linearly dose-dependent within the dose ranges studied. This synergism was unexpected.

In addition, and even more surprisingly, it has been found that the administration of overdoses of nsPAChAs (from more than twice to eight times the maximum dose used in the anticholinergic therapy) in combination with overdoses of AChEIs (from 2.5 to 7 times the maximum dose used in the treatment of Alzheimer type dementias) is safer than that with lower doses of nsPAChAs, the sole residual adverse effect being emesis which can be controlled by an appropriate dose of an antiemetic agent, and induces neuroprotection.

This synergism involves a great flexibility in the treatment of neurodegeneration. In fact, according to the present invention, in the case of a patient suffering from Alzheimer type dementia treated with a given dose of AChEI, it is possible either to administer to said patient an overdose of nsPAChA, thus increasing the supply of acetylcholine to the CNS of said patient without increasing the AChEI dose, or to administer said patient an overdose of a nsPAChA by concurrently increase the AChEI dose, thus safely supplying high amounts of acetylcholine to the CNS of said patient thus assuring neuroprotection.

In this connection, the unexpected finding was that, in subjects treated with a nsPAChA/AChEI combination, the average plasma concentrations of the AChEI increased by 20% over the average plasma concentrations measured after administration of the same dose of AChEI alone and, more surprisingly, that in the same subjects and at the same nsPAChA dose in said combination, the increase tends to be greater at higher AChEI doses.

By chronic administration of the combination of nsPAChA/AChEI, overdoses, the potential, but heretofore barely, if at all, expressed neuroprotective action of the AChEIs is enabled and enhanced, thus allowing the neurodegenerative process to slow and therefore allowing to delay disease progression.

Moreover, it has been found that the combination of the synergistic action of the nsPAChAs on AChE inhibition by the AChEIs, inducing higher than expected AChEI blood levels and consequent increased concentrations of acetylcholine in the CNS, with the concurrent, continuous opposing action of the nsPAChAs (peripheral only) and of the AChEI (both central and peripheral), allows for the theoretically infinite increase of the doses of the nsPAChA/AChEI pair without untoward peripheral anticholinergic side effects, thus allowing the treatment of patients suffering from dementia of Alzheimer type with very high doses of both nsPAChA, i.e. from more than twice to 8 times the nsPAChA doses used in the anticholinergic therapy, and AChEI, i.e. from 2.5 to 7 times the AChEI doses used in the treatment of Alzheimer type dementia.

Before the present invention, as noted above, doubling the dose of rivastigmine by replacing immediate release tablets by skin patches, that blunt the peak blood levels, increased the amount of cognitive improvement in patients with Alzheimer's disease without significantly increasing side effects. According to the present invention, although ER formulations such as rivastigmine patches are also provided, this is not strictly necessary because, by means of IR compositions of the invention, very high blood levels of AChEI such as rivastigmine can be achieved without intolerable side effects.

It has also been found that a pharmaceutical composition comprising (a) an nsPAChA selected from the group consisting of 1-methyl-4-[(2,2-diphenyl-2-n-propoxy)acetoxy]piperidine (propiverine) and pharmaceutically acceptable salts thereof, in an amount of from 15 mg to 240 mg; 3-(2-hydroxy-2,2-diphenylacetoxy)-spiro[bicyclo[3.2.1]octane-8,1'-pyrrolidin]-1'-ium (trospium) pharmaceutically acceptable salts, in an amount of from 20 mg to 480 mg; and 3-(2-cyclopentyl-2-hydroxy-2-phenylacetoxy)-1,1-dimethylpyrrolidinium (glycopyrrolium) pharmaceutically acceptable salts, in an amount of from 2 mg to 16 mg; and (b) a naAEA; in admixture with a pharmaceutical carrier, is able to increase the administered AChEI dose up to a factor of 7, thus allowing the safe overcome of the neuroprotective threshold in the CNS of patients suffering from a dementia of Alzheimer type, and combating neurodegeneration in patients, suffering from a dementia of Alzheimer type, without appreciable signs of cholinergic and/or emetic adverse effects. The pharmaceutically acceptable salts of propiverine include the propiverine quaternary $(C_1-C_4)$alkylammonium halides, in particular the 1,1-dimethyl-4-[(2,2-diphenyl-2-n-propoxy)acetoxy]piperidininum chloride (methylpropiverinium chloride), the 1,1-dimethyl-4-[(2,2-diphenyl-2-n-propoxy)acetoxy]piperidininum iodide (methylpropiverinium iodide) and, the 1,1-dimethyl-4-[(2,2-diphenyl-2-n-propoxy)acetoxy]piperidininum bromide (methylpropiverinium bromide).

Even though, according to the previous findings, it is possible to increase the AChEI doses by using low doses of nsPAChA in order to improve the conditions of patients suffering from Alzheimer type dementia, with respect to the previous disclosures, the composition of the present invention has the advantage of (a) inducing a safe increase of the AChEI blood levels by using AChEI doses which are at least 2.5 Limes higher than the maximal recommended daily doses in the treatment of Alzheimer type dementia; (b) safely increasing the AChEI doses up to 7 times the maximum recommended doses and, consequently, to considerably increase AChEI concentrations in the CNS, thus enabling neuroprotection; (c) being administered once or twice a day; and (d), in contrast with the fixed-dose combination described in WO 2009/120277 and WO 2011/034568, allowing a correct administration of the AChEI in function of the duration of action of said AChEI.

Additionally, even though, according to the previous findings, it is possible to increase the AChEI doses by using low doses of nsPAChA in order to improve the conditions of patients suffering from Alzheimer type dementia, it has been found that, by further increasing the doses of nsPAChA up to 8 times the doses approved for anticholinergic therapy, it is possible (a) to induce neuroprotection by using AChEI doses which are at least 2.5 times higher than the maximal recommended daily doses in the treatment of Alzheimer type dementia; and (b) to safely increase the AChEI doses up to 7 times, and even more, the maximum recommended daily doses with a consequent, considerable increase in acetylcholine concentrations in the CNS.

In summary, high AChEI blood levels and consequent neuroprotection are obtained by a therapeutic method providing the administration of combined overdoses of both an nsPAChA and an ACHEI to a patient suffering from Alzheimer type dementia. In this therapeutic method, the best results are obtained when an antiemetic agent is added to the therapy, said antiemetic agent having the sole effect of counteracting the emetic effects of said AChEI overdose, thus improving patient compliance of said therapy.

It has been found that the administration of solifenacin/antiemetic composition, when administered in combination with an AChEI, in particular with donepezil, avoids the need for the usual prolonged titration period of the AChEI dose because it allows the direct, safe administration of the maximum recommended dose, and even of overdoses, of each AChEI to human subjects, including patients suffering from Alzheimer type dementia.

High AChEI blood levels are safely obtained by a therapeutic method providing the administration of solifenacin/naAEA fixed combination and an AChEI overdose to a human subject, said subject possibly being a patient suffering from Alzheimer type dementia, thus allowing a safe adjustment of the AChEI doses of from 2.5 times to 7 times the maximum recommended doses of said AChEI and inducing neuroprotection.

It has been found that the administration of an nsPAChA/AChEI combination avoids the need for the usual prolonged titration period of the AChEI dose because it allows the direct, safe administration of the maximum recommended dose, and even of overdoses, of each AChEI to human subjects, including patients suffering from Alzheimer type dementia, such that an increase of the maximum tolerated doses coincides with the increase of the maximum recommended doses of each AChEI.

It has now been discovered that the nsPAChAs, when administered to a human being treated with a given dose of an AChEI, induce blood levels of said AChEI which are higher than the blood levels achieved in the same individual after administration of the same dose of said AChEI given alone.

As set forth above, an nsPAChA is able to increase the maximum tolerated dose of an AChEI up to 4-fold; but, surprisingly, it has been found that AChEI blood levels in a subject treated with the nsPAChA/AChEI combination, in whom the maximum tolerated AChEI dose increased, for example, by two or three times the maximum tolerated dose reached with the AChEI alone, are much higher than expected, given that the increase in plasma concentrations with AChEIs administered alone has been shown to be linearly dose-dependent within the dose ranges studied. This synergism was unexpected.

This synergism involves a great flexibility in the treatment of neurodegeneration. In fact, according to the present invention, in the case of a patient suffering from Alzheimer type dementia treated with a given dose of AChEI, it is possible either to administer to said patient an overdose of nsPAChA, thus increasing the supply of concentrations of AChEIs to the CNS of said patient without increasing the AChEI dose, or to administer said patient an overdose of a nsPAChA by concurrently increase the AChEI dose, thus safely supplying high concentrations of AChEIs to the CNS of said patient thus assuring neuroprotection.

Moreover, it has been found that the combination of the synergistic action of the nsPAChAs on AChE inhibition by the AChEIs, inducing higher than expected AChEI blood levels and consequent increased concentrations of acetylcholine in the CNS, with the concurrent, continuous opposing action of the nsPAChAs (peripheral only) and of the AChEI (both central and peripheral), allows for the theoretically infinite increase of the doses of the nsPAChA/AChEI pair without untoward peripheral anticholinergic side effects, thus allowing the treatment of patients suffering from dementia of Alzheimer type with high doses of both nsPAChA, i.e. from 100% to 8 times the nsPAChA doses used in the anticholinergic therapy, and AChEI, i.e. from 2.5 to 7 times, and even more, the AChEI doses used in the treatment of Alzheimer type dementia.

Thus, even though, according to the previous findings, it is possible to increase the AChEI doses by using low doses of nsPAChA in order to improve the conditions of patients suffering from Alzheimer type dementia, it has been found that, by further increasing the doses of nsPAChA up to 8 times the doses approved for anticholinergic treatment, it is possible (a) to induce an increase of the AChEI blood levels by using AChEI doses which are at least 2.5 times higher than the maximal recommended daily doses in the treatment of Alzheimer type dementia; and (b) to safely increase the AChEI doses up to 7 times the maximum recommended daily doses and, consequently, to considerably increase AChEI concentrations in the CNS.

Before the present invention, as noted above, the replacement of immediate release tablets by skin patches, which diminished side effects by blunting AChEI peak blood levels, allowed higher AChEI doses and produced greater cognitive benefit in patients with Alzheimer-type disease without inducing unacceptable side effects. Although the present invention can be applied to ER formulations such as patches, this is not really necessary, since by means of the invention alone very high blood AChEI levels can be achieved without intolerable side effects.

In summary, high AChEI blood levels are obtained by a therapeutic method providing the administration of combined high doses of both an nsPAChA and an ACHEI to a human subject, said subject possibly being a patient suffering from Alzheimer type dementia. In this therapeutic method, the best results are obtained when an antiemetic agent is added to the therapy, said antiemetic agent having the sole effect of counteracting the emetic effects of said AChEI overdose, thus improving patient compliance to said therapy.

Before the present invention, as noted above, doubling the dose of rivastigmine by replacing immediate release tablets by skin patches, that blunt the peak blood levels, increased the amount of cognitive improvement in patients with Alzheimer's disease without significantly increasing side effects. According to the present invention, although ER formulations such as rivastigmine patches are also provided, this is not strictly necessary because, by means of IR compositions of the invention, very high blood levels of AChEI such as rivastigmine can be achieved without intolerable side effects.

It has been found that the administration of an nsPAChA/AChEI combination avoids the need for the usual prolonged titration period of the AChEI dose because it allows the direct, safe administration of the maximum recommended dose, and even of overdoses, of each AChEI to human subjects, including patients suffering from Alzheimer type dementia, such that an increase of the maximum tolerated doses coincides with the increase of the maximum recommended doses of each AChEI.

Moreover, it has been found that the combination of the synergistic action of the nsPAChAs on AChE inhibition by the AChEIs, inducing higher than expected AChEI blood levels and consequent increased concentrations of AChEIs in the CNS, with the concurrent, continuous opposing action of the nsPAChAs (peripheral only) and of the AChEI (both central and peripheral), allows for the theoretically infinite increase of the doses of the nsPAChA/AChEI pair without untoward peripheral anticholinergic side effects, allows the treatment of patients suffering from dementia of Alzheimer type with very high doses of both nsPAChA, i.e. from more than twice to 8 times the nsPAChA doses used in the anticholinergic therapy, and AChEI, i.e. from 2.5 to 7 times the AChEI doses used in the treatment of Alzheimer type dementia.

It has also been found that a pharmaceutical composition comprising (a) an nsPAChA selected from the group consisting of (1S)-(3R)-1-azabicyclo[2.2.2]oct-3-yl 3,4-dihydro-1-phenyl-2(1H)-iso-quinolinecarboxylate (solifenacin) and pharmaceutically acceptable salts and compounds thereof, in an amount which is equivalent to from 10 mg to 80 mg of solifenacin succinate; and (b) a naAEA; in admixture with a pharmaceutical carrier, is able to increase the administered AChEI dose up to a factor of 7, thus allowing the safe overcome of the neuroprotective threshold in the CNS of patients suffering from a dementia of Alzheimer type, and combating neurodegeneration in patients, suffering from a dementia of Alzheimer type, without appreciable signs of cholinergic and/or emetic adverse effects. The pharmaceutically acceptable salts and compounds of solifenacin include the quaternary ammonium salts, in particular the methylchloride (methylsolifenacinium chloride), the methyliodide (methylsolifenacinium iodide) and the methylbromide (methylsolifenacinium bromide).

Thus, even though, according to the previous findings, it is possible to increase the AChEI doses by using low doses of nsPAChA in order to improve the conditions of patients suffering from Alzheimer type dementia, with respect to the previous disclosures the composition of the present invention has the advantage of (a) inducing a safe increase of AChEI blood levels with AChEI doses which are at least 2.5 times higher than the maximal recommended daily doses in the treatment of Alzheimer type dementia; (b) safely increasing the AChEI doses up to 7 times the maximum recommended doses and, consequently, to considerably increase AChEI concentrations in the CNS, thus allowing for neuroprotection; (c) being administered once per day; and (d), in contrast with the fixed-dose combination described in WO 2009/120277 and WO 2011/034568, allowing a correct administration of the AChEI in function of the duration of action of said AChEI.

In summary, high AChEI blood levels are safely obtained by a therapeutic method providing the administration of solifenacin/naAEA fixed combination and an AChEI overdose to a human subject, said subject possibly being a patient suffering from Alzheimer type dementia, thus allowing a safe adjustment of the AChEI doses of from 2.5 times to 7 times the maximum recommended doses of said AChEI and inducing neuroprotection.

It has been found that the administration of solifenacin/antiemetic composition, when administered in combination with an AChEI, in particular with donepezil, avoids the need for the usual prolonged titration period of the AChEI dose because it not only allows the direct, safe administration of the maximum recommended dose of the AChEI, but also of even much higher doses, of each AChEI to human subjects, including patients suffering from Alzheimer type dementia.

One aspect of the present invention is related to a pharmaceutical composition comprising a nsPAChA selected from the group consisting of propiverine and pharmaceutically acceptable salts thereof, in an amount which is equivalent to from 15 mg to 120 mg of propiverine hydrochloride; trospium pharmaceutically acceptable salts, in an amount which is equivalent to from 20 mg to 480 mg of trospium chloride, and glycopyrrolium pharmaceutically acceptable salts, in an amount which is equivalent to from 2 mg to 16 mg of glycopyrronium bromide; and (b) a non-anticholinergic antiemetic agent (naAEA); in admixture with a pharmaceutical carrier.

In one embodiment the composition is such that the nsPAChA is propiverine hydrochloride, in an amount of from 31 mg to 240 mg. In another embodiment, the composition is such that nsPAChA is trospium chloride, in an amount of from 61 mg to 480 mg. In another embodiment, the composition is such that nsPAChA is glycopyrrolium bromide, in an amount of from 4.1 mg to 16 mg. In another embodiment, the composition is such that Component (b) is a naAEA selected from the group consisting of (b1) 5HT3-antagonists, (b2) DA-antagonists, (b3) H1-antagonists, (b4) cannabinoids, (b5) aprepitant.

In another embodiment, the composition is such that naAEA is selected from the group consisting of alosetron and pharmaceutically acceptable salts and solvates thereof, in an amount (in alosetron) of from 0.5 mg to 3 mg; dolasetron and pharmaceutically acceptable salts thereof, in an amount (in dolasetron) of from 50 mg to 300 mg; granisetron and pharmaceutically acceptable salts thereof, in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg; bromopride and pharmaceutically acceptable salts and solvates thereof, in an amount (in bromopride) of from 10 mg to 30 mg; clebopride and pharmaceutically acceptable salts thereof, in an amount (in clebopride) of from 0.5 mg to 1.5 mg; and aprepitant, in an amount of from 40 mg to 375 mg.

In yet another embodiment, the composition is such that Component (b) is a naAEA selected from the group consisting of alosetron and pharmaceutically acceptable salts and solvates thereof in an amount (in alosetron) of from 0.5 mg to 3 mg; dolasetron and pharmaceutically acceptable salts and solvates thereof in an amount (in dolasetron) of from 50 mg to 300 mg; granisetron and pharmaceutically acceptable salts and solvates thereof in an amount (in granisetron) of from 1 mg to 3 mg; ondansetron and pharmaceutically acceptable salts and solvates thereof in an amount (in ondansetron) of from 4 mg to 24 mg; tropisetron and pharmaceutically acceptable salts and solvates thereof in an amount of from 5 mg to 15 mg; domperidone and pharmaceutically acceptable salts and solvates thereof, in an amount (in domperidone) of from 10 mg to 30 mg; and metoclopramide and pharmaceutically acceptable salts and solvates thereof, in an amount (in metoclopramide) of from 10 mg to 30 mg.

In another embodiment, the composition is such that naAEA is selected from the group consisting of alosetron and pharmaceutically acceptable salts and solvates thereof, in an amount (in alosetron) of from 0.5 mg to 3 mg; granisetron and pharmaceutically acceptable salts and solvates thereof in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

In another embodiment, the composition is such that nsPAChA Component (a) is selected from the group consisting of propiverine and pharmaceutically acceptable salts thereof, in an amount which is equivalent to from 15 mg to 120 mg of propiverine hydrochloride; trospium pharmaceutically acceptable salts, in an amount which is equivalent to from 20 mg to 480 mg of trospium chloride; and glycopyrrolium pharmaceutically acceptable salts, in an amount which is equivalent to from 2 mg to 16 mg of glycopyrronium bromide; and (b) and said naAEA is selected from the group consisting of alosetron and pharmaceutically acceptable salts and solvates thereof, in an amount (in alosetron) of from 0.5 mg to 3 mg; granisetron and pharmaceutically acceptable salts and solvates thereof in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

The present invention is also related to a method for inducing neuroprotection, thus combating neurodegeneration, and consequently slowing disease progression in a patient suffering from a dementia of the Alzheimer type, which comprises administering to said patient an AChEI daily dose which is at least 2.5, up to 7 times the maximum recommended dose daily of said AChEI used in the treatment of Alzheimer type dementias, in combination with a pharmaceutical composition comprising (a) an nsPAChA selected from the group consisting of propiverine and pharmaceutically acceptable salts thereof, in an amount which is equivalent to from 15 mg to 120 mg of propiverine hydrochloride; trospium pharmaceutically acceptable salts, in an amount which is equivalent to from 20 mg to 480 mg of trospium chloride; and glycopyrrolium pharmaceutically acceptable salts, in an amount which is equivalent to from 2 mg to 16 mg of glycopyrronium bromide; and (b) a non-anticholinergic antiemetic agent (naAEA); in admixture with a pharmaceutical carrier.

The compositions of the present invention can be used for inducing neuroprotection, thus combating neurodegeneration, in a patient suffering from a dementia of Alzheimer type, in combination with an AChEI.

Another aspect of the present invention is related to a pharmaceutical composition comprising an nsPAChA selected from the group consisting of (1S)-(3R)-1-azabicyclo[2.2.2]oct-3-yl 3,4-dihydro-1-phenyl-2(1H)-isoquinolinecarboxylate and pharmaceutically acceptable salts and compounds thereof, in an amount which is equivalent to from 10 mg to 80 mg of solifenacin succinate; and (b) a non-anticholinergic antiemetic agent (naAEA); in admixture with a pharmaceutical carrier.

In one embodiment according to the above aspect of the present invention, the composition is such that nsPAChA is present in an amount which is equivalent to from 11 mg to 80 mg of solifenacin succinate. In another embodiment, the composition is such that nsPAChA is present in an amount which is equivalent to from 15 mg to 80 mg of solifenacin succinate. In yet another embodiment, the composition is such that nsPAChA is present in an amount which is equivalent to from 21 mg to 80 mg of solifenacin succinate.

A composition according to the present invention is such that Component (b) is a naAEA selected from the group consisting of (b1) 5HT3-antagonists, (b2) DA-antagonists, (b3) H1-antagonists, (b4) cannabinoids, (b5) aprepitant.

In another embodiment, the composition is such that Component (b) is selected from the group consisting of alosetron and pharmaceutically acceptable salts and solvates thereof in an amount (in alosetron) of from 0.5 mg to 3 mg; dolasetron and pharmaceutically acceptable salts and solvates thereof in an amount (in dolasetron) of from 50 mg to 300 mg; granisetron and pharmaceutically acceptable salts and solvates thereof in an amount (in granisetron) of from 1 mg to 3 mg; ondansetron and pharmaceutically acceptable salts and solvates thereof in an amount (in ondansetron) of from 4 mg to 24 mg; tropisetron and pharmaceutically acceptable salts and solvates thereof in an amount of from 5 mg to 15 mg; domperidone and pharmaceutically acceptable salts and solvates thereof, in an amount (in domperidone) of from 10 mg to 30 mg; and metoclopramide and pharmaceutically acceptable salts and solvates thereof, in an amount (in metoclopramide) of from 10 mg to 30 mg.

In yet another embodiment, the composition is such that naAEA is selected from the group consisting of alosetron and pharmaceutically acceptable salts and solvates thereof, in an amount (in alosetron) of from 0.5 mg to 3 mg; dolasetron and pharmaceutically acceptable salts thereof, in an amount (in dolasetron) of from 50 mg to 300 mg; granisetron and pharmaceutically acceptable salts thereof, in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg; bromopride and pharmaceutically acceptable salts and solvates thereof, in an amount (in bromopride) of from 10 mg to 30 mg; clebopride and pharmaceutically acceptable salts thereof, in an amount (in clebopride) of from 0.5 mg to 1.5 mg; and aprepitant, in an amount of from 40 mg to 375 mg.

In another embodiment, the composition is such that naAEA is selected from the group consisting of alosetron and pharmaceutically acceptable salts and solvates thereof, in an amount (in alosetron) of from 0.5 mg to 3 mg; granisetron and pharmaceutically acceptable salts and solvates thereof in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

In another embodiment, the composition is such that nsPAChA Component (a) is present in an amount which is equivalent to from 11 mg to 80 mg of solifenacin succinate and said naAEA is selected from the group consisting of alosetron and pharmaceutically acceptable salts and solvates thereof, in an amount (in alosetron) of from 0.5 mg to 3 mg; granisetron and pharmaceutically acceptable salts and solvates thereof in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

In yet another embodiment, the composition is such that nsPAChA Component (a) is present in an amount which is equivalent to from 15 mg to 80 mg of solifenacin succinate and said naAEA Component (b) is selected from the group consisting of alosetron and pharmaceutically acceptable salts and solvates thereof, in an amount (in alosetron) of from 0.5 mg to 3 mg; granisetron and pharmaceutically acceptable salts and solvates thereof in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

In another embodiment, the composition is such that nsPAChA Component (a) is present in an amount which is equivalent to from 21 mg to 80 mg of solifenacin succinate and said naAEA Component (b) is selected from the group consisting of alosetron and pharmaceutically acceptable salts and solvates thereof, in an amount (in alosetron) of from 0.5 mg to 3 mg; granisetron and pharmaceutically acceptable salts and solvates thereof in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

The present invention is related to a method for inducing neuroprotection, thus combating neurodegeneration, and consequently slowing disease progression in a patient suffering from a dementia of the Alzheimer type, which comprises administering to said patient an AChEI daily dose which is at least 2.5, up to 7 times the maximum recommended dose daily of said AChEI used in the treatment of Alzheimer type dementias, in combination with a pharmaceutical composition comprising an nsPAChA selected from the group consisting of (1S)-(3R)-1-azabicyclo[2.2.2]oct-3-yl 3,4-dihydro-1-phenyl-2(1H)-isoquinolinecarboxylate and pharmaceutically acceptable salts and compounds thereof, in an amount which is equivalent to from 10 mg to 80 mg of solifenacin succinate; and (b) a non-anticholinergic antiemetic agent (naAEA); in admixture with a pharmaceutical carrier.

The composition of the present invention can be used for inducing neuroprotection, thus combating neurodegeneration, in a patient suffering from a dementia of Alzheimer type, in combination with an AChEI.

Another aspect of the present invention is related to a method for inducing neuroprotection in a patient suffering from an Alzheimer type dementia, which comprises administering said patient an AChEI dose which is at least 2.5, up to 7 times the maximum recommended dose used in the treatment of Alzheimer type dementias, in combination with an nsPAChA dose which is more than twice, up to 8 times the dose used in the anticholinergic therapy.

In one embodiment, the method is such that AChEI is selected from the group consisting of (±)-2,3-dihydro-5,6-dimethoxy-2-[[1-(phenylmethyl)-4-piperidinyl]methyl]-1H-inden-1-one (donepezil) and its pharmaceutically acceptable salts, (S)—N-Ethyl-N-methyl-3-[1-(dimethylamino)ethyl]-phenyl carbamate (rivastigmine) and its pharmaceutically acceptable salts, 4aS,6R,8aS-3-methoxy-11-methyl-4a,5,9,10,11,12-hexahydroxy-6H-benzofuro[3a,3,2-e,f]benzazepin-6-ol (galantamine) and its pharmaceutically acceptable salts; and (1R,9S,13E)-1-amino-13-ethylidene-11-methyl-6-azatricyclo[7.3.1.0$^{2,7}$]trideca-2(7),3,10-trien-5-one (Huperzine A).

In one embodiment, method of the present invention is such that AChEI is donepezil or a pharmaceutically acceptable salt thereof, at a daily dose of from 25 mg to 151 mg. In another embodiment, the method of the present invention is such that AChEI is rivastigmine or a pharmaceutically acceptable salt thereof, at a daily dose of from 30 mg to 93 mg. In another embodiment, the method of is such that AChEI is galantamine or a pharmaceutically acceptable salt thereof, at a dose of from 60 mg to 224 mg. The method of the present invention is such that AChEI is huperzine A, at a dose of from 0.45 mg to 4.8 mg.

In another embodiment, the method of the present invention is such that nsPAChA is selected from the group consisting of (1S)-(3R)-1-azabicyclo[2.2.2]oct-3-yl 3,4-dihydro-1-phenyl-2(1H)-isoquinolinecarboxylate (solifenacin) and pharmaceutically acceptable salt and compounds thereof, 1-methyl-4-[(2,2-diphenyl-2-n-propoxy)acetoxy] piperidine (propiverine) and pharmaceutically acceptable salts thereof, 3-(2-hydroxy-2,2-diphenylacetoxy)-spiro[bicyclo[3.2.1]octane-8,1'-pyrrolidin]-1'-ium (trospium) pharmaceutically acceptable salts, and 3-(2-cyclopentyl-2-hydroxy-2-phenylacetoxy)-1,1-dimethylpyrrolidinium (glycopyrrolium) pharmaceutically acceptable salts.

In another embodiment, the method of the present invention is such that nsPAChA is administered at a daily dose which is from more than 200% to 800% the dose used in the anticholinergic therapy. In one embodiment, the method of the present invention is such that nsPAChA is trospium chloride, in an IR formulation administered at daily a dose of from more than 80 mg to 360 mg. In another embodiment, the method of the present invention is such that nsPAChA is trospium chloride, in an ER formulation administered at a daily dose of from more than 120 mg to 480 mg.

The method according to the present invention also includes nsPAChA as propiverine hydrochloride, in an IR or ER formulation administered at a dose of from more than 60 mg to 240 mg. In one embodiment, the method of present invention is such that nsPAChA is solifenacin succinate, in an IR formulation administered at a daily dose of from more than 20 mg to 80 mg. Also, the method of the present invention is such that AChEI is donepezil hydrochloride, administered at a daily dose of from 25 mg to 151 mg and said nsPAChA is solifenacin succinate, administered at a daily dose of from 21 mg to 80 mg.

In one embodiment, the method of the present invention is such that AChEI is galantamine hydrobromide, administered at a daily dose (in galantamine) of from 60 mg to 224 mg, and said nsPAChA is propiverine, as hydrochloride, administered at a daily dose of from 61 mg to 240 mg. In another embodiment, the method of the present invention is such that AChEI is rivastigmine, as hydrogen tartrate, administered at a daily dose of from 30 mg to 93 mg, and said nsPAChA is selected from the group consisting of trospium chloride, administered at a daily dose of from 80 mg to 480 mg; propiverine, as hydrochloride, administered at a daily dose of from 61 mg to 240 mg; and solifenacin succinate, administered at a daily dose of from 21 mg to 80 mg.

Another aspect of the present invention is related to a pharmaceutical composition comprising, as an active ingredient, an nsPAChA selected from the group consisting of solifenacin and pharmaceutically acceptable salts thereof, propiverine and pharmaceutically acceptable salts thereof, glycopyrronium pharmaceutically acceptable salts and trospium pharmaceutically acceptable salts, in an amount which is from more than 200% to 800% the maximum amount of said nsPAChA contained in compositions indicated for the anticholinergic therapy, for use for inducing neuroprotection and combating neurodegeneration in a patient suffering from a dementia of Alzheimer type who is treated with an AChEI dose which is from 250% to 700% the maximum recommended dose of said AChEI.

In one embodiment, the composition of the present invention is such that nsPAChA is selected from the group consisting of trospium chloride, in an amount of from more than 40 mg to 480 mg; solifenacin succinate, in an amount of from more than 20 mg to 80 mg; and propiverine hydrochloride, in an amount of from more than 30 mg to 240 mg. In another embodiment, the composition of the present invention is such that nsPAChA selected from the group consisting of glycopyrrolium bromide, in an amount of from 4.2 mg to 16 mg, in admixture with a pharmaceutical carrier in an IR formulation; trospium chloride in an amount of from 42 mg to 160 mg, in admixture with a pharmaceutical carrier in an IR formulation; trospium chloride in an amount of from 126 mg to 480 mg, in admixture with a pharmaceutical carrier, in an ER formulation; solifenacin succinate in an amount of from 21 mg to 80 mg, in admixture with a pharmaceutical carrier in an IR formulation; propiverine hydrochloride in an amount of from 31.5 mg to 120 mg, in admixture with a pharmaceutical carrier in an IR formulation; and propiverine hydrochloride in an amount of from 61 mg to 240 mg, in admixture with a pharmaceutical carrier in an ER formulation.

In another embodiment, the composition of the present invention is such that nsPAChA is selected from the group consisting of glycopyrronium bromide in an amount of from 4.5 mg to 16 mg, in admixture with a pharmaceutical carrier in an IR formulation; trospium chloride in an amount of from 60 mg to 160 mg, in admixture with a pharmaceutical carrier in an IR formulation; solifenacin succinate in an amount of from 25 mg to 80 mg, in admixture with a pharmaceutical carrier in an IR formulation; and propiverine hydrochloride in an amount of from 31.5 mg to 120 mg, in admixture with a pharmaceutical carrier in an IR formulation. In another embodiment, the composition of the present invention can be used for inducing neuroprotection and combating neurodegeneration in a patient suffering from an Alzheimer type dementia who is treated with an AChEI dose which is from 2.5 to 7 times higher than the maximum recommended dose of said AChEI.

The present invention is also related to a method for increasing AChEI blood concentrations in a human being, which comprises administering said human being a nsPAChA dose which is at least equal to, up to 8 times the dose used in the anticholinergic therapy, in combination with an AChEI dose which is at least 2.5, times, up to 7 times the dose of said AChEI used in the treatment of Alzheimer type dementias. In one embodiment, the method of the present invention is such that human being is a patient suffering from an Alzheimer type dementia and said combination is administered chronically.

The method of present invention is such that AChEI is selected from the group consisting of (±)-2,3-dihydro-5,6-dimethoxy-2-[[1-(phenylmethyl)-4-piperidinyl]methyl]-1H-inden-1-one (donepezil) and its pharmaceutically acceptable salts, (S)—N-Ethyl-N-methyl-3-[1-(dimethylamino)ethyl]-phenyl carbamate (rivastigmine) and its pharmaceutically acceptable salts, 4aS,6R,8aS-3-methoxy-11-methyl-4a,5,9,10,11,12-hexahydroxy-6H-benzofuro[3a,3,2-e,f]benzazepin-6-ol (galantamine) and its pharmaceutically acceptable salts; and (1R,9S,13E)-1-amino-13-ethylidene-11-methyl-6-azatricyclo[7.3.1.0$^{2,7}$]trideca-2(7),3,10-trien-5-one (Huperzine A).

In one embodiment, the method of the present invention is such that AChEI is donepezil or a pharmaceutically acceptable salt thereof, at a daily dose of from 25 mg to 151 mg. In another embodiment, the method of the present invention is such that AChEI is rivastigmine or a pharmaceutically acceptable salt thereof, at a daily dose of from 30 mg to 126 mg.

In another embodiment, the method of the present invention is such that AChEI is galantamine or a pharmaceutically acceptable salt thereof, at a daily dose of from 60 mg to 224 mg. In yet another embodiment, the method of the present invention is such that AChEI is huperzine A, at a daily dose of from 0.45 mg to 4.8 mg. In another embodiment, the method of the present invention is such that nsPAChA is selected from the group consisting of (1S)-(3R)-1-azabicyclo[2.2.2]oct-3-yl 3,4-dihydro-1-phenyl-2(1H)-isoquinolinecarboxylate (solifenacin) and pharmaceutically acceptable salt and compounds thereof, 1-methyl-4-[(2,2-diphenyl-2-n-propoxy)acetoxy]piperidine (propiverine) and pharmaceutically acceptable salts thereof, 3-(2-hydroxy-2,2-diphenylacetoxy)-spiro[bicyclo[3.2.1]octane-8,1'-pyrrolidin]-1'-ium (trospium) pharmaceutically acceptable salts, and 3-(2-cyclopentyl-2-hydroxy-2-phenylacetoxy)-1,1-dimethylpyrrolidinium (glycopyrrolium) pharmaceutically acceptable salts.

In yet another embodiment, the method of the present invention is such that nsPAChA is trospium chloride, in an IR formulation administered at a daily dose of from 40 mg to 360 mg. In another embodiment, the method is such that nsPAChA is trospium chloride, in an ER formulation administered at a daily dose of from 60 mg to 480 mg. In another embodiment, the method is such that nsPAChA is propiverine hydrochloride, in an IR or ER formulation administered at a daily dose of from 30 mg to 120 mg. In another embodiment, the method is such that nsPAChA is solifenacin succinate, in an IR formulation administered at a daily dose of from 10 mg to 80 mg.

In another embodiment, the method of the present invention is such that AChEI is donepezil hydrochloride, administered at a daily dose of from 25 to 60 mg and said nsPAChA is solifenacin succinate, in an IR formulation administered at a daily dose of from 10 mg to 20 mg. In yet another embodiment, the method according to the present invention is such that AChEI is galantamine hydrobromide, administered at a daily dose of from 60 to 168 mg, in an IR or ER formulation and said nsPAChA is propiverine hydrochloride, in an IR or, respectively, ER formulation administered at a daily dose of from 30 mg to 120 mg. In one embodiment, the method according to the present invention is such that doses of both the AChEI and the nsPAChA are in IR formulations.

The present invention is also related to a pharmaceutical composition comprising, as an active ingredient, an nsPAChA selected from the group consisting of solifenacin and pharmaceutically acceptable salts thereof, propiverine and pharmaceutically acceptable salts thereof, glycopyrronium pharmaceutically acceptable salts and trospium pharmaceutically acceptable salts, in an amount which is from 100% to 800% the maximum amount of said nsPAChA contained in compositions indicated for the anticholinergic therapy, for use for increasing the AChEI blood levels in a human treated with an AChEI dose which is from 250% to 700% the maximum tolerated dose and maximum recommended dose of said AChEI.

In one embodiment, the composition is such that nsPAChA active ingredient is selected from the group consisting of glycopyrrolium bromide, in an amount of from 2 mg to 16 mg, in admixture with a pharmaceutical carrier in an IR formulation; trospium chloride in an amount of from 20 mg to 160 mg in an IR formulation; trospium chloride in an amount of from 60 mg to 480 mg in an ER formulation; solifenacin succinate in an amount of from 10 mg to 20 mg in an IR formulation; propiverine hydrochloride in an amount of from 15 mg to 120 mg in an IR formulation; and propiverine hydrochloride in an amount of from 30 mg to 240 mg in an ER formulation.

DETAILED DECRYPTION OF THE INVENTION

I. First Aspect of the Present Invention

In a first aspect, the present invention provides a pharmaceutical composition comprising a nsPAChA selected from the group consisting of propiverine and pharmaceutically acceptable salts thereof, trospium pharmaceutically acceptable salts and glycopyrrolium pharmaceutically acceptable salts; and a naAEA, in admixture with a pharmaceutical carrier.

More particularly, it is an object of the present invention to provide a composition comprising (a) an nsPAChA selected from the group consisting of 1-methyl-4-[(2,2-diphenyl-2-n-propoxy)acetoxy]piperidine (propiverine) and pharmaceutically acceptable salts thereof, in an amount which is equivalent to from 15 mg to 240 mg of propiverine hydrochloride; 3-(2-hydroxy-2,2-diphenylacetoxy)-spiro[bicyclo[3.2.]octane-8,1'-pyrrolidin]-1'-ium (trospium) pharmaceutically acceptable salts, in an amount which is equivalent to from 20 mg to 480 mg of trospium chloride; and 3-(2-cyclopentyl-2-hydroxy-2-phenylacetoxy)-1,1-dimethylpyrrolidinium (glycopyrrolium) pharmaceutically acceptable salts, in an amount which is equivalent to from 2 mg to 16 mg of glycopyrrolium bromide; and (b) a naAEA; in admixture with a pharmaceutical carrier.

Propiverine and pharmaceutically acceptable salts thereof, in particular its hydrochloride, are described in DD 106643, CN 1285348, CN 102218063(A), KR 2005-0011138, KR 2005-0011139, KR20110111782 (A) and in WO 2011/114195. The propiverine quaternary salts, i.e. the $(C_1-C_4)$alkyl propiverinium halides may be prepared by reacting 1-methyl-4-[(2,2-diphenyl-2-propoxy)acetoxy]piperidine (propiverine base) with a $(C_1-C_4)$alkyl halide (chloride, bromide or iodide), the propiverine base starting material being also obtained as crude product as described in WO 2011/114195 or by hydrolysis of propiverine hydrochloride, which is an easily available commercial product also obtainable for example as described in DD 106643, CN 1285348, CN 102218063(A) KR 2005-0011138, KR 2005-0011139, KR20110111782 (A) or in the aforesaid WO 2011/114195. In practice, an aqueous suspension of propiverine hydrochloride is treated with an inorganic base and crude propiverine base is recovered by extraction from an organic solvent and evaporation of the solvent; and the residue is treated with a $(C_1-C_4)$alkyl (preferably methyl) halide (chloride, bromide or iodide) in an alcoholic solution and the 1-alkyl-1-methyl-4-[(2,2-diphenyl-2-propoxy)acetoxy]piperidinium halide which precipitates is isolated.

Trospium chloride is described in U.S. Pat. No. 3,480,626 and other pharmaceutically acceptable salts thereof are cited in US 2006/0293356.

Glycopyrronium pharmaceutical acceptable salts, in particular the bromide, are obtainable according to U.S. Pat. No. 2,956,062.

Component (a) is a nsPAChA selected from the group consisting of propiverine and pharmaceutically acceptable salts thereof, in an amount which is equivalent to from 15 mg to 120 mg of propiverine hydrochloride; trospium pharmaceutically acceptable salts, in an amount which is equivalent to from 20 mg to 480 mg of trospium chloride; and glycopyrrolium pharmaceutically acceptable salts, in an amount which is equivalent to from 2 mg to 16 mg of glycopyrronium bromide Advantageously, the nsPAChA Component (a) of the composition is selected from the group consisting of propiverine hydrochloride, in an amount of from 15 mg to 240 mg, advantageously from 30 mg to 240 mg, preferably from 31 mg to 240 mg; trospium chloride, in an amount of from 20 mg to 480 mg, advantageously from 40 mg to 480 mg, preferably from 61 mg to 480 mg; and glycopyrrolium bromide, in an amount of from 2 mg to 16 mg, advantageously from 4 mg to 16 mg, preferably from 4.1 to 16 mg.

According to a preferred embodiment, the nsPAChA Component (a) is selected from the group consisting of propiverine hydrochloride in an amount of from 15 mg to 120 mg, advantageously from 30 mg to 120 mg, preferably from 31 mg to 120 mg, most preferably from 31 mg to 90 mg, in admixture with a pharmaceutical carrier in an IR formulation; propiverine hydrochloride in an amount of from 30 mg to 240 mg, advantageously from 60 mg to 240 mg, preferably from 61 mg to 240 mg, most preferably from 61 mg to 180 mg, in admixture with a pharmaceutical carrier in an ER formulation; trospium chloride in an amount of from 20 mg to 180 mg, from 40 mg to 160 mg preferably from 61 mg to 160 mg, most preferably from 61 mg to 140 mg, in admixture with a pharmaceutical carrier in an IR formulation, trospium chloride in an amount of from 60 mg to 480 mg, advantageously from 120 mg to 480 mg, preferably from 121 mg to 480 mg, most preferably from 61 mg to 360 mg, in admixture with a pharmaceutical carrier in an ER formulation; and glycopyrrolium bromide, in an amount of from 2 mg to 16 mg, advantageously from 4 mg to 16 mg, preferably from 4.1 to 16 mg, most preferably from 4.1 mg to 12 mg, in admixture with a pharmaceutical carrier in an IR formulation.

The naAEA Component (b) is present in an amount of from 100% to 300% of the amount of the said naAEA contained as a sole active ingredient in the currently used brand or generic drugs.

According to a preferred embodiment, said Component (b) is a non-anticholinergic antiemetic agent selected from the group consisting of (b1) 5HT3-antagonists, (b2) DA-antagonists, (b3) H1-antagonists, (b4) cannabinoids, (b5) aprepitant. Typical naAEAs of the above classes are illustrated in WO 2011/034568.

An advantageous Component (b) is selected from the group consisting of alosetron and pharmaceutically acceptable salts and solvates thereof, in particular the hydrochloride, in an amount (in alosetron) of from 0.5 mg to 3 mg; dolasetron and pharmaceutically acceptable salts and solvates thereof, in particular the mesylate, in an amount (in dolasetron) of from 50 mg to 300 mg; granisetron and pharmaceutically acceptable salts and solvates thereof, in particular the hydrochloride, in an amount (in granisetron) of from 1 mg to 3 mg; ondansetron and pharmaceutically acceptable salts and solvates thereof, in particular the hydrochloride dihydrate, in an amount (in ondansetron) of from 4 mg to 24 mg; tropisetron and pharmaceutically acceptable salts and solvates thereof, in particular the hydrochloride, in an amount of from 5 mg to 15 mg; domperidone and pharmaceutically acceptable salts and solvates thereof, in an amount (in domperidone) of from 10 mg to 30 mg; haloperidol, in an amount of from 1 mg to 30 mg; chlorpromazine and pharmaceutically acceptable salts and solvates thereof, in particular the hydrochloride, in an amount (in chlorpromazine) of from 25 mg to 75 mg; prochlorperazine and pharmaceutically acceptable salts and solvates thereof, in particular the dimaleate, in an amount (in prochlorperazine) of from 5 mg to 30 mg; metoclopramide and pharmaceutically acceptable salts and solvates thereof, in particular the monohydrochloride monohydrate, in an amount (in metoclopramide) of from 10 mg to 30 mg; bromopride and pharmaceutically acceptable salts and solvates, in particular the monohydrochloride and the dihydrochloride monohydrate, in an amount (in bromopride) of from 10 mg to 30 mg; clebopride and pharmaceutically acceptable salts and solvates thereof, in particular the hydrogen malate and the hydrochloride monohydrate, in an amount (in clebopride) of from 0.5 mg to 1.5 mg; levosulpiride, in an amount of from 25 mg to 300 mg; alizapride and pharmaceutically acceptable salts thereof, in particular the hydrochloride, in an amount (in alizapride) of from 50 mg to 150 mg; trimethobenzamide and pharmaceutically acceptable salts thereof such as the monohydrochloride, in an amount (in trimethobenzamide) of from 300 mg to 900 mg; meclizine and pharmaceutically acceptable salts and solvates thereof, in an amount (in meclizine) of from 13 mg to 150 mg; promethazine and pharmaceutically acceptable salts and solvates thereof, in particular the hydrochloride, in an amount (in prometazine) of from 25 mg to 150 mg; dronabinol in an amount of from 2.5 mg to 60 mg; nabilone, in an amount of from 2 mg to 12 mg; and aprepitant, in an amount of from 40 mg to 375 mg.

An advantageous non-anticholinergic antiemetic agent Component (b) in said pharmaceutical composition is selected from the group consisting of alosetron and pharmaceutically acceptable salts and solvates thereof, in an amount (in alosetron) of from 0.5 mg to 3 mg; dolasetron and pharmaceutically acceptable salts thereof, in an amount (in dolasetron) of from 50 mg to 300 mg; granisetron and pharmaceutically acceptable salts and solvates thereof, in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts and solvates thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg; bromopride and pharmaceutically acceptable salts and solvates thereof, in an amount (in bromopride) of from 10 mg to 30 mg; clebopride and pharmaceutically acceptable salts thereof, in an amount (in clebopride) of from 0.5 mg to 1.5 mg; and aprepitant, in an amount of from 40 mg to 375 mg.

Preferred Component (b) is a naAEA selected from the group consisting of alosetron and pharmaceutically acceptable salts and solvates thereof, in an amount (in alosetron) of from 0.5 mg to 3 mg; granisetron and pharmaceutically acceptable salts and solvates thereof, in particular the hydrochloride, in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

A composition comprising (a) a nsPAChA selected from the group consisting of propiverine hydrochloride, in an amount of from 15 mg to 240 mg, advantageously from 30 mg to 240 mg, preferably from 31 mg to 240 mg, most preferably from 31 mg to 180 mg; trospium chloride, in an amount of from 20 mg to 480 mg, advantageously from 40 mg to 480 mg, preferably from 61 mg to 480 mg, most preferably from 61 mg to 360 mg; and glycopyrrolium bromide, in an amount of from 2 mg to 16 mg, advantageously from 4 mg to 16 mg, preferably from 4.1 to 16 mg, most preferably from 4.1 mg to 12 mg; and (b) a naAEA selected from the group consisting of granisetron hydrochloride in an amount (in granisetron) of from 1 mg to 3 mg, ondansetron hydrochloride dihydrate in an amount (in ondansetron) of from 4 mg to 24 mg, domperidone in an amount of from 10 mg to 30 mg; and metoclopramide monohydrochloride monohydrate in an amount (in metoclopramide) of from 10 mg to 30 mg, in admixture with a pharmaceutical carrier, is particularly preferred.

The pharmaceutical compositions of the present invention are formulated in unit form for oral use, preferably in an immediate release formulation.

The unit form of the present invention may be a tablet, a capsule, or a pre-measured amount of granulate for oral administration comprising Component (a) and Component (b). In said unit form the nsPAChA and the naAEA may be mixed together or separated according to known technologies in admixture with a pharmaceutical carrier in a pharmaceutical composition.

Component (a) and Component (b) are formulated with conventional pharmaceutical carriers in known formulations for oral use wherein said components are mixed together or separated, for example in two tablets introduced in a capsule or in a two-compartment capsule or in a multilayer (di-layer) tablet wherein the two components are both in IR form, even though the association nsPAChA/naAEA may be formulated in tablets in which one or both of the two components is in controlled-release formulation, for example as a dispersion of said component in hydroxypropyl methyl cellulose or in a film-coated microgranule. Advantageously, the nsPAChA, in a ER-formulation is in the core and the naAEA, in IR-formulation, is in the outer layer in multi-layer tablets in which, for example, both the core and the outer layer are coated with a film. Analogously, capsules made of two separated parts, one containing Component (a), in IR- or ER-formulation and the other containing Component (b), in IR- or ER-formulation, according to known technologies, may be used.

The pharmaceutical carriers and vehicles are those commonly used for the preparation of compositions for oral, buccal and parenteral, in particular transdermal, administration. Appropriate unit forms comprise the oral forms such as tablets, soft or hard gelatin capsules, powders or granulates in sachets and suitably measured oral solutions or suspensions as well as patches for transdermal administration.

Component (a) and Component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and Component (b) may also be formulated in the form of microcapsules, optionally with one or more carriers or additives.

For oral administration, Component (a) and Component (b), together or separately, are formulated by mixing the active ingredient with conventional pharmaceutical acceptable carriers enabling said active ingredients to be formulated in tablets, dragees, orally disintegrating tablets, capsules and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubrifiants such as polyethylenglycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

The sweeteners contained in the orally disintegrating tablets may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The composition according to the present invention may be in form of a capsule containing two tablets as described herein above, one of them comprising Component (a) and the other comprising Component (b).

Advantageous ER administration formulations are in form of a transdermal patch manufactured according to known technologies, for administering the nsPAChA/antiemetic composition continuously and transdermally through a selected area of intact skin in a controlled manner for a prolonged period of time to induce high AChEI blood levels in a human subject, in particular to a patient suffering from a dementia of Alzheimer type, said subject or patient being treated with said AChEI. Said high AChEI blood levels enable acetylcholine concentrations in the brain to rise sufficiently to afford neuroprotection.

Carriers and vehicles for ER formulations include retardant materials such as acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

In particular, the unit forms of the present invention comprise (a) a nsPAChA selected from the group consisting of propiverine hydrochloride, in an amount of from 15 mg to 240 mg, advantageously from 30 mg to 240 mg, preferably from 31 mg to 240 mg, most preferably from 31 mg to 180 mg; trospium chloride, in an amount of from 20 mg to 480 mg, advantageously from 40 mg to 480 mg, preferably from 61 mg to 480 mg, most preferably from 61 mg to 360 mg; and glycopyrrolium bromide, in an amount of from 2 mg to 16 mg, advantageously from 4 mg to 16 mg, preferably from 4.1 to 16 mg, most preferably from 4.1 mg to 12 mg; and (b) a naAEA selected from the group consisting of domperidone, in an amount of from 10 mg to 30 mg; metoclopramide monohydrochloride monohydrate, in an amount (in metoclopramide) of from 10 mg to 30 mg; alosetron hydrochloride, in an amount, in alosetron of from 0.5-mg to 3 mg), dolasetron mesylate, in an amount of from 50 mg to 300 mg; granisetron hydrochloride in an amount, in granisetron, of from 1 mg to 3 mg; ondansetron hydrochloride monohydrate in an amount, in ondansetron, of from 4 to 24 mg; tropisetron hydrochloride in an amount, in tropisetron, of from 5 mg to 15 mg; and aprepitant, in an amount of from 40 mg to 375 mg.

According to an embodiment, the compositions of the present invention are formulated by mixing a nsPAChA selected from the group consisting of propiverine hydrochloride, trospium chloride and glycopyrrolium bromide, as Component (a), and the naAEA, as Component (b), together with a pharmaceutical carrier and compressed to a tablet for an immediate release or introduced in a soft or hard capsule for an immediate release.

An advantageous propiverine/granisetron composition according to this embodiment comprises
from 15 mg to 120 mg of propiverine hydrochloride, as Component (a); and
from 1 mg to 3 mg of granisetron (as hydrochloride);
as mixed together and with a pharmaceutical carrier in an IR formulation.

A first particularly advantageous propiverine/granisetron composition comprises
15 mg of propiverine hydrochloride, as Component (a); and
1 mg of granisetron (as hydrochloride), as Component (b),
as mixed together and with a pharmaceutical carrier in an IR formulation.

A second particularly advantageous propiverine/granisetron composition according to this embodiment comprises
30 mg of propiverine hydrochloride, as Component (a); and
1 mg of granisetron (as hydrochloride), as Component (b),
as mixed together and with a pharmaceutical carrier in an IR formulation.

A third advantageous propiverine/granisetron composition according to this embodiment comprises
31 mg of propiverine hydrochloride, as Component (a); and
1 mg of granisetron (as hydrochloride), as Component (b),
as mixed together and with a pharmaceutical carrier in an IR formulation.

A fourth advantageous propiverine/granisetron composition according to this embodiment comprises
35 mg of propiverine hydrochloride, as Component (a); and 2 mg of granisetron (as hydrochloride), as Component (b), as mixed together and with a pharmaceutical carrier in an IR formulation.

A fifth advantageous propiverine/granisetron composition according to this embodiment comprises
  45 mg of propiverine hydrochloride, as Component (a); and
  2 mg of granisetron (as hydrochloride), as Component (b),
as mixed together and with a pharmaceutical carrier in an IR formulation.

A sixth advantageous propiverine/granisetron composition according to this embodiment comprises
  60 mg of propiverine hydrochloride, as Component (a); and
  2 mg of granisetron (as hydrochloride), as Component (b),
as mixed together and with a pharmaceutical carrier in an IR formulation.

A seventh advantageous propiverine/granisetron composition according to this embodiment comprises
  60 mg of propiverine hydrochloride, as Component (a); and
  3 mg of granisetron (as hydrochloride), as Component (b),
as mixed together and with a pharmaceutical carrier in an IR formulation.

An advantageous propiverine/ondansetron composition according to this embodiment comprises
  from 15 mg to 120 mg of propiverine hydrochloride, as Component (a); and
  from 4 mg to 24 mg of ondansetron (as hydrochloride dihydrate);
as mixed together and with a pharmaceutical carrier in an IR formulation.

A first particularly advantageous propiverine/ondansetron composition according to this embodiment comprises
  15 mg of propiverine hydrochloride, as Component (a); and
  4 mg of ondansetron (as hydrochloride dihydrate), as Component (b),
as mixed together and with a pharmaceutical carrier in an IR formulation.

A second particularly advantageous propiverine/ondansetron composition according to this embodiment comprises
  30 mg of propiverine hydrochloride, as Component (a); and
  4 mg of ondansetron (as hydrochloride dihydrate), as Component (b),
as mixed together and with a pharmaceutical carrier in an IR formulation.

A third advantageous propiverine/ondansetron composition according to this embodiment comprises
  31 mg of propiverine hydrochloride, as Component (a); and
  4 mg of ondansetron (as hydrochloride dihydrate), as Component (b),
as mixed together and with a pharmaceutical carrier in an IR formulation.

A fourth advantageous propiverine/ondansetron composition according to this embodiment comprises
  45 mg of propiverine hydrochloride, as Component (a); and
  8 mg of ondansetron (as hydrochloride dihydrate), as Component (b),
as mixed together and with a pharmaceutical carrier in an IR formulation.

A fifth advantageous propiverine/ondansetron composition according to this embodiment comprises
  60 mg of propiverine hydrochloride, as Component (a); and
  8 mg of ondansetron (as hydrochloride dihydrate), as Component (b),
as mixed together and with a pharmaceutical carrier in an IR formulation.

An advantageous propiverine/tropisetron composition according to this embodiment comprises
  from 15 mg to 120 mg of propiverine hydrochloride, as Component (a); and
  from 5 mg to 15 mg of tropisetron (as hydrochloride), as Component (b);
as mixed together and with a pharmaceutical carrier in an IR formulation.

A first particularly advantageous propiverine/tropisetron composition according to this embodiment comprises
  35 mg of propiverine hydrochloride, as Component (a); and
  5 mg of tropisetron (as hydrochloride), as Component (b),
as mixed together and with a pharmaceutical carrier in an IR formulation.

A second particularly advantageous propiverine/tropisetron composition according to this embodiment comprises
  35 mg of propiverine hydrochloride, as Component (a); and
  5 mg of tropisetron (as hydrochloride), as Component (b),
as mixed together and with a pharmaceutical carrier in an IR formulation.

A third advantageous propiverine/tropisetron composition according to this embodiment comprises
  45 mg of propiverine hydrochloride, as Component (a); and
  10 mg of tropisetron (as hydrochloride), as Component (b),
as mixed together and with a pharmaceutical carrier in an IR formulation.

An advantageous propiverine/dolasetron composition according to this embodiment comprises
  from 15 mg to 120 mg of propiverine hydrochloride, as Component (a); and
  from 50 mg to 300 mg of dolasetron (as mesylate), as Component (b);
as mixed together and with a pharmaceutical carrier in an IR formulation.

A particular advantageous propiverine/dolasetron composition according to this embodiment comprises
  15 mg, 17.5 mg or 20 mg of propiverine hydrochloride, as Component (a); and
  50 mg of dolasetron (as mesylate), as Component (b);
as mixed together and with a pharmaceutical carrier in an IR formulation.

An advantageous propiverine/domperidone composition according to this embodiment comprises
  from 15 mg to 120 mg of propiverine hydrochloride, as Component (a); and
  from 10 mg to 30 mg of domperidone, as Component (b);
as mixed together and with a pharmaceutical carrier in an IR formulation.

A first particularly advantageous propiverine/domperidone composition according to this embodiment comprises
  15 mg of propiverine hydrochloride, as Component (a); and
  10 mg of domperidone, as Component (b),
as mixed together and with a pharmaceutical carrier in an IR formulation.

A second particularly advantageous propiverine/domperidone composition according to this embodiment comprises 31 mg of propiverine hydrochloride, as Component (a); and 10 mg of domperidone, as Component (b), as mixed together and with a pharmaceutical carrier in an IR formulation.

A third advantageous propiverine/domperidone composition according to this embodiment comprises 45 mg of propiverine hydrochloride, as Component (a); and 20 mg of domperidone, as Component (b), as mixed together and with a pharmaceutical carrier in an IR formulation.

A fourth advantageous propiverine/domperidone composition according to this embodiment comprises 60 mg of propiverine hydrochloride, as Component (a); and 30 mg of domperidone, as Component (b), as mixed together and with a pharmaceutical carrier in an IR formulation.

An advantageous propiverine/metoclopramide composition according to this embodiment comprises from 15 mg to 120 mg of propiverine hydrochloride, as Component (a); and from 10 mg to 30 mg of metoclopramide (as monohydrochloride monohydrate), as Component (b);

as mixed together and with a pharmaceutical carrier in an IR formulation.

A first particularly advantageous propiverine/metoclopramide composition according to this embodiment comprises 15 mg of propiverine hydrochloride, as Component (a); and 10 mg of metoclopramide (as monohydrochloride monohydrate), as Component (b), as mixed together and with a pharmaceutical carrier in an IR formulation.

A second particularly advantageous propiverine/metoclopramide composition according to this embodiment comprises 31 mg of propiverine hydrochloride, as Component (a); and 10 mg of metoclopramide (as monohydrochloride monohydrate), as Component (b), as mixed together and with a pharmaceutical carrier in an IR formulation.

A third advantageous propiverine/metoclopramide composition according to this embodiment comprises 45 mg of propiverine hydrochloride, as Component (a); and 20 mg of metoclopramide (as monohydrochloride monohydrate), as Component (b), as mixed together and with a pharmaceutical carrier in an IR formulation.

A fourth advantageous propiverine/metoclopramide composition according to this embodiment comprises 60 mg of propiverine hydrochloride, as Component (a); and 30 mg of metoclopramide (as monohydrochloride monohydrate), as Component (b), as mixed together and with a pharmaceutical carrier in an IR formulation.

An advantageous trospium/granisetron composition according to this embodiment comprises from 20 mg to 160 mg of trospium chloride, as Component (a); and from 1 mg to 3 mg of granisetron (as hydrochloride);

as mixed together and with a pharmaceutical carrier in an IR formulation.

A first particularly advantageous trospium/granisetron composition comprises 40 mg of trospium chloride, as Component (a); and 1 mg of granisetron (as hydrochloride), as Component (b), wherein Components (a) and (b) are mixed together and with a pharmaceutical carrier in an IR formulation.

A second particularly advantageous trospium/granisetron composition according to this embodiment comprises 60 mg of trospium chloride, as Component (a); and 1 mg of granisetron (as hydrochloride), as Component (b), as mixed together and with a pharmaceutical carrier in an IR formulation.

A third advantageous trospium/granisetron composition according to this embodiment comprises 65 mg of trospium chloride, as Component (a); and 1 mg of granisetron (as hydrochloride), as Component (b), as mixed together and with a pharmaceutical carrier in an IR formulation.

A fourth advantageous trospium/granisetron composition according to this embodiment comprises 80 mg of trospium chloride, as Component (a); and 1 mg of granisetron (as hydrochloride), as Component (b), as mixed together and with a pharmaceutical carrier in an IR formulation.

A fifth advantageous trospium/granisetron composition according to this embodiment comprises 80 mg of trospium chloride, as Component (a); and 2 mg of granisetron (as hydrochloride), as Component (b), as mixed together and with a pharmaceutical carrier in an IR formulation.

A sixth advantageous trospium/granisetron composition according to this embodiment comprises 100 mg of trospium chloride, as Component (a); and 2 mg of granisetron (as hydrochloride), as Component (b), as mixed together and with a pharmaceutical carrier in an IR formulation.

A seventh advantageous trospium/granisetron composition according to this embodiment comprises 160 mg of trospium chloride, as Component (a); and 3 mg of granisetron (as hydrochloride), as Component (b), as mixed together and with a pharmaceutical carrier in an IR formulation.

An advantageous trospium/ondansetron composition according to this embodiment comprises from 20 mg to 160 mg of trospium chloride, as Component (a); and from 4 mg to 24 mg of ondansetron (as hydrochloride dihydrate);

as mixed together and with a pharmaceutical carrier in an IR formulation.

A first particularly advantageous trospium/ondansetron composition according to this embodiment comprises 40 mg of trospium chloride, as Component (a); and 4 mg of ondansetron (as hydrochloride dihydrate), as Component (b), as mixed together and with a pharmaceutical carrier in an IR formulation.

A second particularly advantageous trospium/ondansetron composition according to this embodiment comprises 60 mg of trospium chloride, as Component (a); and 4 mg of ondansetron (as hydrochloride dihydrate), as Component (b), as mixed together and with a pharmaceutical carrier in an IR formulation.

A third advantageous trospium/ondansetron composition according to this embodiment comprises
- 80 mg of trospium chloride, as Component (a); and
- 4 mg of ondansetron (as hydrochloride dihydrate), as Component (b), as mixed together and with a pharmaceutical carrier in an IR formulation.

A fourth advantageous trospium/ondansetron composition according to this embodiment comprises
- 100 mg of trospium chloride, as Component (a); and
- 8 mg of ondansetron (as hydrochloride dihydrate), as Component (b), as mixed together and with a pharmaceutical carrier in an IR formulation.

A fifth advantageous trospium/ondansetron composition according to this embodiment comprises
- 120 mg of trospium chloride, as Component (a); and
- 8 mg of ondansetron (as hydrochloride dihydrate), as Component (b), as mixed together and with a pharmaceutical carrier in an IR formulation.

An advantageous trospium/tropisetron composition according to this embodiment comprises
- from 20 mg to 160 mg of trospium chloride, as Component (a); and
- from 5 mg to 15 mg of tropisetron (as hydrochloride), as Component (b);

as mixed together and with a pharmaceutical carrier in an IR formulation.

A first particularly advantageous trospium/tropisetron composition according to this embodiment comprises
- 40 mg of trospium chloride, as Component (a); and
- 5 mg of tropisetron (as hydrochloride), as Component (b), as mixed together and with a pharmaceutical carrier in an IR formulation.

A second particularly advantageous trospium/tropisetron composition according to this embodiment comprises
- 60 mg of trospium chloride, as Component (a); and
- 5 mg of tropisetron (as hydrochloride), as Component (b), as mixed together and with a pharmaceutical carrier in an IR formulation.

A third advantageous trospium/tropisetron composition according to this embodiment comprises
- 140 mg of trospium chloride, as Component (a); and
- 10 mg of tropisetron (as hydrochloride), as Component (b), as mixed together and with a pharmaceutical carrier in an IR formulation.

An advantageous trospium/domperidone composition according to this embodiment comprises
- from 20 mg to 160 mg of trospium chloride, as Component (a); and
- from 10 mg to 30 mg of domperidone, as Component (b);

as mixed together and with a pharmaceutical carrier in an IR formulation.

A first particularly advantageous trospium/domperidone composition according to this embodiment comprises
- 40 mg of trospium chloride, as Component (a); and
- 10 mg of domperidone, as Component (b), as mixed together and with a pharmaceutical carrier in an IR formulation.

A second particularly advantageous trospium/domperidone composition according to this embodiment comprises
- 70 mg of trospium chloride, as Component (a); and
- 10 mg of domperidone, as Component (b), as mixed together and with a pharmaceutical carrier in an IR formulation.

A third advantageous trospium/domperidone composition according to this embodiment comprises
- 140 mg of trospium chloride, as Component (a); and
- 20 mg of domperidone, as Component (b), as mixed together and with a pharmaceutical carrier in an IR formulation.

A fourth advantageous trospium/domperidone composition according to this embodiment comprises
- 160 mg of trospium chloride, as Component (a); and
- 30 mg of domperidone, as Component (b), as mixed together and with a pharmaceutical carrier in an IR formulation.

An advantageous trospium/metoclopramide composition according to this embodiment comprises
- from 20 mg to 160 mg of trospium chloride, as Component (a); and
- from 10 mg to 30 mg of metoclopramide (as monohydrochloride monohydrate), as Component (b);

as mixed together and with a pharmaceutical carrier in an IR formulation.

A first particularly advantageous trospium/domperidone composition according to this embodiment comprises
- 40 mg of trospium chloride, as Component (a); and
- 10 mg of metoclopramide (as monohydrochloride monohydrate), as Component (b), as mixed together and with a pharmaceutical carrier in an IR formulation.

A second particularly advantageous trospium/metoclopramide composition according to this embodiment comprises
- 60 mg of trospium chloride, as Component (a); and
- 10 mg of metoclopramide (as monohydrochloride monohydrate), as Component (b), as mixed together and with a pharmaceutical carrier in an IR formulation.

A third advantageous trospium/metoclopramide composition according to this embodiment comprises
- 100 mg of trospium chloride, as Component (a); and
- 20 mg of metoclopramide (as monohydrochloride monohydrate), as Component (b), as mixed together and with a pharmaceutical carrier in an IR formulation.

A fourth advantageous trospium/metoclopramide composition according to this embodiment comprises
- 160 mg of trospium chloride, as Component (a); and
- 30 mg of metoclopramide (as monohydrochloride monohydrate), as Component (b), as mixed together and with a pharmaceutical carrier in an IR formulation.

An advantageous glycopyrrolium/granisetron composition according to this embodiment comprises
- from 2 mg to 16 mg of glycopyrrolium bromide, as Component (a); and
- from 1 mg to 3 mg of granisetron (as hydrochloride);

as mixed together and with a pharmaceutical carrier in an IR formulation.

A first particularly advantageous glycopyrronium/granisetron composition comprises
- 2 mg of glycopyrrolium bromide, as Component (a); and
- 1 mg of granisetron (as hydrochloride), as Component (b), as mixed together and with a pharmaceutical carrier in an IR formulation.

A second particularly advantageous glycopyrrolium/granisetron composition according to this embodiment comprises
- 2.5 mg of glycopyrrolium bromide, as Component (a); and
- 1 mg of granisetron (as hydrochloride), as Component (b), as mixed together and with a pharmaceutical carrier in an IR formulation.

A third advantageous glycopyrrolium/granisetron composition according to this embodiment comprises
- 3 mg of glycopyrrolium bromide, as Component (a); and
- 1 mg of granisetron (as hydrochloride), as Component (b), as mixed together and with a pharmaceutical carrier in an IR formulation.

A fourth advantageous glycopyrrolium/granisetron composition according to this embodiment comprises
- 5 mg of glycopyrrolium bromide, as Component (a); and
- 1 mg of granisetron (as hydrochloride), as Component (b), as mixed together and with a pharmaceutical carrier in an IR formulation.

A fifth advantageous glycopyrrolium/granisetron composition according to this embodiment comprises
- 10 mg of glycopyrrolium bromide, as Component (a); and
- 2 mg of granisetron (as hydrochloride), as Component (b), as mixed together and with a pharmaceutical carrier in an IR formulation.

A sixth advantageous glycopyrrolium/granisetron composition according to this embodiment comprises
- 12 mg of glycopyrrolium bromide, as Component (a); and
- 2 mg of granisetron (as hydrochloride), as Component (b), as mixed together and with a pharmaceutical carrier in an IR formulation.

A seventh advantageous glycopyrrolium/granisetron composition according to this embodiment comprises
- 16 mg of glycopyrrolium bromide, as Component (a); and
- 3 mg of granisetron (as hydrochloride), as Component (b), as mixed together and with a pharmaceutical carrier in an IR formulation.

An advantageous glycopyrrolium/ondansetron composition according to this embodiment comprises
- from 2 mg to 16 mg of glycopyrrolium bromide, as Component (a); and
- from 4 mg to 24 mg of ondansetron (as hydrochloride dihydrate);

as mixed together and with a pharmaceutical carrier in an IR formulation.

A first particularly advantageous glycopyrrolium/ondansetron composition according to this embodiment comprises
- 2 mg of glycopyrrolium bromide, as Component (a); and
- 4 mg of ondansetron (as hydrochloride dihydrate), as Component (b), as mixed together and with a pharmaceutical carrier in an IR formulation.

A second particularly advantageous glycopyrrolium/ondansetron composition according to this embodiment comprises
- 3 mg of glycopyrrolium bromide, as Component (a); and
- 4 mg of ondansetron (as hydrochloride dihydrate), as Component (b), as mixed together and with a pharmaceutical carrier in an IR formulation.

A third advantageous glycopyrrolium/ondansetron composition according to this embodiment comprises
- 4 mg of glycopyrrolium bromide, as Component (a); and
- 4 mg of ondansetron (as hydrochloride dihydrate), as Component (b), as mixed together and with a pharmaceutical carrier in an IR formulation.

A fourth advantageous glycopyrrolium/ondansetron composition according to this embodiment comprises
- 8 mg of glycopyrrolium bromide, as Component (a); and
- 8 mg of ondansetron (as hydrochloride dihydrate), as Component (b), as mixed together and with a pharmaceutical carrier in an IR formulation.

A fifth advantageous glycopyrrolium/ondansetron composition according to this embodiment comprises
- 10 mg of glycopyrrolium bromide, as Component (a); and
- 12 mg of ondansetron (as hydrochloride dihydrate), as Component (b), as mixed together and with a pharmaceutical carrier in an IR formulation.

A sixth advantageous glycopyrrolium/ondansetron composition according to this embodiment comprises
- 12 mg of glycopyrrolium bromide, as Component (a); and
- 16 mg of ondansetron (as hydrochloride dihydrate), as Component (b), as mixed together and with a pharmaceutical carrier in an IR formulation.

A seventh advantageous glycopyrrolium/ondansetron composition according to this embodiment comprises
- 16 mg of glycopyrrolium bromide, as Component (a); and
- 20 mg of ondansetron (as hydrochloride dihydrate), as Component (b), as mixed together and with a pharmaceutical carrier in an IR formulation.

An advantageous glycopyrrolium/tropisetron composition according to this embodiment comprises
- from 2 mg to 16 mg of glycopyrrolium bromide, as Component (a); and
- from 5 mg to 15 mg of tropisetron (as hydrochloride), as Component (b);

as mixed together and with a pharmaceutical carrier in an IR formulation.

A first particularly advantageous glycopyrrolium/tropisetron composition according to this embodiment comprises
- 2.5 mg of glycopyrrolium bromide, as Component (a); and
- 5 mg of tropisetron (as hydrochloride), as Component (b), as mixed together and with a pharmaceutical carrier in an IR formulation.

A second particularly advantageous glycopyrrolium/tropisetron composition according to this embodiment comprises
- 4 mg of glycopyrrolium bromide, as Component (a); and
- 5 mg of tropisetron (as hydrochloride), as Component (b), as mixed together and with a pharmaceutical carrier in an IR formulation.

A third advantageous glycopyrrolium/tropisetron composition according to this embodiment comprises
- 10 mg of glycopyrrolium bromide, as Component (a); and
- 10 mg of tropisetron (as hydrochloride), as Component (b), as mixed together and with a pharmaceutical carrier in an IR formulation.

An advantageous glycopyrrolium/alosetron composition according to this embodiment comprises
- from 2.1 mg to 16 mg of glycopyrrolium bromide, as Component (a); and
- from 0.5 mg to 3 mg of alosetron (as hydrochloride), as Component (b);

as mixed together and with a pharmaceutical carrier in an IR formulation.

A particular advantageous glycopyrrolium/alosetron composition according to this embodiment comprises 2.5 mg of glycopyrrolium bromide, as Component (a); and 2 mg of alosetron (as hydrochloride), as Component (b); as mixed together and with a pharmaceutical carrier in an IR formulation.

An advantageous glycopyrrolium/domperidone composition according to this embodiment comprises from 4 mg to 16 mg of glycopyrrolium bromide, as Component (a); and from 10 mg to 30 mg of domperidone, as Component (b); as mixed together and with a pharmaceutical carrier in an IR formulation.

A first particularly advantageous glycopyrrolium/domperidone composition according to this embodiment comprises 4 mg of glycopyrrolium bromide, as Component (a); and 10 mg of domperidone, as Component (b), as mixed together and with a pharmaceutical carrier in an IR formulation.

A second particularly advantageous glycopyrrolium/domperidone composition according to this embodiment comprises 8 mg of glycopyrrolium bromide, as Component (a); and 10 mg of domperidone, as Component (b), as mixed together and with a pharmaceutical carrier in an IR formulation.

A third advantageous glycopyrrolium/domperidone composition according to this embodiment comprises 8 mg of glycopyrrolium bromide, as Component (a); and 20 mg of domperidone, as Component (b), as mixed together and with a pharmaceutical carrier in an IR formulation.

A fourth advantageous glycopyrrolium/domperidone composition according to this embodiment comprises 10 mg of glycopyrrolium bromide, as Component (a); and 30 mg of domperidone, as Component (b), as mixed together and with a pharmaceutical carrier in an IR formulation.

An advantageous glycopyrrolium/metoclopramide composition according to this embodiment comprises from 4 mg to 16 mg of glycopyrrolium bromide, as Component (a); and from 10 mg to 30 mg of metoclopramide (as monohydrochloride monohydrate), as Component (b);

as mixed together and with a pharmaceutical carrier in an IR formulation.

A first particularly advantageous glycopyrrolium/metoclopramide composition according to this embodiment comprises 4 mg of glycopyrrolium bromide, as Component (a); and 10 mg of metoclopramide (as monohydrochloride monohydrate), as Component (b), as mixed together and with a pharmaceutical carrier in an IR formulation.

A second particularly advantageous glycopyrrolium/metoclopramide composition according to this embodiment comprises 8 mg of glycopyrrolium bromide, as Component (a); and 10 mg of metoclopramide (as monohydrochloride monohydrate), as Component (b), as mixed together and with a pharmaceutical carrier in an IR formulation.

A third advantageous glycopyrrolium/metoclopramide composition according to this embodiment comprises 8 mg of glycopyrrolium bromide, as Component (a); and 20 mg of metoclopramide (as monohydrochloride monohydrate), as Component (b), as mixed together and with a pharmaceutical carrier in an IR formulation.

A fourth advantageous glycopyrrolium/metoclopramide composition according to this embodiment comprises 10 mg of glycopyrrolium bromide, as Component (a); and 30 mg of metoclopramide (as monohydrochloride monohydrate), as Component (b), as mixed together and with a pharmaceutical carrier in an IR formulation.

According to a second embodiment, the compositions of the present invention are formulated by mixing a nsPAChA selected from the group consisting of propiverine hydrochloride, trospium chloride and glycopyrrolium bromide, as the Component (a) with a pharmaceutical carrier for an immediate or extended release in tablets (Tablet A) and the naAEA Component (b), separately, with a pharmaceutical carrier for an immediate or extended release in tablets (Tablet B) and introducing Tablet A and Tablet B in a capsule for oral administration as described for example in GB 1204580 or in US 2007/0224259, thus obtaining a unit form to be administered to a patient suffering from a dementia of Alzheimer type.

An advantageous propiverine/granisetron unit form according to this embodiment consists of preferably hard gelatin capsules each containing Tablet A comprising from 15 mg to 120 mg of propiverine hydrochloride, as Component (a), in admixture with a pharmaceutical carrier in a IR formulation; and Tablet B, comprising from 1 to 3 mg of granisetron (as hydrochloride), as Component (b), in admixture with a pharmaceutical carrier in an IR-formulation.

A first particularly advantageous propiverine/granisetron unit form according to this embodiment contains Tablet A comprising 15 mg of propiverine hydrochloride, as Component (a), in admixture with a pharmaceutical carrier in a IR formulation; and Tablet B, comprising 1 mg of granisetron (as hydrochloride), as Component (b), in admixture with a pharmaceutical carrier in an IR-formulation.

A second particularly advantageous propiverine/granisetron unit form according to this embodiment contains Tablet A comprising 30 mg of propiverine hydrochloride, as Component (a), in admixture with a pharmaceutical carrier in a IR formulation; and Tablet B, comprising 2 mg of granisetron (as hydrochloride), as Component (b), in admixture with a pharmaceutical carrier in an IR-formulation.

A third advantageous propiverine/granisetron unit form according to this embodiment contains Tablet A comprising 45 mg of propiverine hydrochloride, as Component (a), in admixture with a pharmaceutical carrier in a IR formulation; and Tablet B, comprising 3 mg of granisetron (as hydrochloride), as Component (b), in admixture with a pharmaceutical carrier in an IR-formulation.

An advantageous propiverine/ondansetron unit form according to this embodiment consists of preferably hard gelatin capsules each containing Tablet A comprising from 15 mg to 120 mg of propiverine hydrochloride, as Component (a), in admixture with a pharmaceutical carrier in a IR formulation; and Tablet B, comprising from 4 to 24 mg of ondansetron (as hydrochloride dihydrate), as Component (b), in admixture with a pharmaceutical carrier in an IR-formulation.

A first particularly advantageous propiverine/ondansetron unit form according to this embodiment contains Tablet A comprising 15 mg of propiverine hydrochloride, as Component (a), in admixture with a pharmaceutical carrier in a IR formulation; and Tablet B, comprising 4 mg of ondansetron (as hydrochloride dihydrate), as Component (b), in admixture with a pharmaceutical carrier in an IR-formulation.

A second particularly advantageous propiverine/ondansetron unit form according to this embodiment contains Tablet A comprising 30 mg of propiverine hydrochloride, as Component (a), in admixture with a pharmaceutical carrier in a IR formulation; and Tablet B, comprising 8 mg of ondansetron (as hydrochloride dihydrate), as Component (b), in admixture with a pharmaceutical carrier in an IR-formulation.

A third advantageous propiverine/ondansetron unit form according to this embodiment contains Tablet A comprising 45 mg of propiverine hydrochloride, as Component (a), in admixture with a pharmaceutical carrier in a IR formulation; and Tablet B, comprising 8 mg of ondansetron (as hydrochloride dihydrate), as Component (b), in admixture with a pharmaceutical carrier in an IR-formulation.

An advantageous propiverine/tropisetron unit form according to this embodiment consists of preferably hard gelatin capsules each containing Tablet A comprising from 15 mg to 120 mg of propiverine hydrochloride, as Component (a), in admixture with a pharmaceutical carrier in a IR formulation; and Tablet B, comprising from 5 to 15 mg of tropisetron as Component (b), in admixture with a pharmaceutical carrier in an IR-formulation.

A first particularly advantageous propiverine/tropisetron unit form according to this embodiment contains Tablet A comprising 15 mg of propiverine hydrochloride, as Component (a), in admixture with a pharmaceutical carrier in an IR formulation; and Tablet B, comprising 5 mg of tropisetron (as hydrochloride), as Component (b), in admixture with a pharmaceutical carrier in an IR-formulation.

A second particularly advantageous propiverine/tropisetron unit form according to this embodiment contains Tablet A comprising 31 mg of propiverine hydrochloride, as Component (a), in admixture with a pharmaceutical carrier in a IR formulation; and Tablet B, comprising 5 mg of tropisetron (as hydrochloride), as Component (b), in admixture with a pharmaceutical carrier in an IR-formulation.

An advantageous propiverine/domperidone unit form according to this embodiment consists of preferably hard gelatin capsules each containing Tablet A comprising from 15 mg to 120 mg of propiverine hydrochloride, as Component (a), in admixture with a pharmaceutical carrier in a IR formulation; and Tablet B, comprising from 10 to 30 mg of domperidone as Component (b), in admixture with a pharmaceutical carrier in an IR-formulation.

A particularly advantageous propiverine/domperidone unit form according to this embodiment contains Tablet A comprising 31 mg of propiverine hydrochloride, as Component (a), in admixture with a pharmaceutical carrier in a IR formulation; and Tablet B, comprising 10 mg of domperidone as Component (b), in admixture with a pharmaceutical carrier in an IR-formulation.

An advantageous propiverine/metoclopramide unit form according to this embodiment consists of preferably hard gelatin capsules each containing Tablet A comprising from 15 mg to 120 mg of propiverine hydrochloride, as Component (a), in admixture with a pharmaceutical carrier in a IR formulation; and Tablet B, comprising from 10 to 30 mg of metoclopramide (as monohydrochloride monohydrate) as Component (b), in admixture with a pharmaceutical carrier in an IR-formulation.

A particularly advantageous propiverine/metoclopramide unit form according to this embodiment contains Tablet A comprising 20 mg of propiverine hydrochloride, as Component (a), in admixture with a pharmaceutical carrier in a IR formulation; and Tablet B, comprising 15 mg of metoclopramide (as monohydrochloride monohydrate) as Component (b), in admixture with a pharmaceutical carrier in an IR-formulation.

According to a third embodiment, the compositions according to the present invention are formulated in a di-layer tablet, one comprising a nsPAChA selected from the group consisting of propiverine hydrochloride, trospium chloride and glycopyrrolium bromide and the other comprising a naAEA, which releases the two drug doses, in which the release of a drug from one drug-containing layer does not interfere with the release of a drug from the other drug-containing layer as described for example in WO 2006/089493.

An advantageous propiverine/granisetron composition according to this embodiment consists of Layer A, comprising from 15 mg to 120 mg of propiverine hydrochloride, as Component (a), in admixture with a pharmaceutical carrier in a IR formulation and Layer B, comprising from 1 to 3 mg of granisetron, as hydrochloride, as Component (b), in admixture with a pharmaceutical carrier in an IR-formulation.

A first particularly advantageous propiverine/granisetron composition according to this embodiment consist of Layer A, comprising 25 mg of propiverine hydrochloride, as Component (a), in admixture with a pharmaceutical carrier in a IR formulation and Layer B, comprising 1 mg of granisetron, as hydrochloride, as Component (b), in admixture with a pharmaceutical carrier in an IR-formulation.

A second particularly advantageous propiverine/granisetron composition according to this embodiment consist of Layer A, comprising 31 mg of propiverine hydrochloride, as Component (a), in admixture with a pharmaceutical carrier in a IR formulation and Layer B, comprising 2 mg of granisetron, as hydrochloride, as Component (b), in admixture with a pharmaceutical carrier in an IR-formulation.

A third particularly advantageous propiverine/granisetron composition according to this embodiment consist of Layer A, comprising 40 mg of propiverine hydrochloride, as Component (a), in admixture with a pharmaceutical carrier in a IR formulation and Layer B, comprising 2 mg of granisetron, as hydrochloride, as Component (b), in admixture with a pharmaceutical carrier in an IR-formulation.

An advantageous propiverine/ondansetron composition according to this embodiment consists of Layer A, comprising from 15 mg to 120 mg of propiverine hydrochloride, as Component (a), in admixture with a pharmaceutical carrier in a IR formulation and Layer B, comprising from 4 to 24 mg of ondansetron, as hydrochloride dihydrate, as Component (b), in admixture with a pharmaceutical carrier in an IR-formulation.

A first particularly advantageous propiverine/ondansetron composition according to this embodiment consist of Layer A, comprising 15 mg of propiverine hydrochloride, as Component (a), in admixture with a pharmaceutical carrier in a IR formulation and Layer B, comprising 4 mg of ondansetron, as hydrochloride dihydrate, as Component (b), in admixture with a pharmaceutical carrier in an IR-formulation.

A second particularly advantageous propiverine/ondansetron composition according to this embodiment consist of Layer A, comprising 50 mg of propiverine hydrochloride, as Component (a), in admixture with a pharmaceutical carrier in a IR formulation and Layer B, comprising 8 mg of ondansetron, as hydrochloride dihydrate, as Component (b), in admixture with a pharmaceutical carrier in an IR-formulation.

An advantageous propiverine/tropisetron composition according to this embodiment consists of Layer A, comprising from 15 mg to 120 mg propiverine hydrochloride, as Component (a), in admixture with a pharmaceutical carrier in a IR formulation and Layer B, comprising from 5 to 15 mg of tropisetron, as hydrochloride, as Component (b), in admixture with a pharmaceutical carrier in an IR-formulation.

A particularly advantageous propiverine/tropisetron composition according to this embodiment consist of Layer A, comprising 31 mg of propiverine hydrochloride, as Component (a), in admixture with a pharmaceutical carrier in a IR formulation and Layer B, comprising 5 mg of tropisetron, as hydrochloride, as Component (b), in admixture with a pharmaceutical carrier in an IR-formulation.

An advantageous propiverine/domperidone composition according to this embodiment consists of Layer A, comprising from 15 mg to 120 mg of propiverine hydrochloride, as Component (a), in admixture with a pharmaceutical carrier in a IR formulation and Layer B, comprising from 10 to 30 mg of domperidone, as Component (b), in admixture with a pharmaceutical carrier in an IR-formulation.

A particularly advantageous propiverine/domperidone composition according to this embodiment consists of Layer A, comprising 31 mg of propiverine hydrochloride, as Component (a), in admixture with a pharmaceutical carrier in a IR formulation and Layer B, comprising 10 mg of domperidone, as Component (b), in admixture with a pharmaceutical carrier in an IR-formulation.

An advantageous propiverine/metoclopramide composition according to this embodiment consists of Layer A, comprising from 15 mg to 120 mg of propiverine hydrochloride, as Component (a), in admixture with a pharmaceutical carrier in a IR formulation and Layer B, comprising from 10 to 30 mg of metoclopramide, as monohydrochloride hydrate, as Component (b), in admixture with a pharmaceutical carrier in an IR-formulation.

A particularly advantageous propiverine/metoclopramide composition according to this embodiment consist of Layer A, comprising 31 mg of propiverine hydrochloride, as Component (a), in admixture with a pharmaceutical carrier in a IR formulation and Layer B, comprising 10 mg of metoclopramide (as monohydrochloride monohydrate) as Component (b), in admixture with a pharmaceutical carrier in an IR-formulation.

The above combined pharmaceutical compositions are able to assure greater and longer efficacy and less adverse effects of co-administered AChEIs by allowing the safe and tolerable administration of larger and thus more therapeutically effective quantities (from 2.5 to 7 times the maximum recommended doses) of said AChEIs in human subjects treated with said AChEI. In particular, by inducing very high blood levels in human subjects, the above combined compositions assure an increased concentration of AChEIs to the CNS of patients suffering from a dementia of Alzheimer type which are treated even with very high doses of AChEI.

The pathologic conditions treated with the composition of the present invention include, but are not limited to, Alzheimer's disease, Parkinson's disease dementia, and other chronic disorders of human cognitive and neurobehavioral function that are treated, in part, by pharmaceuticals intended to augment brain acetylcholine-mediated neurotransmission. The composition of the present invention can also be used to treat acute cognitive disorders such as post-surgical delirium.

The therapeutic efficacy is measured by the degree to which cognitive and other neurobehavioral disabilities associated with dementias of the Alzheimer type, as documented by the use of standard scales, are reduced.

Thus, the present invention also provides a method for inducing neuroprotection, thus combating neurodegeneration, and consequently slowing disease progression in a patient suffering from a dementia of the Alzheimer type, which comprises administering to said patient an AChEI daily dose which is at least 2.5, up to 7 times the maximum recommended daily dose of said AChEI used in the treatment of Alzheimer type dementias, in combination with a pharmaceutical composition comprising an nsPAChA selected from the group consisting of propiverine hydrochloride, in an amount of from 15 mg to 240 mg, advantageously from 30 mg to 240 mg, preferably from 31 mg to 240 mg; trospium chloride, in an amount of from 20 mg to 480 mg, advantageously from 40 mg to 480 mg, preferably from 61 mg to 480 mg; and glycopyrrolium bromide, in an amount of from 2 mg to 16 mg, advantageously from 4 mg to 16 mg, preferably from 4.1 to 16 mg; and (b) a non-anticholinergic antiemetic agent (naAEA); in admixture with a pharmaceutical carrier. Said pharmaceutical composition is exhaustively illustrated herein above.

II. Second Aspect of the Present Invention

In a second aspect, the present invention provides an improved method to augment and extend the efficacy of current cholinergic therapies for Alzheimer type dementias by mitigating the common dose-limiting adverse events of cholinomimetic treatments of said Alzheimer type dementias that arise as a result of the concomitant excessive stimulation of cholinergic receptors in the PNS. Drugs that act to selectively inhibit the activation of all or nearly all the muscarinic receptors in the PNS, but not in the CNS, resulting from cholinomimetic therapy have the potential to reduce the adverse effects, such that higher cholinomimetic doses can be administered leading to greater and more prolonged antidementia efficacy with fewer peripherally mediated side effects. By combining an extended release cholinomimetic with a peripheral anticholinergic having an advantageous duration of pharmacologic action, in a single dosage form, the benefits to patients of an even longer duration of action is also achieved.

In particular, the invention provides a method for inducing neuroprotection in a patient suffering from an Alzheimer type dementia, which comprises administering said patient an AChEI dose which is at least 2.5, up to 7 times the dose used in the treatment of Alzheimer type dementias, in combination with a nsPAChA dose which is more than twice, up to 8 times the dose used in the anticholinergic therapy.

More particularly, the invention provides a method for inducing neuroprotection in a patient suffering from an Alzheimer type dementia, which comprises administering to said patient a nsPAChA selected from the group consisting of solifenacin, pharmaceutically acceptable salts and compounds of solifenacin, pharmaceutically acceptable salts of trospium, pharmaceutically acceptable salts of glycopyrrolium, propiverine and pharmaceutically acceptable salts of propiverine, said nsPAChA being administered at a dose which is more than twice to eight times, preferably from 2.5 to 8 times the dose used for the anticholinergic therapy, in combination with a dose of said AChEI which is from 2.5 to 7 times the dose used for the treatment of Alzheimer type dementia. The pharmaceutically acceptable salts of propiverine and solifenacin include the propiverine and solifenacin quaternary salts, in particular the methyl chloride, the methyl iodide and the methyl bromide thereof.

This finding is surprising because an increase in the blood levels of a drug normally also increases the risk of side effects while, in the case of the combined nsPAChA/AChEI treatment according to the present invention, the most common and dangerous adverse effects are suppressed.

The present invention also provides a pharmaceutical composition comprising, as an active ingredient, an nsPAChA selected from the group consisting of solifenacin and pharmaceutically acceptable salts thereof, propiverine and pharmaceutically acceptable salts thereof, and trospium pharmaceutically acceptable salts, in an amount which is from more than 200% to 800% the maximum amount of said nsPAChA contained in compositions indicated for the anticholinergic therapy. This composition is useful for inducing neuroprotection and combating neurodegeneration in a patient suffering from Alzheimer type dementia, who is treated with an AChEI dose which is from 250% to 700% the maximum recommended dose of said AChEI.

A. The nsPAChAs

Advantageously, the used nsPAChAs are quaternary ammonium nsPAChAs, sulfonium nsPAChAs, (1S)-(3R)-1-azabicyclo[2.2.2]oct-3-yl 3,4-dihydro-1-phenyl-2(1H)-isoquinolinecarboxylate (solifenacin) and its pharmaceutically acceptable salts, (1-methylpiperidin-4-yl) 2,2-di(phenyl)-2-propoxyacetate (propiverine) and its pharmaceutically acceptable salts, 1,4,5,6-tetrahydro-1-methylpyrimidin-2-yl methyl α-cyclohexyl-α-hydroxy-α-phenylacetate (oxyphencyclimine) and its pharmaceutically acceptable salts, (R)—N,N-diisopropyl-3-(2-hydroxy-5-methylphenyl)-3-phenylpropanamine (tolterodine) and its pharmaceutically acceptable salts. Said nsPAChAs, preferably, are compounds with duration of action of at least 6 hours, advantageously from 8 to 24 hours, more advantageously from 10 to 24 hours, preferably from 12 to 24 hours, even though nsPAChAs having an appropriate duration of action corresponding to the duration of action of the concomitantly administered AChEI may be successfully used.

Particularly advantageous quaternary ammonium nsPAChAs or sulfonium nsPAChAs are compounds of formula II

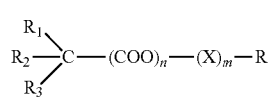

(II)

wherein
R is a radical selected from the group consisting of those of formulas (a)-(e)

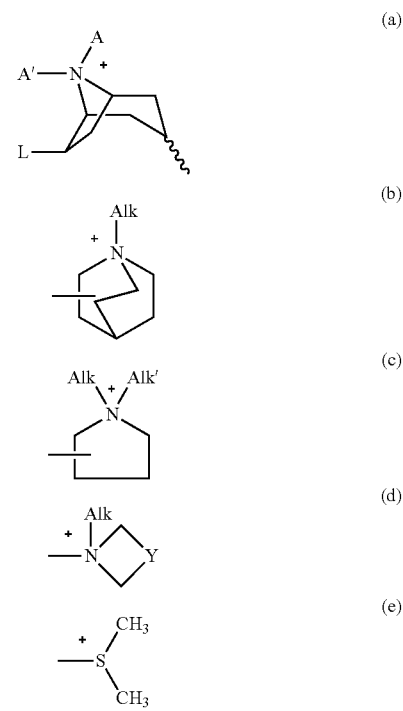

A being methyl and A' being $(C_1-C_4)$alkyl or 2-fluoroethyl group or A and A' forming a 1,4-butylene or 1,5-pentylene chain, L being hydrogen or methoxy, Alk and Alk' each being $(C_1-C_4)$alkyl and Y being a bivalent radical selected from the group consisting of 1,2-ethylene, 1,3-propylene, 1,4-butylene and 2-oxa-1,3-propylene; the corresponding counter ion being a pharmaceutically acceptable anion, such as a chloro, bromo, iodo, tartrate, hydrogen tartrate, succinate, maleate, fumarate, sulfate, hydrogen sulfate or methylsulfate anion;

n and m, independently, are zero or 1;

X is a $(C_2-C_3)$alkylene group;

$R_1$ and $R_2$ are each phenyl, cyclopentyl, cyclohexyl, 1-cyclohexenyl, 2-thienyl and, when R is a radical (a), also each represents $(C_1-C_4)$alkyl;

$R_3$ is H or OH or, only when R is a radical (a), also a COOAlk group, Alk being a $(C_1-C_4)$alkyl group.

Exemplary nsPAChAs of formula II above used for preparing medicaments for the treatment of Alzheimer type dementia in combination with AchEIs are anisotropine methylbromide [R=(a), A=A'=CH$_3$, L=H; n=1; m=0; $R_1$=$R_2$=n-C$_3$H$_7$; $R_3$=H;];

ciclotropium bromide [R=(a), A=CH$_3$, A'=isopropyl, L=H; n=1; m=0; $R_1$=phenyl; $R_2$=cyclopentyl; $R_3$=H];

flutropium bromide [R=(a), A=CH$_3$, A'=2-fluoroethyl, L=H; n=1; m=0; $R_1$=$R_2$=phenyl; $R_3$=OH];

homatropine methylbromide [R=(a), A=A'=CH$_3$, L=H; n=1; m=0; $R_1$=phenyl; $R_2$=$R_3$=H];

sintropium bromide; [R=(a), A=CH$_3$, A'=isopropyl, L=H; n=1; m=0; ; $R_1$=$R_2$=n-C$_3$H$_7$; $R_3$=H];

tematropium metilsulfate [R=(a), A=A'=CH$_3$, L=H; n=1; m=0; $R_1$=phenyl; $R_2$=COOC$_2$H$_5$; $R_3$=H];

tropenziline bromide [R=(a), A=A'=CH₃, L=methoxy; n=1; m=0; R₁=R₂=phenyl, R₃=OH];
trospium chloride [R=(a), A+A'=1,4-butylene, L=H; n=1; m=0; R₁=R₂=phenyl; R₃=OH];
clidinium bromide [R=(b)-3-, Alk=methyl; n=1; m=0; R₁=R₂=phenyl; R₃=OH];
droclidinium bromide [R=(b)-3-, Alk=methyl; n=1; m=0; R₁=phenyl; R₂=cyclopentyl; R₃=OH];
benzilonium bromide [R=(c)-3-, both Alk and Alk'=ethyl; n=1; m=0; R₁=R₂=phenyl; R₃—OH];
benzopyrronium bromide [R=(c)-3-, both Alk and Alk'=methyl; n=1; m=0; R₁=R₂=phenyl; R₃=OH];
cyclopyrronium bromide [R=(c)-3-, Alk=methyl and Alk'=ethyl; n=1; m=0; R₁=phenyl; R₂=cyclopentyl; R₃=H];
glycopyrronium bromide (glycopyrrolate) [R=(c)-3-, both Alk and Alk'=methyl; n=1; m=0; R₁=phenyl; R₂=cyclopentyl; R₃=H];
heteronium bromide [R=(c)-3-, both Alk and Alk'=methyl n=1; m=0; R₁=phenyl; R₂=2-thienyl; R₃=OH];
hexopyrronium bromide [R=(c)-3-, both Alk and Alk'=methyl; n=1; m=0; R₁=phenyl; R₂=cyclohexyl; R₃=H];
oxypyrronium bromide [R=(c)-2-, both Alk and Alk'=methyl; n=1; m=1; X=1,2-ethylene; R₁=phenyl; R₂=cyclohexyl; R₃=OH];
ritropirronium bromide [R=(c)-3-, both Alk and Alk'=methyl; n=1; m=0; R₁=phenyl; R₂=cyclopentyl; R₃=OH];
etipirium iodide [R=(d), Alk=methyl, Y=1,2-ethylene; n=1; m=1; X=1,2-ethylene; R₁=R₂=phenyl; R₃=OH];
fenclexonium methylsulfate [R=(d), Alk=CH₃, Y=1,3-propylene; n=0; m=1; X=1,2-ethylene; R₁=phenyl; R₂=1-cyclohexenyl; R₃=H];
tricyclamol chloride (procyclidine methochloride) [R=(d), Alk=methyl, Y=1,2-ethylene; n=0; m=1; X=1,2-ethylene; R₁=phenyl; R₂=cyclohexyl; R₃=OH];
tiemonium iodide [R=(d), Alk=methyl, Y=2-oxa-1,3-propylene; n=0; m=1; X=1,2-ethylene; R₁=phenyl; R₂=2-thienyl; R₃=OH];
hexasonium iodide [R=(e); n=1; m=1; X=1,2-ethylene; R₁=phenyl; R₂=cyclohexyl; R₃=H]; and
oxysonium iodide [R=(e); n=1; m=1; X=1,2-ethylene; R₁=phenyl; R₂=cyclohexyl; R₃=OH.

A nsPAChA selected from the group consisting of (1S)-(3R)-1-azabicyclo[2.2.2]oct-3-yl 3,4-dihydro-1-phenyl-2(1H)-isoquinolinecarboxylate (solifenacin) or a pharmaceutically acceptable salt or compound thereof, 1-methyl-4-[(2,2-diphenyl-2-n-propoxy)acetoxy]piperidine (propiverine) and pharmaceutically acceptable salts thereof, 3-(2-hydroxy-2,2-diphenylacetoxy)-spiro[bicyclo[3.2.1]octane-8,1'-pyrrolidin]-1'-ium (trospium) pharmaceutically acceptable salts, and 3-(2-cyclopentyl-2-hydroxy-2-phenylacetoxy)-1,1-dimethylpyrrolidinium (glycopyrrolium) pharmaceutically acceptable salts, are particularly advantageous.

Solifenacin and pharmaceutically acceptable salts and compounds thereof, including the quaternary ammonium salts thereof, and their preparation are described in U.S. Pat. No. 6,017,927. Methods for the preparation and for the purification of solifenacin and its salts, in particular of solifenacin succinate, are described for example in WO 2007/076116, WO 2009/139002, WO 2011/003624 and WO 2012/001481.

Propiverine and pharmaceutically acceptable salts thereof, in particular its hydrochloride, are described in DD 106643, CN 1285348, CN 102218063(A), KR 2005-0011138, KR 2005-0011139, KR20110111782 (A) and in WO 2011/114195. The propiverine quaternary salts. i.e. the (C1-C4)alkyl propiverinium halides may be prepared by reacting 1-methyl-4-[(2,2-diphenyl-2-propoxy)acetoxy]piperidine (propiverine base) with a (C1-C4)alkyl halide (chloride, bromide or iodide), the propiverine base starting material being also obtained as crude product as described in WO 2011/114195 or by hydrolysis of propiverine hydrochloride, which is an easily available commercial product also obtainable for example as described in DD 106643, CN 1285348, CN 102218063(A) KR 2005-0011138, KR 2005-0011139, KR20110111782 (A) or in the aforesaid WO 2011/114195. In practice, an aqueous suspension of propiverine hydrochloride is treated with an inorganic base and crude propiverine base is recovered by extraction from an organic solvent and evaporation of the solvent; and the residue is treated with a (C1-C4)alkyl (preferably methyl) halide (chloride, bromide or iodide) in an alcoholic solution and the 1-alkyl-1-methyl-4-[(2,2-diphenyl-2-propoxy)acetoxy]piperidinium halide which precipitates is isolated.

Trospium pharmaceutically acceptable salts, in particular its chloride, may be prepared as described in U.S. Pat. No. 3,480,626 and other trospium pharmaceutically acceptable salts, in particular the tartrate, maleate, fumarate and succinate salts thereof, are cited in US 2006/0293356.

Glycopyrronium pharmaceutical acceptable salts, in particular the bromide, are obtainable according to U.S. Pat. No. 2,956,062.

Trospium is a long-acting nsPAChA whose absorbed amount has an average plasma half-life of about 18 hours. Solifenacin succinate is another nsPAChA having long-acting characteristics; the elimination half-life of solifenacin after chronic dosing is approximately 45 to 68 hours (VESIcare® Tablets label).

Also other quaternary ammonium salts or sulfonium salts of formula II above, such as homatropine quaternary salts, anisotropine quaternary salts, clidinium quaternary salts, benzilonium quaternary salts are suitable nsPAChAs, but their half-life is short.

According to the present invention, in order to assure neuroprotection the nsPAChAs are concurrently or sequentially administered with the above AChEIs, at a daily dose which is from more than 200% to 800% the recommended dose of said nsPAChA used in the anticholinergic therapy.

According to a preferred embodiment, trospium chloride, at daily doses of from more than 80 mg to 320 mg in an IR formulation or from more than 120 mg to 480 mg in an ER formulation; solifenacin succinate, at daily doses of from more than 20 mg to 80 mg in an IR formulation; propiverine hydrochloride, at daily doses of from more than 60 mg to 120 mg in an IR or ER formulation; and glycopyrrolium, at daily doses of from 8.2 mg to 64 mg, in IR or ER formulation, allow the administration of AChEI doses that are from 2.5 to 7 times higher than their maximum recommended daily doses, in order to induce AChEI blood levels, not attainable with hypothetical identical doses of AChEI, administered alone or in combination with lower doses of nsPAChA.

In particular, the aforementioned daily doses of trospium chloride, solifenacin succinate, propiverine hydrochloride or glycopyrrolium bromide allow the safe administration of donepezil hydrochloride at a daily dose of from 25 mg to 151 mg; of rivastigmine hydrogen tartrate, at a daily dose of from 30 mg to 93 mg; galantamine hydrobromide, at a daily dose of from 60 mg to 224 mg; and huperzine A, at a dose up to 4.8 mg, without inducing the most dangerous adverse effects of said AChEI.

For the intended use, the nsPAChA is formulated in pharmaceutical compositions comprising, as an active ingredient thereof, said nsPAChA in admixture with a pharmaceutical carrier.

In brand or generic nsPAChAs used in the anticholinergic therapy, for example, anisotropine hydrobromide is available in unit forms at the maximum dose of 50 mg; butylscopolamine bromide is available in unit forms at the maximum dose of 20 mg; cimetropium bromide is available in unit forms at the maximum dose of 50 mg; clidinium bromide, is available in unit forms, also comprising 2.5 mg chlordiazepoxide, at the maximum dose of 5 mg; glycopyrrolium bromide is available in unit forms at the maximum dose of 2 mg; otilonium bromide is available in unit forms at the maximum dose of 40 mg; prifinium bromide is available in unit forms at the maximum dose of 60 mg; propiverine hydrochloride is available in IR unit forms at the maximum dose of 15 mg and in a ER unit form at the maximum dose of 30 mg; solifenacin succinate is available in unit forms at the maximum dose of 10 mg; timepidium bromide is available in unit forms at the maximum dose of 30 mg; trospium chloride is available in IR unit forms at the maximum dose of 20 mg and in ER unit form at the maximum dose of 60 mg; and valethamate bromide is available in unit forms, also comprising 325 mg paracetamol, at the maximum dose of 10 mg.

The pharmaceutical compositions of the present invention for use for inducing neuroprotection and combating neurodegeneration, as illustrated above, contain an nsPAChA, for example selected from the group consisting of those mentioned in the preceding paragraph, at a dose of from more than 200% to 800%, advantageously from 210% to 800%, preferably from 250% to 800%, the maximum dose defined in said paragraph, in admixture with a pharmaceutical carrier.

For example, said pharmaceutical compositions comprise an nsPAChA selected from the group consisting of anisotropine hydrobromide, in an amount of from more than 100 mg to 400 mg, preferably from 110 mg to 400 mg; butylscopolamine bromide, in an amount of from more than 40 mg to 160 mg, preferably from 44 mg to 160 mg; cimetropium bromide, in an amount of from more than 100 mg to 400 mg, preferably from 110 mg to 400 mg; clidinium bromide, in an amount of from more than 10 mg to 40 mg, preferably from 11 mg to 40 mg; glycopyrrolium bromide, in an amount of from more than 4 mg to 16 mg, preferably from 4.2 mg to 16 mg; otilonium bromide, in an amount of from more than 80 mg to 320 mg, preferably from 84 mg to 320 mg; prifinium bromide, in an amount of from more than 60 mg to 240 mg, preferably from 63 mg to 240 mg; propiverine hydrochloride, in an amount of from more than 30 mg to 240 mg, preferably from 31.5 mg to 240 mg; solifenacin succinate, in an amount of from more than 20 mg to 80 mg, preferably from 21 mg to 80 mg; timepidium bromide, in an amount of from more than 60 mg to 240 mg, preferably from 63 mg to 240 mg; trospium chloride, in an amount of from more than 40 mg to 480 mg, preferably from 42 mg to 480 mg; and valethamate bromide, in an amount of from more than 20 mg to 80 mg, preferably from 21 mg to 80 mg; in admixture with a pharmaceutical carrier.

According to a preferred embodiment, the present invention provides a pharmaceutical composition comprising, as an active ingredient, an nsPAChA selected from the group consisting of glycopyrrolium bromide, in an amount of from 4.1 mg to 16 mg, preferably from 4.1 mg to 12 mg, in an IR formulation; glycopyrrolium bromide, in an amount of from 8 to 64 mg, preferably from 16 mg to 64 mg, in an ER formulation trospium chloride in an amount of from 42 mg to 160 mg, preferably from 60 mg to 160 mg, in admixture with a pharmaceutical carrier in an IR formulation; trospium chloride in an amount of from 126 mg to 480 mg, preferably from 160 mg to 480 mg, in admixture with a pharmaceutical carrier in an ER formulation; solifenacin succinate in an amount of from 21 mg to 80 mg, preferably from 25 mg to 80 mg, in admixture with a pharmaceutical carrier in an IR formulation; propiverine hydrochloride in an amount of from 31.5 mg to 120 mg, preferably from 35 mg to 120 mg, in admixture with a pharmaceutical carrier in an IR formulation; and propiverine hydrochloride in an amount of from 61.5 mg to 240 mg, preferably from 65 mg to 240 mg, in admixture with a pharmaceutical carrier in an ER formulation.

The aforementioned combination of the synergistic action of the nsPAChAs (peripheral only) and of the AChEI (both central and peripheral), inducing a theoretically infinite increase of the nsPAChA/AChEI pair doses without untoward peripheral anticholinergic side effects, allows the treatment of patients suffering from dementia of Alzheimer type with overdoses of both nsPAChA and AChEI and combats neurodegeneration. Thus, these pharmaceutical compositions are useful for inducing neuroprotection and combating neurodegeneration in a patient, suffering from an Alzheimer type dementia, who is treated with a dose an AChEI which is from 2.5 to 7 times the maximum recommended dose of said AChEI.

Thus, for example, the above pharmaceutical compositions containing an nsPAChA, may be used in combination with donepezil or a pharmaceutically acceptable salt thereof, in particular donepezil hydrochloride at a dose of from 25 mg to 151 mg; rivastigmine or a pharmaceutically acceptable salt thereof, in particular rivastigmine hydrogen tartrate, at a dose in rivastigmine of from 30 mg to 93 mg; and galantamine or a pharmaceutically acceptable salt thereof, in particular galantamine hydrobromide, at a dose in galantamine of from 60 mg to 224 mg, for inducing neuroprotection and combating neurodegeneration.

According to an advantageous embodiment, the pharmaceutical compositions, prepared by using the nsPAChAs according to the present invention, are present in unit forms also containing other active ingredients, in particular an AChEI at the aforementioned overdoses, to assure neuroprotection and to combat neurodegeneration in a patient suffering from a dementia of Alzheimer type.

B. The AChEIs

Advantageous AChEIs are those currently used or tested for this indication, such as 1,2,3,4-tetrahydro-9-acridinamine (tacrine), 9-amino-2,3,5,6,7,8-hexahydro-1H-cyclopenta[b]quinoline (ipidacrine); (±)-2,3-dihydro-5,6-dimethoxy-2-[[1-(phenylmethyl)-4-piperidinyl]methyl]-1H-inden-1-one (donepezil) and its pharmaceutically acceptable salts, in particular the hydrochloride, 3-[2-(1-benzyl-4-piperidyl)ethyl]-5,7-dihydro-6H-pyrrolo[3,2-f]-1,2-benzisoxazol-6-one (icopezil) and its pharmaceutically acceptable salts, in particular the maleate, 3-[1-benzylpiperidin-4-yl]-1-(2,3,4,5-tetrahydro-1H-1-benzazepin-8-yl)propan-1-one (zanapezil) and its pharmaceutically acceptable salts, in particular the fumarate, (S)—N-Ethyl-N-methyl-3-[1-(dimethylamino)ethyl]-phenyl carbamate (rivastigmine) and its pharmaceutically acceptable salts, in particular the hydrogen (2R,3R)-tartrate, 4aS,6R,8aS-3-methoxy-11-methyl-4a,5,9,10,11,12-hexahydroxy-6H-benzofuro[3a,3,2-e,f]benzazepin-6-ol (galantamine) and its pharmaceutically acceptable salts, in particular the hydrobromide; (1R,9S,13E)-1-amino-13-ethylidene-11-methyl-6-azatricyclo[7.3.1.0$^{2,7}$]trideca-2

(7),3,10-trien-5-one (huperzine A) and phenserine and its analogs encompassed by the general formula I

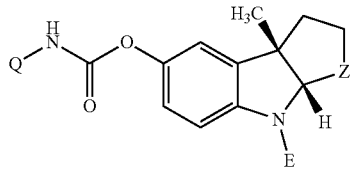

wherein Q is a phenyl group optionally substituted with a $(C_1-C_4)$alkyl or with a methoxy group, Z is an oxygen or sulfur atom or a N-E' radical, E and E', independently, are hydrogen or a methyl group optionally substituted with a phenyl or benzyl group; and pharmaceutically acceptable salts thereof.

Exemplary AChEIs of formula (I), described in U.S. Pat. No. 6,683,105, are phenserine (Q=phenyl; E=CH$_3$; Z=N—CH$_3$); (−)-N$^1$,N$^8$-bisnorphenserine (Q=phenyl; E=H; Z=N—H); 4'-methoxyphenserine (Q=4'-methoxyphenyl; E=CH$_3$; Z=N—CH$_3$); (−)-N$^1$,N$^8$-bisbenzylnorphenserine (Q=phenyl; E=CH$_2$C$_6$H$_5$; Z=N—CH$_2$C$_6$H$_5$); tolserine (Q=o-tolyl; E=CH$_3$; Z=N—CH$_3$); N$^1$-benzylnortolserine (Q=o-tolyl; E=CH$_3$; Z=N—CH$_2$—C$_6$H$_5$); N$^1$-phenethylnortolserine (Q=o-tolyl; E=CH$_3$; Z=N—CH$_2$—CH$_2$—C$_6$H$_5$); N$^1$-nortolserine (Q=o-tolyl; E=CH$_3$; Z=N—H); N$^8$-benzylnortolserine (Q=o-tolyl; E=N—CH$_2$—C$_6$H$_5$; Z=N—CH$_3$); N$^8$-phenethylnortolserine (Q=o-tolyl; E=N—CH$_2$—CH$_2$—C$_6$H$_5$; Z=N—CH$_3$); N$^8$-nortolserine (Q=o-tolyl; E=H; Z=N—CH$_3$); N$^1$,N$^8$-bisnortolserine (Q=o-tolyl; E=H; Z=N—H); (−)-N$^1$,N$^8$-bisbenzylnortolserine (Q=o-tolyl; E=CH$_2$C$_6$H$_5$; Z=N—CH$_2$C$_6$H$_5$); cymserine (Q=p-isopropylphenyl; E=CH$_3$; Z=N—CH$_3$); N$^1$-benzylnorcymserine (Q=p-isopropylphenyl; E=CH$_3$; Z=N—CH$_2$—C$_6$H$_5$); N$^1$-phenethylnorcymserine (Q=p-isopropylphenyl; E=CH$_3$; Z=N—CH$_2$—CH$_2$—C$_6$H$_5$); N$^1$-norcymserine (Q=p-isopropylphenyl; E=CH$_3$; Z=N—H); N$^8$-benzylnorcymserine (Q=p-isopropylphenyl; E=N—CH$_2$—C$_6$H$_5$; Z=N—CH$_3$); N$^8$-phenethylnorcymserine (Q=p-isopropylphenyl; E=N—CH$_2$CH$_2$C$_6$H$_5$; Z=NCH$_3$); N$^8$-norcymserine (Q=p-isopropylphenyl; E=H; Z=N—CH$_3$); N$^1$,N$^8$-bisnorcymserine (Q=p-isopropylphenyl; E=H; Z=N—H); (−)-N$^1$,N$^8$-bisbenzylnorcymserine (Q=p-isopropylphenyl; E=CH$_2$C$_6$H$_5$; Z=N—CH$_2$C$_6$H$_5$); thiacymserine (Q=p-isopropylphenyl; E=CH$_3$; Z=S); thiatolserine (Q=o-tolyl; E=CH$_3$; Z=S).

Donepezil hydrochloride, rivastigmine hydrogen (2R, 3R)-tartrate and galantamine hydrobromide are the preferred AChEIs, phenserine tartrate and huperzine A also being advantageous AChEIs, for improving dementias of Alzheimer's type according to the present invention. Specifically, all the donepezil, rivastigmine, galantamine phenserine and huperzine A salts solvates, analogs, derivatives and prodrugs are AChEIs useful for the method of the present invention.

According to the present invention, an AChEI, when used at a dose which is from 2.5 to 7 times the maximum recommended dose in a patient suffering from Alzheimer type dementia, in combination with a nsPAChA at the aforementioned doses, is well tolerated and is found in the blood of said patients at levels that are much higher than those expected for the administered doses, such that 2.5 times the maximum recommended dose of an AChEI is sufficient to induce neuroprotection. However, the present invention contemplates the safe administration of even higher doses of said AChEI assuring a substantially increased supply of acetylcholine in the CNS with consequent ability to combat neurodegeneration in said patient.

Among the preferred AChEIs, donepezil or a pharmaceutically acceptable salt thereof, in particular donepezil hydrochloride at a dose of from 25 mg to 151 mg rivastigmine or a pharmaceutically acceptable salt thereof, in particular rivastigmine hydrogen tartrate at a daily oral dose, in rivastigmine, of from 30 mg to 84 mg or at a daily transdermal dose, in rivastigmine, of from 30 mg/24 hours to 93 mg/24 hours; and galantamine or a pharmaceutically acceptable salt thereof, in particular galantamine hydrobromide at a dose, in galantamine, of from 60 mg to 224 mg, and huperzine A at a dose of from 0.45 mg to 4.8 mg; give very high blood levels assuring neuroprotection, when a nsPAChA is concurrently or sequentially administered therewith at a daily dose which is from more than 200% to 800% the dose of said nsPAChA used in the anticholinergic therapy. In particular, said nsPAChA is selected from the group consisting of pharmaceutically acceptable salts of trospium, pharmaceutically acceptable salts of glycopyrrolium, solifenacin and pharmaceutically acceptable salt thereof and propiverine and pharmaceutically acceptable salt thereof.

According to an advantageous embodiment, said AChEI is donepezil hydrochloride, administered at a daily dose of from 25 mg to 151 mg and said nsPAChA is solifenacin succinate, administered at a daily dose of from 21 mg to 80 mg.

According to another advantageous embodiment, said AChEI is galantamine, as hydrobromide, administered at a daily dose of from 60 mg to 224 mg, and said nsPAChA is propiverine, as hydrochloride, administered at a daily dose of from 61 mg to 240 mg.

According to a further advantageous embodiment, said AChEI is rivastigmine, as hydrogen tartrate, administered at a daily dose of from 30 mg to 93 mg, and said nsPAChA is selected from the group consisting of trospium chloride, administered at a daily dose of from 80 mg to 480 mg; propiverine hydrochloride, administered at a daily dose of from 61 mg to 240 mg; and solifenacin succinate, administered at a daily dose of from 21 mg to 80 mg.

The AChEIs are administered in pharmaceutical compositions wherein the active ingredient is in admixture with a pharmaceutical carrier. Said compositions may be those which are found in the commercial, brand or generic products.

In view of the high doses which can be administered according to the present invention, the AChEI may be formulated in new compositions. For example, donepezil hydrochloride may be orally administered once a day in a composition, comprising said donepezil hydrochloride in an amount of from 25 mg to 151 mg, in admixture with a pharmaceutical carrier; rivastigmine may be orally administered twice per day in a composition comprising rivastigmine hydrogen tartrate, in an amount in rivastigmine of from 15 mg to 42 mg, in admixture with a pharmaceutical carrier in an IR formulation; and galantamine may be orally administered twice per day in a composition comprising galantamine hydrobromide, in an amount in galantamine of from 40 mg to 112 mg in admixture with a pharmaceutical carrier in an IR formulation, or once a day in a pharmaceutical composition comprising galantamine hydrobromide in an amount in galantamine of from 60 mg to 224 mg in admixture with a pharmaceutical carrier in an ER formulation.

As set forth above, an overdose of an AChEI may be administered to a patient suffering from Alzheimer type dementia without concurrent cholinergic adverse effects by concomitantly administering an nsPAChA, at the aforementioned dose, to said patient, the sole remaining adverse effect being nausea/vomiting. This adverse effect may be alleviated by administration of a non-anticholinergic antiemetic agent (naAEA).

Any antiemetic agent substantially devoid of central anticholinergic effects may be used in order to block emesis due to the overdoses of AChEIs which are administered according to the present invention. A list of typical naAEAs adapted to this use is reported in WO 2011/034568. Advantageous naAEAs are domperidone, at a daily dose of from 10 mg to 80 mg, metoclopramide, at a daily dose of from 10 mg to 60 mg, aprepitant, at a dose of from 40 mg to 125 mg; alosetron, orally administered in 0.5-mg or in 1-mg tablets at a dose of 0.5-1 mg, once or twice a day; dolasetron mesylate, orally administered in 50-mg or in 100-mg tablets, at a daily dose of 100 mg; granisetron, orally administered orally in 1-mg or in 2-mg tablets, at a dose of 1 mg twice a day or 2 mg once a day, or parenterally administered in a 3-mg/1-ml solution for i.m. injection or in a 3 mg/3-ml solution for i.v. injection; ondansetron, orally administered in 4-mg or in 8-mg tablets at a dose of from 4 mg to 24 mg; palonosetron, administered in a 0.25-mg/5-ml solution by intravenous injection at a dose of 0.25 mg; ramosetron, orally or intravenously administered at a dose of 5 mg; and tropisetron, administered either intravenously in a 2-mg/2-ml or 5-mg/5-ml solution at a dose of 2 mg or 5 mg, or orally administered in a 5-mg capsule at a dose of 5 mg; the above doses being referred to their contents in 5-HT3-antagonist's base, unless otherwise specified.

C. The Fixed-Dose Combinations

As mentioned above, the nsPAChA may be formulated in a pharmaceutical composition also containing an AChEI.

Thus, the present invention also provides a pharmaceutical unit form particularly useful for inducing high and even very high blood concentrations of the AChEI in a human being, which comprises (a) a nsPAChA selected from the group consisting of solifenacin, pharmaceutically acceptable salts of solifenacin, propiverine, pharmaceutically acceptable salts of propiverine, trospium quaternary salts, clidinium quaternary salts, benzilonium quaternary salts and glycopyrronium quaternary salts, in an amount of from more than 200% to 800% the maximum amount contained in the commercial products for the anticholinergic therapy; and (b) an AChEI selected from the group consisting of (±)-2,3-dihydro-5,6-dimethoxy-2-[[1-(phenylmethyl)-4-piperidinyl]methyl]-1H-inden-1-one (donepezil) and pharmaceutically acceptable salts thereof, (S)—N-Ethyl-N-methyl-3-[1-(dimethylamino)ethyl]-phenyl carbamate (rivastigmine) and pharmaceutically acceptable salts thereof, 4aS,6R,8aS-3-methoxy-11-methyl-4a,5,9,10,11,12-hexahydroxy-6H-benzofuro[3a,3,2-e,f]benzazepin-6-ol (galantamine) and pharmaceutically acceptable salts thereof, and (1R,9S,13E)-1-amino-13-ethylidene-11-methyl-6-azatricyclo[7.3.1.0$^{2,7}$]trideca-2(7),3,10-trien-5-one (huperzine A), in an amount of from 2.5 to 7 times the maximum amount contained in the commercial products for the treatment of Alzheimer type dementia.

Preferred Component (a) is a pharmaceutically acceptable salt of trospium, especially trospium chloride, succinate, maleate, fumarate or tartrate, a pharmaceutically acceptable salt of solifenacin, especially its compound with succinic acid 1:1 (solifenacin succinate), a pharmaceutically acceptable salt of propiverine, especially its hydrochloride, a pharmaceutical acceptable salt of glycopyrronium, especially glycopyrronium bromide; a pharmaceutically acceptable salt of oxyphencyclimine, especially its hydrochloride or a pharmaceutically acceptable salt of tolterodine, especially its L-hydrogen tartrate.

Preferred Components (b) are donepezil hydrochloride, rivastigmine hydrogen tartrate, galantamine hydrobromide; and huperzine A.

More particularly, the nsPAChA Component (a) is selected from the group consisting of trospium chloride, in an amount of from 42 mg to 480 mg, advantageously from 50 mg to 480 mg, preferably from 60 mg to 480 mg per dosage unit, solifenacin succinate, in an amount of from 21 mg to 80 mg, advantageously from 22.5 mg to 80 mg, preferably from 25 mg to 80 mg per dosage unit; and propiverine hydrochloride in an amount of from 31.5 mg to 240 mg, advantageously from 32.25 mg to 240 mg, preferably from 35 mg to 240 mg per dosage unit. A Component (a) selected from the group consisting trospium chloride, in an amount of from 42 to 160 mg, preferably from 60 mg to 160 mg, in an IR formulation; glycopyrronium bromide, in an amount of from 4.1 to 16 mg, preferably from 4.5 to 12 mg in an IR formulation; propiverine hydrochloride, in an amount of from 31.5 mg to 120 mg, preferably from 35 mg to 120 mg, in an IR formulation, trospium chloride, in an amount of from 126 mg to 480 mg, preferably from 160 mg to 480 mg, in an ER formulation; and propiverine hydrochloride, in an amount of from 61.5 mg to 240 mg, preferably from 65 mg to 240 mg, in an ER formulation; is particularly advantageous.

The AChEI Component (b) is selected from the group consisting of donepezil hydrochloride, in an amount of from 25 mg to 151 mg, preferably from 57.5 to 151 mg, per dosage unit; rivastigmine, as the hydrogen tartrate thereof, in an amount of from 15 mg to 93 mg, preferably from 24 mg to 93 mg per dose unit; galantamine, as the hydrobromide thereof, in an amount of from 40 to 224 mg per dose unit; and huperzine A, in an amount of from 150 µg to 1.2 mg, preferably from 200 µg to 1.2 mg per dose unit. A Component (b) selected from the group consisting of rivastigmine (as hydrogen tartrate) in an IR oral formulation comprising from 15 mg to 42 mg of active ingredient; galantamine (as hydrobromide), in an IR formulation comprising from 40 mg to 112 mg of active ingredient; rivastigmine (as hydrogen tartrate), in an ER patch formulation releasing from 30 mg/24 hours to 93 mg/24 hours of active ingredient; and galantamine (as hydrobromide) in an ER formulation comprising from 60 mg to 168 mg of active ingredient; is particularly advantageous.

The unit form of the present invention may be a tablet, a capsule, a pre-measured volume of a liquid solution or suspension for oral administration or a patch for transdermal application. In said unit form the nsPAChA and the AChEI may be mixed together or separated according to known technologies in admixture with a pharmaceutical carrier in a pharmaceutical composition.

Component (a) and Component (b) are formulated with conventional pharmaceutical carriers in known formulations for oral use wherein said components are mixed together or separated, for example in two tablets introduced in a capsule or in a two-compartment capsule or in a multilayer (di-layer) tablet wherein the two components are both in IR or in ER form or one of the two components is in IR form and the other is in ER form, according to known technologies.

The pharmaceutical carriers and vehicles are those commonly used for the preparation of compositions for oral, buccal and parenteral, in particular transdermal, administration. Appropriate unit forms comprise the oral forms such as tablets, soft or hard gelatin capsules, powders or granulates in sachets and suitably measured oral solutions or suspensions as well as patches for transdermal administration.

Component (a) and component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and component (b) may also be formulated in the form of microcapsules, optionally with one or more carriers or additives.

For oral administration, Component (a) and Component (b), together or separately, are formulated by mixing the active ingredient with conventional pharmaceutical acceptable carriers enabling said active ingredients to be formulated in tablets, dragees, orally disintegrating tablets, capsules, liquid solutions or suspensions, syrups and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricants such as polyethylenglycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

Carriers for liquid, normally aqueous, suspensions or solutions include for example antioxidants, such as sodium metabisulfite or sodium sulfite, thickening agents, such as micnrocrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The composition according to the present invention may be in form of a capsule containing two tablets as described herein above, one of them comprising Component (a) and the other comprising Component (b).

The association nsPAChA/AChEI may be formulated in tablets in which one or both of the two components is in controlled-release formulation, for example as a dispersion of said component in hydroxypropyl methyl cellulose or in a film-coated microgranule. Advantageously, the AChEI, in a ER-formulation is in the core and the nsPAChA, in IR-formulation, is in the outer layer in multi-layer tablets in which, for example, both the core and the outer layer are coated with a film. Analogously, capsules made of two separated parts, one containing Component (a), in IR- or ER-formulation and the other containing Component (b), in IR- or ER-formulation, may be used Carriers and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

In particular, the unit forms of the present invention comprise a member selected from the group consisting of trospium chloride, solifenacin succinate and propiverine hydrochloride, as an nsPAChA and a member selected from the group consisting of donepezil hydrochloride, in an amount of from 25 mg to 151 mg; rivastigmine hydrogen tartrate; in an amount in rivastigmine of from 15 mg to 42 mg; galantamine hydrobromide, in an amount in galantamine of from 40 to 112 mg; and huperzine A, in an amount of from 150 µg to 1.2 mg as an AChEI.

According to an embodiment, the compositions of the present invention are formulated by mixing the Component (a) and the Component (b) together, in admixture with a pharmaceutical carrier for an immediate or extended release and are useful for inducing neuroprotection in a patient suffering from a dementia of Alzheimer type treated with said AChEI.

An advantageous composition according to this embodiment comprises from 42 mg to 160 mg preferably from 80 mg to 160 mg; of trospium chloride, as Component (a); and
    from 15 mg to 42 mg, preferably form 18 mg to 42 mg, of rivastigmine (as hydrogen tartrate); or
    from 40 mg to 84 mg preferably from 42 mg to 84 mg, of galantamine (as hydrobromide), as Component (b),
as mixed together and with a pharmaceutical carrier in an IR formulation.

Another advantageous composition according to this embodiment comprises
    from 21 mg to 80 mg, preferably from 25 mg to 80 mg, of solifenacin succinate, as Component (a); and
    from 25 mg to 70 mg, preferably from 40 mg to 70 mg, of donepezil hydrochloride, as Component (b),
as mixed together and with a pharmaceutical carrier in an IR formulation.

A particular composition according to this embodiment comprises
    25 mg of solifenacin succinate, as Component (a); and
    from 40 mg to 60 mg of donepezil hydrochloride, as Component (b), as mixed together and with a pharmaceutical carrier in an IR formulation.

A further advantageous composition according to this embodiment comprises
    from 31.5 mg to 120 mg, preferably from 35 mg to 120 mg of propiverine hydrochloride, as Component (a); and
    from 15 mg to 42 mg, preferably form 18 mg to 42 mg, of rivastigmine (as hydrogen tartrate); or
    from 40 mg to 112 mg preferably from 42 mg to 112 mg, of galantamine (as hydrobromide), as Component (b),
as mixed together and with a pharmaceutical carrier in an IR formulation.

A particular composition according to this embodiment comprises
    35 mg of propiverine hydrochloride, as Component (a); and
    25 mg of rivastigmine (as hydrogen tartrate), as Component (b), as mixed together and with a pharmaceutical carrier in an IR formulation.

Another particular composition according to this embodiment comprises 75 mg of propiverine hydrochloride, as Component (a); and
60 mg of galantamine (as hydrobromide), as Component (b), as mixed together and with a pharmaceutical carrier in an IR formulation.

According to another embodiment, the compositions of the present invention are formulated by mixing the Component (a) with a pharmaceutical carrier for an immediate or extended release in tablets (Tablet A) and the Component (b), separately, with a pharmaceutical carrier for an immediate or extended release in tablets (Tablet B) and introducing Tablet A and Tablet B in a capsule for oral administration as described for example in GB 1204580 or in US 2007/0224259.

An advantageous composition according to this embodiment consists of soft or hard gelatin capsules each containing Tablet A comprising from 31.5 mg to 40 mg of propiverine hydrochloride, as Component (a), in admixture with a pharmaceutical carrier in a IR formulation; and
Tablet B, comprising from 25 mg to 35 mg of rivastigmine (as hydrogen tartrate); as Component (b), in admixture with a pharmaceutical carrier in an IR-formulation.

Another advantageous composition according to this embodiment consists of soft or hard gelatin capsules each containing Tablet A comprising from 4.1 mg to 16 mg of glycopyrrolium bromide, as Component (a), in admixture with a pharmaceutical carrier in a IR formulation; and
Tablet B, comprising from 25 mg to 42 mg of rivastigmine (as hydrogen tartrate); as Component (b), in admixture with a pharmaceutical carrier in an IR-formulation.

A further advantageous composition according to this embodiment consists of soft or hard gelatin capsules each containing Tablet A comprising from 6 mg of glycopyrrolium bromide, as Component (a), in admixture with a pharmaceutical carrier in a IR formulation; and
Tablet B, 30 mg of rivastigmine (as hydrogen tartrate); as Component (b), in admixture with a pharmaceutical carrier in an IR-formulation.

According to a further embodiment, the compositions according to the present invention are formulated in a di-layer tablet which releases two drug doses, in which the release of a drug from one drug-containing layer does not interfere with the release of a drug from the other drug-containing layer as described for example in WO 2006/089493. An advantageous composition according to this embodiment consists of Layer A, comprising from 21 mg to 40 mg of solifenacin succinate, as Component (a), in admixture with a pharmaceutical carrier in a IR formulation and
Layer B, comprising from 25 mg to 50 mg of donepezil hydrochloride, as Component (b), in admixture with a pharmaceutical carrier in an IR-formulation.

Another embodiment of the present invention provides unit forms consisting of tablets comprising from 21 mg to 40 mg, of solifenacin succinate, as Component (a); and
from 25 mg to 50 mg preferably from 37.5 mg to 50 mg, of donepezil hydrochloride;

as Component (b),
in admixture with a pharmaceutical carrier in a IR-formulation for oral administration.

According to a preferred embodiment, the invention provides unit forms consisting of tablets comprising 25 mg of solifenacin succinate, as Component (a) and
from 25 mg to 50 mg preferably from 37.5 mg to 50 mg, of donepezil hydrochloride, as Component (b), in admixture with a pharmaceutical carrier, in a formulation for oral administration to be administered once a day.

Another preferred embodiment of the invention provides unit forms for oral administration consisting of tablets comprising from 21 mg to 80 mg of solifenacin succinate, as Component (a) and
from 25 mg to 151 mg preferably from 57.5 mg to 151 mg, of donepezil hydrochloride, as Component (b), in admixture with a pharmaceutical carrier, in a formulation for oral administration to be administered once a day.

III. A Third Aspect of the Present Invention

In a third aspect, the present invention provides an improved method to augment and extend the efficacy of conventional cholinergic therapies for Alzheimer type dementias by mitigating the common dose-limiting adverse events of cholinomimetic treatments of said Alzheimer type dementias that arise as a result of the concomitant excessive stimulation of cholinergic receptors in the PNS. Drugs that act to selectively inhibit the activation of all or nearly all the muscarinic receptors in the PNS, but not in the CNS, resulting from cholinomimetic therapy have the potential to reduce the adverse effects, such that higher cholinomimetic doses can be administered leading to greater and more prolonged antidementia efficacy with fewer peripherally mediated side effects. By combining an extended release cholinomimetic with a peripheral anticholinergic having an advantageous duration of pharmacologic action, in a single dosage form, the benefits to patients of an even longer duration of action is also achieved.

In particular, the invention provides a method for increasing AChEI blood levels in a human being, which comprises administering said human being an AChEI dose which is at least 2.5, up to 7 times higher than the dose used in the treatment of Alzheimer type dementias, in combination with a nsPAChA dose which is at least as high as, advantageously at least twice, preferably more than twice up to 8 times higher than the dose used in the anticholinergic therapy.

More particularly, the invention provides a method for increasing the blood levels of an AChEI in a human subject which comprises administering to said subject a nsPAChA selected from the group consisting of solifenacin, pharmaceutically acceptable salts and compounds of solifenacin, pharmaceutically acceptable salts of trospium, pharmaceutically acceptable salts of glycopyrrolium, propiverine and pharmaceutically acceptable salts of propiverine, said nsPAChA being administered at a dose which is at least as high as, up to eight times the dose used for the anticholinergic therapy, advantageously at a dose of from more than twice to eight times, preferably from 2.5 to 8 times the dose used for the anticholinergic therapy, in combination with a dose of said AChEI which is from 2.5 to 7 times the dose used for the treatment of Alzheimer type dementia. Said human subject may be a patient suffering from dementia of Alzheimer type. The pharmaceutically acceptable salts of propiverine and solifenacin include the propiverine and solifenacin quaternary salts, in particular the methyl chloride, the methyl iodide and the methyl bromide thereof.

This finding is surprising because an increase in blood levels of a drug normally also increases the risk of side effects while, in the case of the combined nsPAChA/AChEI treatment according to the present invention, the most common and dangerous adverse effects are in fact suppressed.

The present invention also provides a pharmaceutical composition comprising, as an active ingredient, an nsPAChA selected from the group consisting of solifenacin and pharmaceutically acceptable salts thereof, propiverine and pharmaceutically acceptable salts thereof, and trospium pharmaceutically acceptable salts, in an amount which is from 100% to 800% the maximum amount of said nsPAChA contained in compositions indicated for the anticholinergic therapy, for use for increasing the AChEI blood levels in a human treated with an AChEI dose which is from 250% to 700% the maximum recommended dose of said AChEI.

A. The nsPAChAs

Advantageously, the used nsPAChAs are quaternary ammonium nsPAChAs, sulfonium nsPAChAs, (1S)-(3R)-1-azabicyclo[2.2.2]oct-3-yl 3,4-dihydro-1-phenyl-2(1H)-isoquinolinecarboxylate (solifenacin) and its pharmaceutically acceptable salts, (1-methylpiperidin-4-yl) 2,2-di(phenyl)-2-propoxyacetate (propiverine) and its pharmaceutically acceptable salts, 1,4,5,6-tetrahydro-1-methylpyrimidin-2-yl-methyl α-cyclohexyl-α-hydroxy-α-phenylacetate (oxyphencyclimine) and its pharmaceutically acceptable salts, (R)—N,N-diisopropyl-3-(2-hydroxy-5-methylphenyl)-3-phenylpropanamine (tolterodine) and its pharmaceutically acceptable salts. Said nsPAChAs, preferably, are compounds with duration of action of at least 6 hours, advantageously from 8 to 24 hours, more advantageously from 10 to 24 hours, preferably from 12 to 24 hours, even though nsPAChAs having an appropriate duration of action corresponding to the duration of action of the concomitantly administered AChEI may be successfully used.

Particularly advantageous quaternary ammonium nsPAChAs or sulfonium nsPAChAs are compounds of formula II

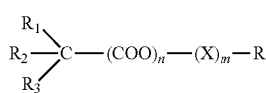

(II)

wherein
R is a radical selected from the group consisting of those of formulas (a)-(e)

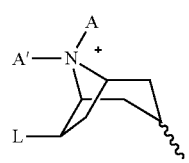

(a)

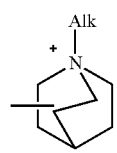

(b)

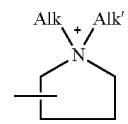

(c)

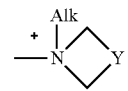

(d)

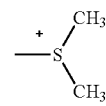

(e)

A being methyl and A' being $(C_1-C_4)$alkyl or 2-fluoroethyl group or A and A' forming a 1,4-butylene or 1,5-pentylene chain, L being hydrogen or methoxy, Alk and Alk' each being $(C_1-C_4)$alkyl and Y being a bivalent radical selected from the group consisting of 1,2-ethylene, 1,3-propylene, 1,4-butylene and 2-oxa-1,3-propylene; the corresponding counter ion being a pharmaceutically acceptable anion, such as a chloro, bromo, iodo, tartrate, hydrogen tartrate, succinate, maleate, fumarate, sulfate, hydrogen sulfate or methylsulfate anion;

n and m, independently, are zero or 1;

X is a $(C_2-C_3)$alkylene group;

$R_1$ and $R_2$ are each phenyl, cyclopentyl, cyclohexyl, 1-cyclohexenyl, 2-thienyl and, when R is a radical (a), also each represents $(C_1-C_4)$alkyl;

$R_3$ is H or OH or, only when R is a radical (a), also a COOAlk group, Alk being a $(C_1-C_4)$alkyl group.

Exemplary nsPAChAs of formula II above used for preparing medicaments for the treatment of Alzheimer type dementia in combination with AChEIs are anisotropine methylbromide [R=(a), A=A'=CH$_3$, L=H; n=1; m=0; R$_1$=R$_2$=n-C$_3$H$_7$; R$_3$=H;];

ciclotropium bromide [R=(a), A=CH$_3$, A'=isopropyl, L=H; n=1; m=0; R$_1$=phenyl; R$_2$=cyclopentyl; R$_3$=H];

flutropium bromide [R=(a), A=CH$_3$, A'=2-fluoroethyl, L=H; n=1; m=0; R$_1$=R$_2$=phenyl; R$_3$=OH];

homatropine methylbromide [R=(a), A=A'=CH$_3$, L=H; n=1; m=0; R$_1$=phenyl; R$_2$=R$_3$=H];

sintropium bromide; [R=(a), A=CH$_3$, A'=isopropyl, L=H; n=1; m=0; R$_1$=R$_2$=n-C$_3$H$_7$; R$_3$=H];

tematropium metilsulfate [R=(a), A=A'=CH$_3$, L=H; n=1; m=0; R$_1$=phenyl; R$_2$=COOC$_2$H$_5$; R$_3$=H];

tropenziline bromide [R=(a), A=A'=CH$_3$, L=methoxy; n=1; m=0; R$_1$=R$_2$=phenyl, R$_3$=OH];

trospium chloride [R=(a), A+A'=1,4-butylene, L=H; n=1; m=0; R$_1$=R$_2$=phenyl; R$_3$=OH];

clidinium bromide [R=(b)-3-, Alk=methyl; n=1; m=0; R$_1$=R$_2$=phenyl; R$_3$=OH];

droclidinium bromide [R=(b)-3-, Alk=methyl; n=1; m=0; R$_1$=phenyl; R$_2$=cyclopentyl; R$_3$=OH];

benzilonium bromide [R=(c)-3-, both Alk and Alk'=ethyl; n=1; m=0; R$_1$=R$_2$=phenyl; R$_3$—OH];

benzopyrronium bromide [R=(c)-3-, both Alk and Alk'=methyl; n=1; m=0; R$_1$=R$_2$=phenyl; R$_3$=OH];

cyclopyrronium bromide [R=(c)-3-, Alk=methyl and Alk'=ethyl; n=1; m=0; R$_1$=phenyl; R$_2$=cyclopentyl; R$_3$=H];

glycopyrronium bromide (glycopyrrolate) [R=(c)-3-, both Alk and Alk'=methyl; n=1; m=0; R$_1$=phenyl; R$_2$=cyclopentyl; R$_3$=H];

heteronium bromide [R=(c)-3-, both Alk and Alk'=methyl n=1; m=0; $R_1$=phenyl; $R_2$=2-thienyl; $R_3$=OH];

hexopyrronium bromide [R=(c)-3-, both Alk and Alk'=methyl; n=1; m=0; $R_1$=phenyl; $R_2$=cyclohexyl; $R_3$=H];

oxypyrronium bromide [R=(c)-2-, both Alk and Alk'=methyl; n=1; m=1; X=1,2-ethylene; $R_1$=phenyl; $R_2$=cyclohexyl; $R_3$=OH];

ritropirronium bromide [R=(c)-3-, both Alk and Alk'=methyl; n=1; m=0; $R_1$=phenyl; $R_2$=cyclopentyl; $R_3$=OH];

etipirium iodide [R=(d), Alk=methyl, Y=1,2-ethylene; n=1; m=1; X=1,2-ethylene; $R_1$=$R_2$=phenyl; $R_3$=OH];

fenclexonium methylsulfate [R=(d), Alk=$CH_3$, Y=1,3-propylene; n=0; m=1; X=1,2-ethylene; $R_1$=phenyl; $R_2$=1-cyclohexenyl; $R_3$=H];

tricyclamol chloride (procyclidine methochloride) [R=(d), Alk=methyl, Y=1,2-ethylene; n=0; m=1; X=1,2-ethylene; $R_1$=phenyl; $R_2$=cyclohexyl; $R_3$=OH];

tiemonium iodide [R=(d), Alk=methyl, Y=2-oxa-1,3-propylene; n=0; m=1; X=1,2-ethylene; $R_1$=phenyl; $R_2$=2-thienyl; $R_3$=OH];

hexasonium iodide [R=(e); n=1; m=1; X=1,2-ethylene; $R_1$=phenyl; $R_2$=cyclohexyl; $R_3$=H]; and oxysonium iodide [R=(e); n=1; m=1; X=1,2-ethylene; $R_1$=phenyl; $R_2$=cyclohexyl; $R_3$=OH.

A nsPAChA selected from the group consisting of (1S)-(3R)-1-azabicyclo[2.2.2]oct-3-yl 3,4-dihydro-1-phenyl-2(1H)-isoquinolinecarboxylate (solifenacin) or a pharmaceutically acceptable salt or compound thereof, 1-methyl-4-[(2,2-diphenyl-2-n-propoxy)acetoxy]piperidine (propiverine) and pharmaceutically acceptable salts thereof, 3-(2-hydroxy-2,2-diphenylacetoxy)-spiro[bicyclo[3.2.1]octane-8,1'-pyrrolidin]-1'-ium (trospium) pharmaceutically acceptable salts, and 3-(2-cyclopentyl-2-hydroxy-2-phenylacetoxy)-1,1-dimethylpyrrolidinium (glycopyrrolium) pharmaceutically acceptable salts, are particularly advantageous.

Solifenacin and pharmaceutically acceptable salts and compounds thereof, including the quaternary ammonium salts thereof, and their preparation are described in U.S. Pat. No. 6,017,927. Methods for the preparation and for the purification of solifenacin and its salts, in particular of solifenacin succinate, are described for example in WO 2007/076116, WO 2009/139002, WO 2011/003624 and WO 2012/001481.

Propiverine and pharmaceutically acceptable salts thereof, in particular its hydrochloride, are described in DD 106643, CN 1285348, CN 102218063(A), KR 2005-0011138, KR 2005-0011139, KR20110111782 (A) and in WO 2011/114195. The propiverine quaternary salts. i.e. the (C1-C4)alkyl propiverinium halides may be prepared by reacting 1-methyl-4-[(2,2-diphenyl-2-propoxy)acetoxy]piperidine (propiverine base) with a (C1-C4)alkyl halide (chloride, bromide or iodide), the propiverine base starting material being also obtained as crude product as described in WO 2011/114195 or by hydrolysis of propiverine hydrochloride, which is an easily available commercial product also obtainable for example as described in DD 106643, CN 1285348, CN 102218063(A) KR 2005-0011138, KR 2005-0011139, KR20110111782 (A) or in the aforesaid WO 2011/114195. In practice, an aqueous suspension of propiverine hydrochloride is treated with an inorganic base and crude propiverine base is recovered by extraction from an organic solvent and evaporation of the solvent; and the residue is treated with a (C1-C4)alkyl (preferably methyl) halide (chloride, bromide or iodide) in an alcoholic solution and the 1-alkyl-1-methyl-4-[(2,2-diphenyl-2-propoxy)acetoxy]piperidinium halide which precipitates is isolated.

Trospium pharmaceutically acceptable salts, in particular its chloride, may be prepared as described in U.S. Pat. No. 3,480,626 and other trospium pharmaceutically acceptable salts, in particular the tartrate, maleate, fumarate and succinate salts thereof, are cited in US 2006/0293356.

Glycopyrronium pharmaceutical acceptable salts, in particular the bromide, are obtainable according to U.S. Pat. No. 2,956,062.

Trospium is a long-acting nsPAChA whose absorbed amount has an average plasma half-life of about 18 hours. Also solifenacin succinate is an nsPAChA having long-acting characteristics, its half-life being very long, especially following long-term administration.

Also other quaternary ammonium salts or sulfonium salts of formula II above, such as homatropine quaternary salts, anisotropine quaternary salts, clidinium quaternary salts, benzilonium quaternary salts are suitable nsPAChAs, but their half-life is short.

According to the present invention, in order to increase AChEI blood levels, the nsPAChAs are concurrently or sequentially administered with the above AChEIs, at a daily dose which is from 100% to 800% the dose of said nsPAChA used in the anticholinergic therapy.

According to a preferred embodiment, trospium chloride, at daily doses of from 40 mg to 320 mg in an IR formulation or from 60 mg to 480 mg in an ER formulation; solifenacin succinate, at daily doses of from 10 mg to 80 mg in an IR formulation; propiverine hydrochloride, at daily doses of from 30 mg to 240 mg in an IR or ER formulation; and glycopyrrolium, at daily doses of from 8 mg to 64 mg, in IR or ER formulation, allow the administration of AChEI doses that are from 2.5 to 4, up to 7 times higher than their maximum recommended daily doses, in order to induce very high AChEI blood levels, not attainable with hypothetical identical doses of AChEI, administered alone or in combination with lower doses of nsPAChA.

In particular, the aforementioned daily doses of trospium chloride, solifenacin succinate, propiverine hydrochloride or glycopyrrolium bromide allow the safe administration of donepezil hydrochloride at a daily dose of from 25 mg to 151 mg; of rivastigmine hydrogen tartrate, at a daily dose of from 30 mg to 126 mg; and galantamine hydrobromide, at a daily dose of from 60 mg to 224 mg and huperzine A, at a dose up to 4.8 mg, without inducing the most dangerous adverse effects of said AChEI.

For the intended use, the nsPAChA is formulated in pharmaceutical compositions comprising, as an active ingredient thereof, said nsPAChA in admixture with a pharmaceutical carrier.

In brand or generic nsPAChAs used in the anticholinergic therapy, for example, anisotropine hydrobromide is available in unit forms at the maximum dose of 50 mg; butylscopolamine bromide is available in unit forms at the maximum dose of 20 mg; cimetropium bromide is available in unit forms at the maximum dose of 50 mg; clidinium bromide, is available in unit forms, also comprising 2.5 mg chlordiazepoxide, at the maximum dose of 5 mg, glycopyrrolium bromide is available in unit forms at the maximum dose of 2 mg; otilonium bromide is available in unit forms at the maximum dose of 40 mg; prifinium bromide is available in unit forms at the maximum dose of 60 mg; propiverine hydrochloride is available in IR unit forms at the maximum dose of 15 mg and in a ER unit form at the maximum dose of 30 mg; solifenacin succinate is available in unit forms at the maximum dose of 10 mg; timepidium bromide is available in unit forms at the maximum dose of 30 mg; trospium chloride is available in IR unit forms at the maximum dose of 20 mg and in ER unit form at the maximum dose of 60 mg; and valethamate bromide is available in unit forms, also comprising 325 mg paracetamol, at the maximum dose of 10 mg.

The pharmaceutical composition of the present invention, for use for inducing high and very high AChEI blood levels as illustrated above, contain an nsPAChA, for example selected from the group consisting of those mentioned in the preceding paragraph, at a dose of from 100% to 800%%, preferably from 200% to 800%, the maximum dose defined in said paragraph, in admixture with a pharmaceutical carrier.

For example, said pharmaceutical composition for inducing high an even very high AChEI levels, when administered to a human being treated with even a single AChEI dose, comprises an nsPAChA selected from the group consisting of anisotropine hydrobromide, in an amount of from 50 mg to 400 mg, preferably from 100 mg to 400 mg; butylscopolamine bromide, in an amount of from 20 mg to 160 mg, preferably from 40 mg to 160 mg; cimetropium bromide, in an amount of from 50 mg to 400 mg, preferably from 100 mg to 400 mg; clidinium bromide, in an amount of from 5 mg to 40 mg, preferably from 10 mg to 40 mg; glycopyrrolium bromide, in an amount of from 2 mg to 16 mg, preferably from 4 mg to 16 mg; otilonium bromide, in an amount of from 40 mg to 320 mg, preferably from 80 mg to 320 mg; prifinium bromide, in an amount of from 30 mg to 240 mg, preferably from 60 mg to 240 mg; propiverine hydrochloride, in an amount of from 15 mg to 240 mg, preferably from 30 mg to 240 mg; solifenacin succinate, in an amount of from 10 mg to 80 mg, preferably from 20 mg to 80 mg; timepidium bromide, in an amount of from 30 mg to 240 mg, preferably from 60 mg to 240 mg; trospium chloride, in an amount of from 20 mg to 480 mg, preferably from 40 mg to 480 mg; and valethamate bromide, in an amount of from 10 mg to 80 mg, preferably from 20 mg to 80 mg; in admixture with a pharmaceutical carrier.

According to a preferred embodiment, the present invention provides a pharmaceutical composition comprising, as an active ingredient, an nsPAChA selected from the group consisting of glycopyrrolium bromide, in an amount of from 2 mg to 16 mg, preferably from 4 mg to 12 mg, in an IR formulation; glycopyrrolium bromide, in an amount of from 4 mg to 64 mg, preferably from 8 mg to 64 mg, in an ER formulation; trospium chloride in an amount of from 20 mg to 160 mg, preferably from 40 mg to 160 mg, in admixture with a pharmaceutical carrier in an IR formulation; trospium chloride in an amount of from 60 mg to 480 mg, preferably from 120 mg to 480 mg, in admixture with a pharmaceutical carrier in an ER formulation; solifenacin succinate in an amount of from 10 mg to 80 mg, preferably from 20 mg to 80 mg, in admixture with a pharmaceutical carrier in an IR formulation; propiverine hydrochloride in an amount of from 15 mg to 120 mg, preferably from 30 mg to 120 mg, in admixture with a pharmaceutical carrier in an IR formulation; and propiverine hydrochloride in an amount of from 30 mg to 240 mg, preferably from 60 mg to 240 mg, in admixture with a pharmaceutical carrier in an ER formulation; for use for inducing high and even very high AChEI blood levels in a human subject treated with an overdose of said AChEI.

The aforementioned combination of the synergistic action of the nsPAChAs (peripheral only) and of the AChEI (both central and peripheral), inducing a theoretically infinite increase of the nsPAChA/AChEI pair doses without untoward peripheral anticholinergic side effects, allows the attainment of very high blood levels of said AChEI. Thus, these pharmaceutical compositions are useful for increasing AChEI blood levels in human subjects, including a patient, suffering from Alzheimer type dementia, who is treated with a dose of said AChEI which is from 2.7 to 7 times its maximal recommended dose, with a consequent better therapeutic response.

Thus, for example, the above pharmaceutical compositions containing an nsPAChA, may be used in combination with donepezil or a pharmaceutically acceptable salt thereof, in particular donepezil hydrochloride at a dose of from 25 mg to 151 mg; rivastigmine or a pharmaceutically acceptable salt thereof, in particular rivastigmine hydrogen tartrate, at a dose in rivastigmine of from 30 mg to 126 mg; and galantamine or a pharmaceutically acceptable salt thereof, in particular galantamine hydrobromide, at a dose in galantamine, of from 60 mg to 224 mg, for inducing very high AChEI blood levels.

According to an advantageous embodiment, the pharmaceutical compositions prepared by using the nsPAChAs according to the present invention are present in unit forms also containing other active ingredients, in particular an AChEI at the aforementioned overdoses, to increase the AChEI blood levels in human subjects, in particular in a patient suffering from a dementia Alzheimer type.

B. The AChEIs

Advantageous AChEIs are those currently used or tested for this indication, such as 1,2,3,4-tetrahydro-9-acridinamine (tacrine), 9-amino-2,3,5,6,7,8-hexahydro-1H-cyclopenta[b]quinoline (ipidacrine); (±)-2,3-dihydro-5,6-dimethoxy-2-[[1-(phenylmethyl)-4-piperidinyl]methyl]-1H-inden-1-one (donepezil) and its pharmaceutically acceptable salts, in particular the hydrochloride, 3-[2-(1-benzyl-4-piperidyl)ethyl]-5,7-dihydro-6H-pyrrolo[3,2-f]-1,2-benzisoxazol-6-one (icopezil) and its pharmaceutically acceptable salts, in particular the maleate, 3-[1-benzylpiperdin-4-yl]-1-(2,3,4,5-tetrahydro-1H-1-benzazepin-8-yl)propan-1-one (zanapezil) and its pharmaceutically acceptable salts, in particular the fumarate, (S)—N-Ethyl-N-methyl-3-[1-(dimethylamino)ethyl]-phenyl carbamate (rivastigmine) and its pharmaceutically acceptable salts, in particular the hydrogen (2R,3R)-tartrate, 4aS,6R,8aS-3-methoxy-11-methyl-4a,5,9,10,11,12-hexahydroxy-6H-benzofuro[3a,3,2-e,f]benzazepin-6-ol (galantamine) and its pharmaceutically acceptable salts, in particular the hydrobromide; (1R,9S,13E)-1-amino-13-ethylidene-11-methyl-6-azatricyclo[7.3.1.0$^{2,7}$]trideca-2(7),3,10-trien-5-one (huperzine A) and phenserine and its analogs encompassed by the general formula I

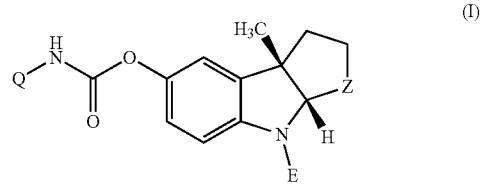

wherein Q is a phenyl group optionally substituted with a $(C_1-C_4)$alkyl or with a methoxy group, Z is an oxygen or sulfur atom or a N-E' radical, E and E', independently, are hydrogen or a methyl group optionally substituted with a phenyl or benzyl group, and pharmaceutically acceptable salts thereof.

Exemplary AChEIs of formula (I), described in U.S. Pat. No. 6,683,105, are phenserine (Q=phenyl; E=$CH_3$; Z=N—$CH_3$); (−)-$N^1$,$N^8$-bisnorphenserine (Q=phenyl; E=H; Z=N—H); 4'-methoxyphenserine (Q=4'-methoxyphenyl; E=$CH_3$; Z=N—$CH_3$); (−)-$N^1$,$N^8$-bisbenzylnorphenserine (Q=phenyl; E=$CH_2C_6H_5$; Z=N—$CH_2C_6H_5$); tolserine (Q=o-tolyl; E=$CH_3$; Z=N—$CH_3$); $N^1$-benzylnortolserine (Q=o-tolyl; E=$CH_3$; Z=N—$CH_2$—$C_6H_5$); $N^1$-phenethylnortolserine (Q=o-tolyl; E=$CH_3$; Z=N—$CH_2$—$CH_2$—$C_6H_5$); $N^1$-nortolserine (Q=o-tolyl; E=$CH_3$; Z=N—H); $N^8$-benzylnortolserine (Q=o-tolyl; E=N—$CH_2$—$C_6H_5$; Z=N—$CH_3$); $N^8$-phenethylnortolserine (Q=o-tolyl; E=N—$CH_2$—$CH_2$—$C_6H_5$; Z=N—$CH_3$); $N^8$-nortolserine (Q=o-tolyl; E=H; Z=N—$CH_3$); $N^1$,$N^8$-bisnortolserine (Q=o-tolyl; E=H; Z=N—H); (−)-$N^1$,$N^8$-bisbenzylnortolserine (Q=o-tolyl; E=$CH_2C_6H_5$; Z=N—$CH_2C_6H_5$); cymserine (Q=p-isopropylphenyl; E=$CH_3$; Z=N—$CH_3$); $N^1$-benzylnorcymserine (Q=p-isopropylphenyl; E=$CH_3$; Z=N—$CH_2$—$C_6H_5$); $N^1$-phenethylnorcymserine (Q=p-isopropylphenyl; E=$CH_3$; Z=N—$CH_2$—$CH_2$—$C_6H_5$); $N^1$-norcymserine (Q=p-isopropylphenyl; E=$CH_3$; Z=N—H); N8-benzylnorcymserine (Q=p-isopropylphenyl; E=N—$CH_2$—$C_6H_5$; Z=N—$CH_3$); $N^8$-phenethylnorcymserine (Q=p-isopropylphenyl; E=N—$CH_2CH_2C_6H_5$; Z=$NCH_3$); $N^8$-norcymserine (Q=p-isopropylphenyl; E=H; Z=N—$CH_3$); $N^1$,$N^8$-bisnorcymserine (Q=p-isopropylphenyl; E=H; Z=N—H); (−)-$N^1$,$N^8$-bisbenzylnorcymserine (Q=p-isopropylphenyl; E=$CH_2C_6H_5$; Z=N—$CH_2C_6H_5$); thiacymserine (Q=p-isopropylphenyl; E=$CH_3$; Z=S); thiatolserine (Q=o-tolyl; E=$CH_3$; Z=S).

Donepezil hydrochloride, rivastigmine hydrogen (2R, 3R)-tartrate and galantamine hydrobromide are the preferred AChEIs, phenserine tartrate and huperzine A also being advantageous AChEIs, for improving dementias of Alzheimer's type according to the present invention. Specifically, all the salts, solvates, analogs, derivatives and prodrugs of donepezil, rivastigmine, galantamine, phenserine and huperzine A are AChEIs useful for the method of the present invention.

According to the present invention, an AChEI, when used at a dose which is from 2.5 to 7 times the maximum recommended dose in human subjects, in particular in a patient suffering from Alzheimer type dementia, in combination with a nsPAChA at the aforementioned doses, is well tolerated and is found in the blood of said subjects at levels that are much higher than those expected for the administered doses. However, the present invention contemplates the safe administration of even higher doses of said AChEI assuring a substantially increased supply of AChEI in the CNS.

Among the preferred AChEIs, donepezil or a pharmaceutically acceptable salt thereof, in particular donepezil hydrochloride at a dose of from 25 mg to 151 mg; rivastigmine or a pharmaceutically acceptable salt thereof, in particular rivastigmine hydrogen tartrate at a dose, in rivastigmine, of from 30 mg to 126 mg; galantamine or a pharmaceutically acceptable salt thereof, in particular galantamine hydrobromide at a dose, in galantamine, of from 60 mg to 224 mg; and huperzine A at a dose of from 0.45 mg to 4.8 mg; give very high AChEI blood levels when a nsPAChA is concurrently or sequentially administered therewith at a daily dose which is from 100% to 800% the dose of said nsPAChA used in the anticholinergic therapy. In particular, said nsPAChA is selected from the group consisting of pharmaceutically acceptable salts of trospium, solifenacin and pharmaceutically acceptable salt thereof and propiverine and pharmaceutically acceptable salt thereof.

According to an advantageous embodiment, said AChEI is donepezil hydrochloride, administered at a daily dose of from 25 mg to 151 mg and said nsPAChA is solifenacin succinate, administered at a daily dose of from 10 mg to 80 mg.

According to another advantageous embodiment, said AChEI is galantamine, as hydrobromide, administered at a daily dose of from 60 mg to 224 mg, and said nsPAChA is propiverine, as hydrochloride, administered at a daily dose of from 15 mg to 240 mg.

According to a further advantageous embodiment, said AChEI is rivastigmine, as hydrogen tartrate, administered at a daily dose of from 30 mg to 126 mg, and said nsPAChA is selected from the group consisting of trospium chloride, administered at a daily dose of from 40 mg to 480 mg; glycopyrrolium bromide, administered at a daily dose of from 8 mg to 64 mg; propiverine hydrochloride, administered at a daily dose of from 15 mg to 240 mg; and solifenacin succinate, administered at a daily dose of from 10 mg to 80 mg.

The AChEIs are administered in pharmaceutical compositions wherein the active ingredient is in admixture with a pharmaceutical carrier. Said compositions may be those which are found in the commercial, brand or generic products.

In view of the high doses which can be administered according to the present invention, the AChEI may be formulated in new compositions. For example, donepezil hydrochloride may be orally administered once a day in a composition, comprising said donepezil hydrochloride in an amount of from 25 mg to 151 mg, in admixture with a pharmaceutical carrier; rivastigmine may be orally administered twice per day in a composition comprising rivastigmine hydrogen tartrate, in an amount in rivastigmine of from 15 mg to 42 mg, in admixture with a pharmaceutical carrier in an IR formulation; and galantamine may be orally administered twice per day in a composition comprising galantamine hydrobromide, in an amount in galantamine of from 40 mg to 112 mg in admixture with a pharmaceutical carrier in an IR formulation, or once a day in a pharmaceutical composition comprising galantamine hydrobromide in an amount in galantamine of from 60 mg to 224 mg in admixture with a pharmaceutical carrier in an ER formulation.

As set forth above, an overdose of an AChEI may be administered to a human subject, in particular to a patient suffering from Alzheimer type dementia without concurrent cholinergic adverse effects by concomitantly administering an nsPAChA, at the aforementioned dose, to said subject or to said patient, the sole remaining adverse effect being nausea/vomiting. This adverse effect may be alleviated by administration of a non-anticholinergic antiemetic agent (naAEA).

Any antiemetic agent substantially devoid of central anticholinergic effects may be used in order to block emesis due to the overdoses of AChEIs which are administered according to the present invention. A list of typical naAEAs adapted to this use is reported in WO 2011/034568. Advantageous naAEAs are domperidone, at a daily dose of from 10 mg to 80 mg, metoclopramide, at a daily dose of from 10 mg to 60 mg, aprepitant, at a dose of from 40 mg to 125 mg; alosetron, orally administered in 0.5-mg or in 1-mg tablets at a dose of 0.5-1 mg, once or twice a day; dolasetron mesylate, orally administered in 50-mg or in 100-mg tablets, at a daily dose of 100 mg; granisetron, orally administered orally in 1-mg or in 2-mg tablets, at a dose of 1 mg twice a day or 2 mg once a day, or parenterally administered in a 3-mg/1-ml solution for i.m. injection or in a 3 mg/3-ml solution for i.v. injection; ondansetron, orally administered in 4-mg or in 8-mg tablets at a dose of from 4 mg to 24 mg; palonosetron, administered in a 0.25-mg/5-ml solution by intravenous injection at a dose of 0.25 mg; ramosetron, orally or intravenously administered at a dose of 5 mg; and tropisetron, administered either intravenously in a 2-mg/2-ml or 5-mg/5-ml solution at a dose of 2 mg or 5 mg, or orally administered in a 5-mg capsule at a dose of 5 mg; the above doses being referred to their contents in 5-HT3-antagonist's base, unless otherwise specified.

C. The Fixed-Dose Combinations

As mentioned above, the nsPAChA may be formulated in a pharmaceutical composition also containing an AChEI.

Thus, the present invention also provides a pharmaceutical unit form particularly useful for inducing high and even very high blood concentrations of the AChEI in a human being, which comprises (a) a nsPAChA selected from the group consisting of solifenacin, pharmaceutically acceptable salts of solifenacin, propiverine, pharmaceutically acceptable salts of propiverine, trospium quaternary salts, clidinium quaternary salts, benzilonium quaternary salts and glycopyrronium quaternary salts, in an amount of from 100% to 800% the maximum amount contained in the commercial products for the anticholinergic therapy; and (b) an AChEI selected from the group consisting of (±)-2,3-dihydro-5,6-dimethoxy-2-[[1-(phenylmethyl)-4-piperidinyl]methyl]-1H-inden-1-one (donepezil) and pharmaceutically acceptable salts thereof, (S)—N-Ethyl-N-methyl-3-[1-(dimethylamino)ethyl]-phenyl carbamate (rivastigmine) and pharmaceutically acceptable salts thereof, 4aS,6R,8aS-3-methoxy-11-methyl-4a,5,9,10,11,12-hexahydroxy-6H-benzofuro[3a,3,2-e,f]benzazepin-6-ol (galantamine) and pharmaceutically acceptable salts thereof, and (1R,9S,13E)-1-amino-13-ethylidene-11-methyl-6-azatricyclo[7.3.1.0$^{2,7}$]trideca-2(7),3,10-trien-5-one (huperzine A), in an amount of from 2.5 to 7 times the maximum amount contained in the commercial products for the treatment of Alzheimer type dementia.

Preferred Component (a) is a pharmaceutically acceptable salt of trospium, especially trospium chloride, succinate, maleate, fumarate or tartrate, a pharmaceutically acceptable salt of solifenacin, especially its compound with succinic acid 1:1 (solifenacin succinate), a pharmaceutically acceptable salt of propiverine, especially its hydrochloride, a pharmaceutical acceptable salt of glycopyrronium, especially glycopyrronium bromide; a pharmaceutically acceptable salt of oxyphencyclimine, especially its hydrochloride or a pharmaceutically acceptable salt of tolterodine, especially its L-hydrogen tartrate.

Preferred Components (b) are donepezil hydrochloride, rivastigmine hydrogen tartrate, galantamine hydrobromide; and huperzine A.

More particularly, the nsPAChA Component (a) is selected from the group consisting of trospium chloride, in an amount of from 20 mg to 480 mg, advantageously from 40 mg to 480 mg, preferably from 60 mg to 480 mg per dosage unit, solifenacin succinate, in an amount of from 10 mg to 80 mg, advantageously from 15 mg to 80 mg, preferably from 20 mg to 80 mg per dosage unit; and propiverine hydrochloride, in an amount of from 15 mg to 240 mg, advantageously from 20 mg to 240 mg, preferably from 30 mg to 240 mg per dosage unit. A Component (a) selected from the group consisting of trospium chloride, in an amount of from 40 to 160 mg, preferably from 60 mg to 160 mg, in an IR formulation; propiverine hydrochloride, in an amount of from 15 mg to 120 mg, preferably from 30 mg to 120 mg, in an IR formulation, trospium chloride, in an amount of from 60 mg to 480 mg, preferably from 120 mg to 480 mg, in an ER formulation; glycopyrronium bromide; in an amount of from 4.1 to 16 mg, preferably from 4.5 to 12 mg in an IR formulation; and propiverine hydrochloride, in an amount of from 30 mg to 240 mg, preferably from 60 mg to 240 mg, in an ER formulation; is particularly advantageous.

The AChEI Component (b) is selected from the group consisting of donepezil hydrochloride, in an amount of from 25 mg to 151 mg, preferably from 57.5 to 151 mg, per dosage unit; rivastigmine, as the hydrogen tartrate thereof, in an amount of from 15 mg to 126 mg, preferably from 24 mg to 126 mg per dose unit; galantamine, as the hydrobromide thereof, in an amount of from 40 to 224 mg per dose unit; and huperzine A, in an amount of from 150 µg to 1.2 mg, preferably from 200 µg to 1.2 mg per dose unit. A Component (b) selected from the group consisting of rivastigmine (as hydrogen tartrate) in an IR oral formulation comprising from 15 mg to 42 mg of active ingredient; galantamine (as hydrobromide), in an IR formulation comprising from 40 mg to 112 mg of active ingredient; rivastigmine (as hydrogen tartrate), in an ER patch formulation releasing from 45 mg/24 hours to 126 mg/24 hours of active ingredient; and galantamine (as hydrobromide) in an ER formulation comprising from 60 mg to 168 mg of active ingredient; is particularly advantageous.

The unit form of the present invention may be a tablet, a capsule, a pre-measured volume of a liquid solution or suspension for oral administration or a patch for transdermal application. In said unit form the nsPAChA and the AChEI may be mixed together or separated according to known technologies in admixture with a pharmaceutical carrier in a pharmaceutical composition.

Component (a) and Component (b) are formulated with conventional pharmaceutical carriers in known formulations for oral use wherein said components are mixed together or separated, for example in two tablets introduced in a capsule or in a two-compartment capsule or in a multilayer (di-layer) tablet wherein the two components are both in IR or in ER form or one of the two components is in IR form and the other is in ER form, according to known technologies.

The pharmaceutical carriers and vehicles are those commonly used for the preparation of compositions for oral, buccal and parenteral, in particular transdermal, administration. Appropriate unit forms comprise the oral forms such as tablets, soft or hard gelatin capsules, powders or granulates in sachets and suitably measured oral solutions or suspensions as well as patches for transdermal administration.

Component (a) and component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and component (b) may also be formulated in the form of microcapsules, optionally with one or more carriers or additives.

For oral administration, Component (a) and Component (b), together or separately, are formulated by mixing the active ingredient with conventional pharmaceutical acceptable carriers enabling said active ingredients to be formulated in tablets, dragees, orally disintegrating tablets, capsules, liquid solutions or suspensions, syrups and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubrifiants such as polyethylenglycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

Carriers for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The composition according to the present invention may be in form of a capsule containing two tablets as described herein above, one of them comprising Component (a) and the other comprising Component (b).

The association nsPAChA/AChEI may be formulated in tablets in which one or both of the two components is in controlled-release formulation, for example as a dispersion of said component in hydroxypropyl methyl cellulose or in a film-coated microgranule. Advantageously, the AChEI, in a ER-formulation is in the core and the nsPAChA, in IR-formulation, is in the outer layer in multi-layer tablets in which, for example, both the core and the outer layer are coated with a film. Analogously, capsules made of two separated parts, one containing Component (a), in IR- or ER-formulation and the other containing Component (b), in IR- or ER-formulation, may be used.

Carriers and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylceluloses, methylcellulose, ethylcellulose, or sodium carboxymethylcellulose; gums; waxes; glycerides or aliphatic alcohols or a mixture thereof.

In particular, the unit forms of the present invention comprise a member selected from the group consisting of trospium chloride, solifenacin succinate and propiverine hydrochloride, as an nsPAChA and a member selected from the group consisting of donepezil hydrochloride, in an amount of from 25 mg to 151 mg; rivastigmine hydrogen tartrate; in an amount in rivastigmine of from 15 mg to 42 mg; galantamine hydrobromide, in an amount in galantamine of from 40 to 112 mg; and huperzine A, in an amount of from 150 µg to 1.2 mg as an AChEI.

According to an embodiment, the compositions of the present invention are formulated by mixing the Component (a) and the Component (b) together, in admixture with a pharmaceutical carrier for an immediate or extended release and are useful for inducing increased AChEI plasma concentrations in a human subject or in a patient suffering from a dementia of Alzheimer type treated with said AChEI.

An advantageous composition according to this embodiment comprises from 20 mg to 160 mg preferably from 80 mg to 160 mg; of trospium chloride, as Component (a); and
 from 15 mg to 42 mg, preferably form 18 mg to 42 mg, of rivastigmine (as hydrogen tartrate); or
 from 40 mg to 84 mg preferably from 42 mg to 84 mg, of galantamine (as hydrobromide), as Component (b),
wherein Components (a) and (b) are mixed together and with a pharmaceutical carrier in an IR formulation.

Another advantageous composition according to this embodiment comprises
 from 10 mg to 80 mg, preferably from 20 mg to 80 mg, of solifenacin succinate, as Component (a); and
 from 25 mg to 70 mg, preferably from 40 mg to 70 mg, of donepezil hydrochloride, as Component (b),
wherein Components (a) and (b) are mixed together and with a pharmaceutical carrier in an IR formulation.

A particular composition according to this embodiment comprises
 15 mg of solifenacin succinate, as Component (a); and
 from 40 mg to 60 mg of donepezil hydrochloride, as Component (b),
wherein Components (a) and (b) are mixed together and with a pharmaceutical carrier in an IR formulation.

A further advantageous composition according to this embodiment comprises
 from 15 mg to 120 mg, preferably from 30 mg to 120 mg of propiverine hydrochloride, as Component (a); and
 from 15 mg to 42 mg, preferably form 18 mg to 42 mg, of rivastigmine (as hydrogen tartrate); or
 from 40 mg to 112 mg preferably from 42 mg to 112 mg, of galantamine (as hydrobromide), as Component (b),
wherein Components (a) and (b) are mixed together and with a pharmaceutical carrier in an IR formulation.

A particular composition according to this embodiment comprises
 30 mg of propiverine hydrochloride, as Component (a); and
 25 mg of rivastigmine (as hydrogen tartrate), as Component (b),
wherein Components (a) and (b) are mixed together and with a pharmaceutical carrier in an IR formulation.

Another particular composition according to this embodiment comprises
 45 mg of propiverine hydrochloride, as Component (a); and
 60 mg of galantamine (as hydrobromide), as Component (b),
wherein Components (a) and (b) are mixed together and with a pharmaceutical carrier in an ER formulation.

According to another embodiment, the compositions of the present invention are formulated by mixing the Component (a) with a pharmaceutical carrier for an immediate or extended release in tablets (Tablet A) and the Component (b), separately, with a pharmaceutical carrier for an immediate or extended release in tablets (Tablet B) and introducing Tablet A and Tablet B in a capsule for oral administration as described for example in GB 1204580 or in US 2007/

0224259. An advantageous composition according to this embodiment consists of soft or hard gelatin capsules each containing Tablet A comprising from 15 mg to 40 mg of propiverine hydrochloride, as Component (a), in admixture with a pharmaceutical carrier in a IR formulation; and Tablet B, comprising from 25 mg to 35 mg of rivastigmine (as hydrogen tartrate); as Component (b), in admixture with a pharmaceutical carrier in an IR-formulation.

Another advantageous composition according to this embodiment consists of soft or hard gelatin capsules each containing Tablet A comprising from 2 mg to 16 mg of glycopyrrolium bromide, as Component (a), in admixture with a pharmaceutical carrier in a IR formulation; and Tablet B, comprising from 25 mg to 42 mg of rivastigmine (as hydrogen tartrate); as Component (b), in admixture with a pharmaceutical carrier in an IR-formulation.

A further advantageous composition according to this embodiment consists of soft or hard gelatin capsules each containing Tablet A comprising from 4 mg of glycopyrrolium bromide, as Component (a), in admixture with a pharmaceutical carrier in a IR formulation; and Tablet B, 30 mg of rivastigmine (as hydrogen tartrate); as Component (b), in admixture with a pharmaceutical carrier in an IR-formulation.

According to a further embodiment, the compositions according to the present invention are formulated in a di-layer tablet which releases two drug doses, in which the release of a drug from one drug-containing layer does not interfere with the release of a drug from the other drug-containing layer as described for example in WO 2006/089493. An advantageous composition according to this embodiment consists of Layer A, comprising from 10 mg to 40 mg of solifenacin succinate, as Component (a), in admixture with a pharmaceutical carrier in a IR formulation and Layer B, comprising from 25 mg to 50 mg of donepezil hydrochloride, as Component (b), in admixture with a pharmaceutical carrier in an IR-formulation.

According to another embodiment, the compositions of the present invention are formulated in patch for transdermal administration. Particularly advantageous compositions according to this embodiment are transdermal patch formulations comprising from 60 mg/24 hours to 480 mg/24 hours, preferably from 160 mg/24 hours to 480 mg/24 hours, of trospium chloride, as Component (a); and from 45 mg/24 hours to 126 mg/24 hours, preferably from 90 mg/24 hours to 126 mg/24 hours, of rivastigmine (as hydrogen tartrate), as Component (b), with a pharmaceutically acceptable carrier or diluent which is suitable for systemic transdermal administration.

Another embodiment of the present invention provides unit forms consisting of tablets comprising from 10 mg to 15 mg, of solifenacin succinate, as Component (a); and from 25 mg to 50 mg preferably from 37.5 mg to 50 mg, of donepezil hydrochloride;

as Component (b), in admixture with a pharmaceutical carrier in a IR-formulation for oral administration.

According to a preferred embodiment, the invention provides unit forms consisting of tablets comprising 20 mg of solifenacin succinate, as Component (a) and from 25 mg to 50 mg preferably from 37.5 mg to 50 mg, of donepezil hydrochloride, as Component (b), in admixture with a pharmaceutical carrier, in a formulation for oral administration to be administered once a day.

Another preferred embodiment of the invention provides unit forms for oral administration consisting of tablets comprising from 10 mg to 80 mg of solifenacin succinate, as Component (a) and from 25 mg to 151 mg preferably from 57.5 mg to 151 mg, of donepezil hydrochloride, as Component (b), in admixture with a pharmaceutical carrier, in formulation for oral administration to be administered once a day.

IV. A Fourth Aspect of the Present Invention

A fourth aspect of the present invention provides a pharmaceutical composition comprising solifenacin or a pharmaceutically acceptable salt or compound thereof, and a naAEA, in admixture with a pharmaceutical carrier.

More particularly, it is an object of the present invention to provide a composition comprising (a) (1S)-(3R)-1-azabicyclo[2.2.2]oct-3-yl 3,4-dihydro-1-phenyl-2(1H)-isoquinolinecarboxylate (solifenacin) or a pharmaceutically acceptable salt or compound thereof, in an amount which is equivalent to from 10 mg to 80 mg of solifenacin succinate; and (b) a naAEA; in admixture with a pharmaceutical.

Solifenacin and pharmaceutically acceptable salts and compounds thereof, including the quaternary ammonium salts thereof, and their preparation are described in U.S. Pat. No. 6,017,927. Methods for the preparation and for the purification of solifenacin and its salts, in particular of solifenacin succinate, are described for example in WO 2007/076116, WO 2009/139002, WO 2011/003624 and WO 2012/001481.

Advantageously, Component (a) of the composition is solifenacin succinate, in an amount of from 10 mg to 80 mg, advantageously from 11 mg to 80 mg, more advantageously from to 15 mg to 80 mg, preferably from 21 mg to 80 mg, most preferably from 21 mg to 40 mg.

The naAEA Component (b) is present in an amount of from 100% to 300% of the amount of the said naAEA contained as a sole active ingredient in the currently used brand or generic drugs.

According to a preferred embodiment, said Component (b) is a non-anticholinergic antiemetic agent selected from the group consisting of (b1) 5HT3-antagonists, (b2) DA-antagonists, (b3) H1-antagonists, (b4) cannabinoids, (b5) aprepitant. Typical naAEAs of the above classes are illustrated in WO 2011/034568.

An advantageous Component (b) is selected from the group consisting of alosetron and pharmaceutically acceptable salts and solvates thereof, in particular the hydrochloride, in an amount (in alosetron) of from 0.5 mg to 3 mg; dolasetron and pharmaceutically acceptable salts and solvates thereof, in particular the mesylate, in an amount (in dolasetron) of from 50 mg to 300 mg; granisetron and pharmaceutically acceptable salts and solvates thereof, in particular the hydrochloride, in an amount (in granisetron) of from 1 mg to 3 mg; ondansetron and pharmaceutically acceptable salts and solvates thereof, in particular the hydrochloride dihydrate, in an amount (in ondansetron) of from 4 mg to 24 mg; tropisetron and pharmaceutically acceptable salts and solvates thereof, in particular the hydrochloride, in an amount of from 5 mg to 15 mg; domperidone and pharmaceutically acceptable salts and solvates thereof, in an amount (in domperidone) of from 10 mg to 30 mg; haloperidol, in an amount of from 1 mg to 30 mg; chlorpromazine and pharmaceutically acceptable salts and solvates thereof, in particular the hydrochloride, in an amount (in chlorpromazine) of from 25 mg to 75 mg; prochlorperazine and pharmaceutically acceptable salts and solvates thereof, in particular the dimaleate, in an amount (in prochlorperazine) of from 5 mg to 30 mg; metoclopramide and pharmaceutically acceptable salts and solvates thereof, in particular the monohydrochloride monohydrate, in an amount (in metoclopramide) of from 10 mg to 30 mg; bromopride and pharmaceutically acceptable salts and solvates, in particular the monohydrochloride and the dihydrochloride monohydrate, in an amount (in bromopride) of from 10 mg to 30 mg; clebopride and pharmaceutically acceptable salts and solvates thereof, in particular the hydrogen malate and the hydrochloride monohydrate, in an amount (in clebopride) of from 0.5 mg to 1.5 mg; levosulpiride, in an amount of from 25 mg to 300 mg; alizapride and pharmaceutically acceptable salts thereof, in particular the hydrochloride, in an amount (in alizapride) of from 50 mg to 150 mg; trimethobenzamide and pharmaceutically acceptable salts thereof such as the monohydrochloride, in an amount (in trimethobenzamide) of from 300 mg to 900 mg; meclizine and pharmaceutically acceptable salts and solvates thereof, in an amount (in meclizine) of from 13 mg to 150 mg; promethazine and pharmaceutically acceptable salts and solvates thereof, in particular the hydrochloride, in an amount (in prometazine) of from 25 mg to 150 mg; dronabinol in an amount of from 2.5 mg to 60 mg; nabilone, in an amount of from 2 mg to 12 mg; and aprepitant, in an amount of from 40 mg to 375 mg.

An advantageous non-anticholinergic antiemetic agent Component (b) in said pharmaceutical composition is selected from the group consisting of alosetron and pharmaceutically acceptable salts and solvates thereof, in an amount (in alosetron) of from 0.5 mg to 3 mg; dolasetron and pharmaceutically acceptable salts thereof, in an amount (in dolasetron) of from 50 mg to 300 mg; granisetron and pharmaceutically acceptable salts thereof, in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg; bromopride and pharmaceutically acceptable salts and solvates thereof, in an amount (in bromopride) of from 10 mg to 30 mg; clebopride and pharmaceutically acceptable salts thereof, in an amount (in clebopride) of from 0.5 mg to 1.5 mg; and aprepitant, in an amount of from 40 mg to 375 mg.

Preferred Component (b) is a naAEA selected from the group consisting of alosetron and pharmaceutically acceptable salts and solvates thereof, in an amount (in alosetron) of from 0.5 mg to 3 mg; granisetron and pharmaceutically acceptable salts and solvates thereof, in particular the hydrochloride, in an amount (in granisetron) of from 1 mg to 3 mg; ondansetron and pharmaceutically acceptable salts and solvates thereof, in an amount (in ondansetron) of from 4 mg to 24 mg; tropisetron and pharmaceutically acceptable salts thereof, in an amount (in tropisetron) of from 5 mg to 15 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg.

A composition comprising (a) solifenacin succinate in an amount of from 10 mg to 80 mg, advantageously from 1 mg to 80 mg, more advantageously from to 15 mg to 80 mg, preferably from 21 mg to 80 mg, most preferably from 21 mg to 40 mg; and (b); and a naAEA selected from the group consisting of granisetron hydrochloride in an amount (in granisetron) of from 1 mg to 3 mg, ondansetron hydrochloride dihydrate in an amount (in ondansetron) of from 4 mg to 24 mg, domperidone in an amount of from 10 mg to 30 mg; and metoclopramide monohydrochloride monohydrate in an amount (in metoclopramide) of from 10 mg to 30 mg; and aprepitant, in an amount of from 40 mg to 375 mg, in admixture with a pharmaceutical carrier, is an advantageous embodiment of the present invention; the same composition, wherein Component (a) is solifenacin succinate in an amount of from 10 mg to 30 mg, from 15 mg to 30 mg or from 21 mg to 30 mg being particularly preferred.

The pharmaceutical compositions of the present invention are formulated in unit form for oral use, preferably in an immediate release formulation.

The unit form of the present invention may be a tablet, a capsule, or a pre-measured amount of granulate for oral administration comprising Component (a) and Component (b) in admixture with a pharmaceutical carrier. In said unit form solifenacin and the naAEA may be mixed together or separated according to known technologies in admixture with a pharmaceutical carrier in a pharmaceutical composition.

Component (a) and Component (b) are formulated with conventional pharmaceutical carriers in known formulations for oral use wherein said components are mixed together or separated, for example in two tablets introduced in a capsule or in a two-compartment capsule or in a multilayer (di-layer) tablet wherein the two components are both in IR form, even though in one of the layers, Component (a) is in IR form and Component (b) may be in ER form, according to known technologies.

The pharmaceutical carriers and vehicles are those commonly used for the preparation of compositions for oral, buccal and parenteral, in particular transdermal, administration. Appropriate unit forms comprise the oral forms such as tablets, soft or hard gelatin capsules, powders or granulates in sachets and suitably measured oral solutions or suspensions as well as patches for transdermal administration.

Component (a) and Component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and Component (b) may also be formulated in the form of microcapsules, optionally with one or more carriers or additives.

For oral administration, Component (a) and Component (b), together or separately, are formulated by mixing the active ingredient with conventional pharmaceutical acceptable carriers enabling said active ingredients to be formulated in tablets, dragees, orally disintegrating tablets, capsules and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubrifiants such as polyethylenglycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

The sweeteners contained in the orally disintegrating tablets may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The composition according to the present invention may be in form of a capsule containing two tablets as described herein above, one of them comprising Component (a) and the other comprising Component (b).

The association solifenacin/naAEA may be formulated in tablets in which one or both of the two components is in controlled-release formulation, for example as a dispersion of said component in hydroxypropyl methyl cellulose or in a film-coated microgranule. In this case the naAEA, in an ER-formulation, is in the core and the nsPAChA, in IR-formulation, is in the outer layer in multi-layer tablets in which, for example, both the core and the outer layer are coated with a film. Analogously, capsules made of two separated parts, one containing Component (a), in IR-formulation and the other containing Component (b), in IR- or ER-formulation, may be used.

Advantageous ER administration formulations are in form of a transdermal patch manufactured according to known technologies, for administering the solifenacin/antiemetic composition continuously and transdermally through a selected area of intact skin in a controlled manner for a prolonged period of time to induce high AChEI blood levels in a human subject, in particular to a patient suffering from a dementia of Alzheimer type, said subject or patient being treated with said AChEI. Said high AChEI blood levels enable AChEI concentrations in the brain to rise sufficiently to afford neuroprotection.

Carriers and vehicles for ER formulations include retardant materials such as acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

In particular, the unit forms of the present invention comprise solifenacin succinate, in an amount of from 10 to 80 mg and a member selected from the group consisting of domperidone, in an amount of from 10 mg to 30 mg; metoclopramide monohydrochloride monohydrate, in an amount (in metoclopramide) of from 10 mg to 30 mg; alosetron hydrochloride, in an amount, in alosetron of from 0.5-mg to 3 mg), dolasetron mesylate, in an amount of from 50 mg to 300 mg; granisetron hydrochloride in an amount, in granisetron, of from 1 mg to 3 mg; ondansetron hydrochloride monohydrate in an amount, in ondansetron, of from 4 to 24 mg; tropisetron hydrochloride in an amount, in tropisetron, of from 5 mg to 15 mg; and aprepitant, in an amount of from 40 mg to 375 mg.

According to an embodiment, the compositions of the present invention are formulated by mixing solifenacin succinate, as Component (a), and the naAEA, as Component (b), together with a pharmaceutical carrier and compressed to a tablet for an immediate release or introduced in a soft or hard capsule for an immediate release.

An advantageous solifenacin/granisetron composition according to this embodiment comprises
    from 10 mg to 80 mg of solifenacin succinate, as Component (a); and
    from 1 mg to 3 mg of granisetron (as hydrochloride);
as mixed together and with a pharmaceutical carrier in an IR formulation.

A first particularly advantageous solifenacin/granisetron composition comprises
    10 mg of solifenacin succinate, as Component (a); and
    1 mg of granisetron (as hydrochloride), as Component (b),
as mixed together and with a pharmaceutical carrier in an IR formulation.

A second particularly advantageous solifenacin/granisetron composition according to this embodiment comprises
    15 mg of solifenacin succinate, as Component (a); and
    1 mg of granisetron (as hydrochloride), as Component (b),
as mixed together and with a pharmaceutical carrier in an IR formulation.

A third advantageous solifenacin/granisetron composition according to this embodiment comprises
    21 mg of solifenacin succinate, as Component (a); and
    1 mg of granisetron (as hydrochloride), as Component (b),
as mixed together and with a pharmaceutical carrier in an IR formulation.

A fourth advantageous solifenacin/granisetron composition according to this embodiment comprises
    25 mg of solifenacin succinate, as Component (a); and
    1 mg of granisetron (as hydrochloride), as Component (b),
as mixed together and with a pharmaceutical carrier in an IR formulation.

A fifth advantageous solifenacin/granisetron composition according to this embodiment comprises
    25 mg of solifenacin succinate, as Component (a); and
    2 mg of granisetron (as hydrochloride), as Component (b),
as mixed together and with a pharmaceutical carrier in an IR formulation.

A sixth advantageous solifenacin/granisetron composition according to this embodiment comprises
    40 mg of solifenacin succinate, as Component (a); and
    2 mg of granisetron (as hydrochloride), as Component (b),
as mixed together and with a pharmaceutical carrier in an IR formulation.

A seventh advantageous solifenacin/granisetron composition according to this embodiment comprises
    80 mg of solifenacin succinate, as Component (a); and
    3 mg of granisetron (as hydrochloride), as Component (b),
as mixed together and with a pharmaceutical carrier in an IR formulation.

An advantageous solifenacin/ondansetron composition according to this embodiment comprises
    from 10 mg to 80 mg of solifenacin succinate, as Component (a); and
    from 4 mg to 24 mg of ondansetron (as hydrochloride dihydrate);
as mixed together and with a pharmaceutical carrier in an IR formulation.

A first particularly advantageous solifenacin/ondansetron composition according to this embodiment comprises 10 mg of solifenacin succinate, as Component (a); and
4 mg of ondansetron (as hydrochloride dihydrate), as Component (b),
as mixed together and with a pharmaceutical carrier in an IR formulation.

A second particularly advantageous solifenacin/ondansetron composition according to this embodiment comprises
15 mg of solifenacin succinate, as Component (a); and
4 mg of ondansetron (as hydrochloride dihydrate), as Component (b),
as mixed together and with a pharmaceutical carrier in an IR formulation.

A third advantageous solifenacin/ondansetron composition according to this embodiment comprises
21 mg of solifenacin succinate, as Component (a); and
4 mg of ondansetron (as hydrochloride dihydrate), as Component (b),
as mixed together and with a pharmaceutical carrier in an IR formulation.

A fourth advantageous solifenacin/ondansetron composition according to this embodiment comprises
25 mg of solifenacin succinate, as Component (a); and
4 mg of ondansetron (as hydrochloride dihydrate), as Component (b),
as mixed together and with a pharmaceutical carrier in an IR formulation.

A fifth advantageous solifenacin/ondansetron composition according to this embodiment comprises
25 mg of solifenacin succinate, as Component (a); and
8 mg of ondansetron (as hydrochloride dihydrate), as Component (b),
as mixed together and with a pharmaceutical carrier in an IR formulation.

A sixth advantageous solifenacin/ondansetron composition according to this embodiment comprises
40 mg of solifenacin succinate, as Component (a); and
8 mg of ondansetron (as hydrochloride dihydrate), as Component (b),
as mixed together and with a pharmaceutical carrier in an IR formulation.

A seventh advantageous solifenacin/ondansetron composition according to this embodiment comprises
80 mg of solifenacin succinate, as Component (a); and
20 mg of ondansetron (as hydrochloride dihydrate), as Component (b),
as mixed together and with a pharmaceutical carrier in an IR formulation.

An advantageous solifenacin/tropisetron composition according to this embodiment comprises
from 10 mg to 80 mg of solifenacin succinate, as Component (a); and
from 5 mg to 15 mg of tropisetron (as hydrochloride), as Component (b);
as mixed together and with a pharmaceutical carrier in an IR formulation.

A first particularly advantageous solifenacin/tropisetron composition according to this embodiment comprises
10 mg of solifenacin succinate, as Component (a); and
5 mg of tropisetron (as hydrochloride), as Component (b),
as mixed together and with a pharmaceutical carrier in an IR formulation.

A second particularly advantageous solifenacin/tropisetron composition according to this embodiment comprises
15 mg of solifenacin succinate, as Component (a); and
5 mg of tropisetron (as hydrochloride), as Component (b),
as mixed together and with a pharmaceutical carrier in an IR formulation.

A third advantageous solifenacin/tropisetron composition according to this embodiment comprises
21 mg of solifenacin succinate, as Component (a); and
5 mg of tropisetron (as hydrochloride), as Component (b),
as mixed together and with a pharmaceutical carrier in an IR formulation.

A fourth advantageous solifenacin/tropisetron composition according to this embodiment comprises
25 mg of solifenacin succinate, as Component (a); and
5 mg of tropisetron (as hydrochloride), as Component (b),
as mixed together and with a pharmaceutical carrier in an IR formulation.

A fifth advantageous solifenacin/tropisetron composition according to this embodiment comprises
25 mg of solifenacin succinate, as Component (a); and
10 mg of tropisetron (as hydrochloride), as Component (b),
as mixed together and with a pharmaceutical carrier in an IR formulation.

A sixth advantageous solifenacin/tropisetron composition according to this embodiment comprises
40 mg of solifenacin succinate, as Component (a); and
10 mg of tropisetron (as hydrochloride), as Component (b),
as mixed together and with a pharmaceutical carrier in an IR formulation.

A seventh advantageous solifenacin/tropisetron composition according to this embodiment comprises
80 mg of solifenacin succinate, as Component (a); and
15 mg of tropisetron (as hydrochloride), as Component (b),
as mixed together and with a pharmaceutical carrier in an IR formulation.

An advantageous solifenacin/dolasetron composition according to this embodiment comprises
from 10 mg to 80 mg of solifenacin succinate, as Component (a); and
from 50 mg to 300 mg of dolasetron (as mesylate), as Component (b);
as mixed together and with a pharmaceutical carrier in an IR formulation.

A particular advantageous solifenacin/dolasetron composition according to this embodiment comprises
15 mg, 17.5 mg or 21 mg of solifenacin succinate, as Component (a); and
50 mg of dolasetron (as mesylate), as Component (b);
as mixed together and with a pharmaceutical carrier in an IR formulation.

An advantageous solifenacin/alosetron composition according to this embodiment comprises
from 10 mg to 80 mg of solifenacin succinate, as Component (a); and
from 0.5 mg to 3 mg of alosetron (as mesylate), as Component (b);
as mixed together and with a pharmaceutical carrier in an IR formulation.

A particular advantageous solifenacin/alosetron composition according to this embodiment comprises
15 mg, 17.5 mg or 21 mg of solifenacin succinate, as Component (a); and
2 mg of alosetron (as mesylate), as Component (b);
as mixed together and with a pharmaceutical carrier in an IR formulation.

An advantageous solifenacin/domperidone composition according to this embodiment comprises
from 10 mg to 80 mg of solifenacin succinate, as Component (a); and from 10 mg to 30 mg of domperidone, as Component (b); as mixed together and with a pharmaceutical carrier in an IR formulation.

A first particularly advantageous solifenacin/domperidone composition according to this embodiment comprises
- 10 mg of solifenacin succinate, as Component (a); and
- 10 mg of domperidone, as Component (b), as mixed together and with a pharmaceutical carrier in an IR formulation.

A second particularly advantageous solifenacin/domperidone composition according to this embodiment comprises
- 15 mg of solifenacin succinate, as Component (a); and
- 10 mg of domperidone, as Component (b), as mixed together and with a pharmaceutical carrier in an IR formulation.

A third advantageous solifenacin/domperidone composition according to this embodiment comprises
- 21 mg of solifenacin succinate, as Component (a); and
- 10 mg of domperidone, as Component (b), as mixed together and with a pharmaceutical carrier in an IR formulation.

A fourth advantageous solifenacin/domperidone composition according to this embodiment comprises
- 25 mg of solifenacin succinate, as Component (a); and
- 10 mg of domperidone, as Component (b), as mixed together and with a pharmaceutical carrier in an IR formulation.

A fifth advantageous solifenacin/domperidone composition according to this embodiment comprises
- 25 mg of solifenacin succinate, as Component (a); and
- 20 mg of domperidone, as Component (b), as mixed together and with a pharmaceutical carrier in an IR formulation.

A sixth advantageous solifenacin/domperidone composition according to this embodiment comprises
- 40 mg of solifenacin succinate, as Component (a); and
- 20 mg of domperidone, as Component (b), as mixed together and with a pharmaceutical carrier in an IR formulation.

A seventh advantageous solifenacin/domperidone composition according to this embodiment comprises
- 80 mg of solifenacin succinate, as Component (a); and
- 30 mg of domperidone, as Component (b), as mixed together and with a pharmaceutical carrier in an IR formulation.

An advantageous solifenacin/metoclopramide composition according to this embodiment comprises
- from 10 mg to 80 mg of solifenacin succinate, as Component (a); and
- from 10 mg to 30 mg of metoclopramide, as Component (b);

as mixed together and with a pharmaceutical carrier in an IR formulation.

A first particularly advantageous composition according to this embodiment comprises
- 10 mg of solifenacin succinate, as Component (a); and
- 10 mg of metoclopramide (as monohydrochloride monohydrate), as Component (b), as mixed together and with a pharmaceutical carrier in an IR formulation.

A second particularly advantageous composition according to this embodiment comprises
- 15 mg of solifenacin succinate, as Component (a); and
- 10 mg of metoclopramide (as monohydrochloride monohydrate), as Component (b), as mixed together and with a pharmaceutical carrier in an IR formulation.

A third advantageous composition according to this embodiment comprises
- 21 mg of solifenacin succinate, as Component (a); and
- 10 mg of metoclopramide (as monohydrochloride monohydrate), as Component (b), as mixed together and with a pharmaceutical carrier in an IR formulation.

A fourth advantageous composition according to this embodiment comprises
- 25 mg of solifenacin succinate, as Component (a); and
- 10 mg of metoclopramide (as monohydrochloride monohydrate), as Component (b), as mixed together and with a pharmaceutical carrier in an IR formulation.

A fifth advantageous composition according to this embodiment comprises
- 25 mg of solifenacin succinate, as Component (a); and
- 20 mg of domperidone, as Component (b), A sixth advantageous composition according to this embodiment comprises
- 40 mg of solifenacin succinate, as Component (a); and
- 20 mg of metoclopramide (as monohydrochloride monohydrate), as Component (b), as mixed together and with a pharmaceutical carrier in an IR formulation.

A seventh advantageous composition according to this embodiment comprises
- 80 mg of solifenacin succinate, as Component (a); and
- 30 mg of metoclopramide (as monohydrochloride monohydrate), as Component (b), as mixed together and with a pharmaceutical carrier in an IR formulation.

According to a second embodiment, the compositions of the present invention are formulated by mixing solifenacin succinate, as the Component (a) with a pharmaceutical carrier for an immediate or extended release in tablets (Tablet A) and the naAEA Component (b), separately, with a pharmaceutical carrier for an immediate or extended release in tablets (Tablet B) and introducing Tablet A and Tablet B in a capsule for oral administration as described for example in GB 1204580 or in US 2007/0224259, thus obtaining a unit form to be administered to a patient suffering from a dementia of Alzheimer type.

An advantageous solifenacin/granisetron unit form according to this embodiment consists of preferably hard gelatin capsules each containing
- Tablet A comprising from 10 mg to 80 mg of solifenacin succinate, as Component (a), in admixture with a pharmaceutical carrier in a IR formulation; and
- Tablet B, comprising from 1 to 3 mg of granisetron (as hydrochloride), as Component (b), in admixture with a pharmaceutical carrier in an IR-formulation.

A first particularly advantageous solifenacin/granisetron unit form according to this embodiment contains
- Tablet A comprising 10 mg of solifenacin succinate, as Component (a), in admixture with a pharmaceutical carrier in a IR formulation; and
- Tablet B, comprising 1 mg of granisetron (as hydrochloride), as Component (b), in admixture with a pharmaceutical carrier in an IR-formulation.

A second particularly advantageous solifenacin/granisetron unit form according to this embodiment contains
- Tablet A comprising 10 mg of solifenacin succinate, as Component (a), in admixture with a pharmaceutical carrier in a IR formulation; and Tablet B, comprising 2 mg of granisetron (as hydrochloride), as Component (b), in admixture with a pharmaceutical carrier in an IR-formulation.

A third advantageous solifenacin/granisetron unit form according to this embodiment contains
  Tablet A comprising 10 mg of solifenacin succinate, as Component (a), in admixture with a pharmaceutical carrier in a IR formulation; and
  Tablet B, comprising 3 mg of granisetron (as hydrochloride), as Component (b), in admixture with a pharmaceutical carrier in an IR-formulation.

An advantageous solifenacin/ondansetron unit form according to this embodiment consists of preferably hard gelatin capsules each containing
  Tablet A comprising from 10 mg to 80 mg of solifenacin succinate, as Component (a), in admixture with a pharmaceutical carrier in a IR formulation; and
  Tablet B, comprising from 4 to 24 mg of ondansetron (as hydrochloride dihydrate), as Component (b), in admixture with a pharmaceutical carrier in an IR-formulation.

A first particularly advantageous solifenacin/ondansetron unit form according to this embodiment contains
  Tablet A comprising 10 mg of solifenacin succinate, as Component (a), in admixture with a pharmaceutical carrier in a IR formulation; and
  Tablet B, comprising 4 mg of granisetron (as hydrochloride dihydrate), as Component (b), in admixture with a pharmaceutical carrier in an IR-formulation.

A second particularly advantageous solifenacin/ondansetron unit form according to this embodiment contains
  Tablet A comprising 10 mg of solifenacin succinate, as Component (a), in admixture with a pharmaceutical carrier in a IR formulation; and
  Tablet B, comprising 8 mg of ondansetron (as hydrochloride dihydrate), as Component (b), in admixture with a pharmaceutical carrier in an IR-formulation.

A third advantageous solifenacin/ondansetron unit form according to this embodiment contains
  Tablet A comprising 15 mg of solifenacin succinate, as Component (a), in admixture with a pharmaceutical carrier in a IR formulation; and
  Tablet B, comprising 8 mg of ondansetron (as hydrochloride dihydrate), as Component (b), in admixture with a pharmaceutical carrier in an IR-formulation.

An advantageous solifenacin/tropisetron unit form according to this embodiment consists of preferably hard gelatin capsules each containing
  Tablet A comprising from 10 mg to 80 mg of solifenacin succinate, as Component (a), in admixture with a pharmaceutical carrier in a IR formulation; and
  Tablet B, comprising from 5 to 15 mg of tropisetron as Component (b), in admixture with a pharmaceutical carrier in an IR-formulation.

A first particularly advantageous solifenacin/granisetron unit form according to this embodiment contains
  Tablet A comprising 10 mg of solifenacin succinate, as Component (a), in admixture with a pharmaceutical carrier in a IR formulation; and
  Tablet B, comprising 5 mg of tropisetron (as hydrochloride), as Component (b), in admixture with a pharmaceutical carrier in an IR-formulation.

A second particularly advantageous solifenacin/tropisetron unit form according to this embodiment contains
  Tablet A comprising 15 mg of solifenacin succinate, as Component (a), in admixture with a pharmaceutical carrier in a IR formulation; and
  Tablet B, comprising 5 mg of tropisetron (as hydrochloride), as Component (b), in admixture with a pharmaceutical carrier in an IR-formulation.

An advantageous solifenacin/domperidone unit form according to this embodiment consists of preferably hard gelatin capsules each containing
  Tablet A comprising from 10 mg to 80 mg of solifenacin succinate, as Component (a), in admixture with a pharmaceutical carrier in a IR formulation; and
  Tablet B, comprising from 10 to 30 mg of domperidone as Component (b), in admixture with a pharmaceutical carrier in an R-formulation.

A particularly advantageous solifenacin/domperidone unit form according to this embodiment contains
  Tablet A comprising 10 mg of solifenacin succinate, as Component (a), in admixture with a pharmaceutical carrier in a IR formulation; and
  Tablet B, comprising 10 mg of domperidone as Component (b), in admixture with a pharmaceutical carrier in an IR-formulation.

An advantageous solifenacin/metoclopramide unit form according to this embodiment consists of preferably hard gelatin capsules each containing
  Tablet A comprising from 10 mg to 80 mg of solifenacin succinate, as Component (a), in admixture with a pharmaceutical carrier in a IR formulation; and
  Tablet B, comprising from 10 to 30 mg of metoclopramide (as monohydrochloride monohydrate) as Component (b), in admixture with a pharmaceutical carrier in an IR-formulation.

A particularly advantageous solifenacin/metoclopramide unit form according to this embodiment contains
  Tablet A comprising 10 mg of solifenacin succinate, as Component (a), in admixture with a pharmaceutical carrier in a IR formulation; and
  Tablet B, comprising 10 mg of metoclopramide (as monohydrochloride monohydrate) as Component (b), in admixture with a pharmaceutical carrier in an IR-formulation.

According to a third embodiment, the compositions according to the present invention are formulated in a di-layer tablet, one comprising from 10 mg to 80 mg of solifenacin succinate and the other comprising a naAEA, which releases the two drug doses, in which the release of a drug from one drug-containing layer does not interfere with the release of a drug from the other drug-containing layer as described for example in WO 2006/089493.

An advantageous solifenacin/granisetron composition according to this embodiment consists of
  Layer A, comprising from 10 mg to 80 mg of solifenacin succinate, as Component (a), in admixture with a pharmaceutical carrier in a IR formulation and
  Layer B, comprising from 1 to 3 mg of granisetron, as hydrochloride, as Component (b), in admixture with a pharmaceutical carrier in an IR-formulation.

A first particularly advantageous solifenacin/granisetron composition according to this embodiment consist of
  Layer A, comprising 10 mg of solifenacin succinate, as Component (a), in admixture with a pharmaceutical carrier in a IR formulation and
  Layer B, comprising 1 mg of granisetron, as hydrochloride, as Component (b), in admixture with a pharmaceutical carrier in an IR-formulation.

A second particularly advantageous solifenacin/granisetron composition according to this embodiment consist of Layer A, comprising 10 mg of solifenacin succinate, as Component (a), in admixture with a pharmaceutical carrier in a IR formulation and Layer B, comprising 2 mg of granisetron, as hydrochloride, as Component (b), in admixture with a pharmaceutical carrier in an R-formulation.

A third particularly advantageous solifenacin/granisetron composition according to this embodiment consist of Layer A, comprising 10 mg of solifenacin succinate, as Component (a), in admixture with a pharmaceutical carrier in a IR formulation and Layer B, comprising 2 mg of granisetron, as hydrochloride, as Component (b), in admixture with a pharmaceutical carrier in an IR-formulation.

An advantageous solifenacin/ondansetron composition according to this embodiment consists of Layer A, comprising from 10 mg to 80 mg of solifenacin succinate, as Component (a), in admixture with a pharmaceutical carrier in a IR formulation and Layer B, comprising from 4 to 24 mg of ondansetron, as hydrochloride dihydrate, as Component (b), in admixture with a pharmaceutical carrier in an IR-formulation.

A first particularly advantageous solifenacin/ondansetron composition according to this embodiment consist of Layer A, comprising 10 mg of solifenacin succinate, as Component (a), in admixture with a pharmaceutical carrier in a IR formulation and Layer B, comprising 4 mg of ondansetron, as hydrochloride dihydrate, as Component (b), in admixture with a pharmaceutical carrier in an IR-formulation.

A second particularly advantageous solifenacin/ondansetron composition according to this embodiment consist of Layer A, comprising 10 mg of solifenacin succinate, as Component (a), in admixture with a pharmaceutical carrier in a IR formulation and Layer B, comprising 8 mg of ondansetron, as hydrochloride dihydrate, as Component (b), in admixture with a pharmaceutical carrier in an IR-formulation.

An advantageous solifenacin/tropisetron composition according to this embodiment consists of Layer A, comprising from 10 mg to 80 mg of solifenacin succinate, as Component (a), in admixture with a pharmaceutical carrier in a IR formulation and Layer B, comprising from 5 to 15 mg of tropisetron, as hydrochloride, as Component (b), in admixture with a pharmaceutical carrier in an IR-formulation.

A particularly advantageous solifenacin/tropisetron composition according to this embodiment consist of Layer A, comprising 10 mg of solifenacin succinate, as Component (a), in admixture with a pharmaceutical carrier in a IR formulation and Layer B, comprising 5 mg of tropisetron, as hydrochloride, as Component (b), in admixture with a pharmaceutical carrier in an IR-formulation.

An advantageous solifenacin/domperidone composition according to this embodiment consists of Layer A, comprising from 10 mg to 80 mg of solifenacin succinate, as Component (a), in admixture with a pharmaceutical carrier in a IR formulation and Layer B, comprising from 10 to 30 mg of domperidone, as Component (b), in admixture with a pharmaceutical carrier in an IR-formulation.

A particularly advantageous solifenacin/domperidone composition according to this embodiment consist of Layer A, comprising 10 mg of solifenacin succinate, as Component (a), in admixture with a pharmaceutical carrier in a IR formulation and Layer B, comprising 10 mg of domperidone, as Component (b), in admixture with a pharmaceutical carrier in an IR-formulation.

An advantageous solifenacin/metoclopramide composition according to this embodiment consists of Layer A, comprising from 10 mg to 80 mg of solifenacin succinate, as Component (a), in admixture with a pharmaceutical carrier in a IR formulation and Layer B, comprising from 10 to 30 mg of metoclopramide, as monohydrochloride hydrate, as Component (b), in admixture with a pharmaceutical carrier in an IR-formulation.

A particularly advantageous solifenacin/metoclopramide composition according to this embodiment consist of Layer A, comprising 10 mg of solifenacin succinate, as Component (a), in admixture with a pharmaceutical carrier in a IR formulation and Layer B, comprising 10 mg of metoclopramide, as monohydrochloride hydrate, as Component (b), in admixture with a pharmaceutical carrier in an IR-formulation.

Another embodiment of the present invention provides unit forms consisting of tablets comprising from 10 mg to 15 mg, of solifenacin succinate, as Component (a); and from 25 mg to 50 mg preferably from 37.5 mg to 50 mg, of donepezil hydrochloride;

as Component (b), in admixture with a pharmaceutical carrier in a IR-formulation for oral administration.

The above combined pharmaceutical compositions are able to assure greater and longer efficacy and less adverse effects of co-administered AChEIs by allowing the safe and tolerable administration of larger and thus more therapeutically effective quantities (from 2.5 to 7 times the maximum recommended doses) of said AChEIs in human subjects treated with said AChEI. In particular, by inducing very high blood levels in human subjects, the above combined compositions assure an increased concentration of AChEIs to the CNS of patients suffering from a dementia of Alzheimer type which are treated even with very high doses of AChEI.

In particular, the compositions of the present invention are safe and effective, for the treatment of patients in need of an AChEI, in particular of patients suffering from dementias of the Alzheimer type, concurrently or sequentially treated with an AChEI, on a once daily basis.

The pathologic conditions treated with the composition of the present invention include, but are not limited to, Alzheimer's disease, Parkinson's disease dementia, and other chronic disorders of human cognitive and neurobehavioral function that are treated, in part, by pharmaceuticals intended to augment brain acetylcholine-mediated neurotransmission.

The therapeutic efficacy is measured by the degree to which cognitive and other neurobehavioral disabilities associated with dementias of the Alzheimer type, as documented by the use of standard scales, are reduced.

Thus, the present invention also provides a method for inducing neuroprotection, thus combating neurodegeneration, and consequently slowing disease progression in a patient suffering from a dementia of the Alzheimer type, which comprises administering to said patient an AChEI daily dose which is at least 2.5, up to 7 times the maximum recommended daily dose of said AChEI used in the treatment of Alzheimer type dementias, in combination with a pharmaceutical composition comprising an nsPAChA selected from the group consisting of (1S)-(3R)-1-azabicyclo[2.2.2]oct-3-yl 3,4-dihydro-1-phenyl-2(1H)-isoquinolinecarboxylate and pharmaceutically acceptable salts and compounds thereof, in an amount which is equivalent to from 10 mg to 80 mg, advantageously from 11 mg to 80 mg, preferably from 21 mg to 80 mg, of solifenacin succinate; and (b) a non-anticholinergic antiemetic agent (naAEA); in admixture with a pharmaceutical carrier. Said pharmaceutical composition is exhaustively illustrated herein above.

EXAMPLES

The following examples illustrate various aspects of the invention.
Synthesis of a propiverinium alkyl halide
Propiverine hydrochloride (50 mg, 0.12 mM) is suspended in water (10 ml). 2M aqueous sodium carbonate (0.5 ml, 1.0 mM) is added and the reaction mixture is extracted twice with ethyl acetate. The organic phase is dried over anhydrous sodium sulfate and concentrated under reduce pressure. The residue is dissolved in dry ethanol (5 ml) and the ethanolic solution is cooled to 0° C. Methyl iodide (25 ml, 0.40 mM) is then added and the reaction mixture is stirred at room temperature for 18 hours (formation of a white solid). The solid formed is filtered off, washed with small amounts of ethanol and dried under vacuum to afford 1,1-dimethyl-4-[(2,2-diphenyl-2-propoxy)acetoxy]piperidinium iodide (methylpropiverinium iodide) as a white solid (30 mg; yield: 48%). Melting point: 248° C.-250° C. $[C_{24}H_{32}NO_3]^+$ 382.4 (m/z). $^1$H NMR 300 MHz (DMSO $D_6$), d: 0.84 (t, 3H, j=7.5 Hz), 1.50 (qui, 2H, j1=7.5 Hz, j2=6.6 Hz), 1.82 (br.s., 2H), 2.06 (br.s., 2H), 2.91 (br.t., 2H, j=9.3 Hz), 2.94 (s, 3H), 3.02 (s, 3H), 3.14 (t, 2H, j=6.6 Hz), 3.35 (br.s., 2H), 5.00 (m, 1H), 7.37 (m, 10H).

Example 1

Synthesis of a propiverinium alkyl halide
Propiverine hydrochloride (50 mg, 0.12 mM) is suspended in water (10 ml). 2M aqueous sodium carbonate (0.5 ml, 1.0 mM) is added and the reaction mixture is extracted twice with ethyl acetate. The organic phase is dried over anhydrous sodium sulfate and concentrated under reduce pressure. The residue is dissolved in dry ethanol (5 ml) and the obtained solution is cooled to 0° C. Methyl iodide (25 ml, 0.40 mM) is then added and the reaction mixture is stirred at room temperature for 18 hours (formation of a white solid). The solid formed is filtered off, washed with small amounts of ethanol and dried under vacuum to afford 1,1-dimethyl-4-[(2,2-diphenyl-2-propoxy)acetoxy]piperidinium iodide (methylpropiverinium iodide) as a white solid (30 mg; yield: 48%). Melting point: 248° C.-250° C. $[C_{24}H_{32}NO_3]^+$ 382.4 (m/z). $^1$H NMR 300 MHz (DMSO $D_6$), d: 0.84 (t, 3H, j=7.5 Hz). 1.50 (qui, 2H, j1=7.5 Hz, j2=6.6 Hz), 1.82 (br.s., 2H). 2.06 (br.s., 2H). 2.91 (br.t., 2H, j=9.3 Hz), 2.94 (s, 3H), 3.02 (s, 3H), 3.14 (t, 2H, j=6.6 Hz), 3.35 (br.s., 2H), 5.00 (m, 1H), 7.37 (m, 10H).
By operating as described above, by using 0.40 mM of methyl bromide instead of the same amount of methyl iodide, 1,1-dimethyl-4-[(2,2-diphenyl-2-propoxy)acetoxy] piperidinium bromide (methylpropiverinium bromide) is obtained.

Example 2

In one embodiment, the capsules for oral administration are prepared by mixing the following ingredients:

| Ingredients | Parts by weight |
| --- | --- |
| Propiverine hydrochloride | 2,000 |
| Ondansetron hydrochloride dihydrate | 1,000 |
| Lactose USP | 7,500 |
| Colloidal silicon dioxide (Aerosil ®) | 50 |

After mixing, the mixture is screened through a 40 mesh screen and introduced in two-piece hard gelatin capsule No. 3 containing 8 mg of ondansetron (as hydrochloride dihydrate) and 20 mg of propiverine hydrochloride. Similarly, capsules containing 15 mg or 25 mg of propiverine hydrochloride and 8 mg of ondansetron (as hydrochloride dihydrate) are prepared.

In another embodiment, the capsules for oral administration are prepared by mixing the following ingredients:

| Ingredients | Parts by weight |
| --- | --- |
| Donepezil hydrochloride | 5,000 |
| Solifenacin succinate | 2,100 |
| Mannitol | 7,350 |
| Colloidal silicon dioxide (Aerosil ®) | 50 |

After mixing, the mixture is screened through a 40 mesh screen and introduced in two-piece hard gelatin capsule No. 1 containing 50 mg of donepezil hydrochloride and 21 mg of solifenacin succinate. Similarly, capsules containing 25 mg of solifenacin succinate and 50 mg of donepezil hydrochloride are prepared.

In yet another embodiment, the capsules for oral administration are prepared by mixing the following ingredients:

| Ingredients | Parts by weight |
| --- | --- |
| Donepezil hydrochloride | 4,000 |
| Solifenacin succinate | 1,000 |
| Mannitol | 7,350 |
| Colloidal silicon dioxide (Aerosil ®) | 50 |

After mixing, the mixture is screened through a 40 mesh screen and introduced in two-piece hard gelatin capsule No. 2 containing 40 mg of donepezil hydrochloride and 10 mg of solifenacin succinate. Similarly, capsules containing 15 mg or 20 mg of solifenacin succinate and 40 mg of donepezil hydrochloride are prepared.

In yet another embodiment, the capsules for oral administration are prepared by mixing the following ingredients:

| Ingredients | Parts by weight |
| --- | --- |
| Solifenacin succinate | 2,000 |
| Ondansetron hydrochloride dihydrate | 1,000 |
| Lactose USP | 7,350 |
| Colloidal silicon dioxide (Aerosil ®) | 50 |

After mixing, the mixture is screened through a 40 mesh screen and introduced in two-piece hard gelatin capsule No. 3 containing 8 mg of ondansetron (as hydrochloride dihydrate) and 20 mg of solifenacin succinate. Similarly, capsules containing 10 mg or 15 mg of solifenacin succinate and 8 mg of ondansetron (as hydrochloride dihydrate are prepared).

Example 3

According to one embodiment, immediate release tablets for oral administration are prepared by mixing 1.5 kg of propiverine hydrochloride and 5.0 kg of dolasetron mesylate, 0.3 kg of gelatin, 0.3 kg of magnesium stearate and 10 kg of corn starch and forming the mixture into tablets containing 15 mg of propiverine hydrochloride and 50 mg of dolasetron mesylate by a conventional tableting machine. Similarly, tablets containing 17.5 mg or 20 mg of propiverine hydrochloride and 50 mg of dolasetron mesylate are prepared.

According to another embodiment, immediate release tablets for oral administration are prepared by mixing 2.5 kg of solifenacin succinate and 6 kg of donepezil hydrochloride, 0.3 kg of gelatin, 0.3 kg of magnesium stearate and 12 kg of corn starch and forming the mixture into tablets containing 25 mg of solifenacin succinate and 60 mg of donepezil hydrochloride by a conventional tableting machine. Similarly, tablets containing 30 mg of solifenacin succinate and 60 mg of donepezil hydrochloride are prepared.

In yet another embodiment, immediate release tablets for oral administration are prepared by mixing 1.5 kg of solifenacin succinate and 5.0 kg of donepezil hydrochloride, 0.3 kg of gelatin, 0.3 kg of magnesium stearate and 10 kg of corn starch and forming the mixture into tablets containing 15 mg of solifenacin succinate and 50 mg of donepezil hydrochloride by a conventional tableting machine. Similarly, tablets containing 17.5 mg or 20 mg of solifenacin succinate and 40 mg of donepezil hydrochloride are prepared.

In yet another embodiment, immediate release tablets for oral administration are prepared by mixing 1.5 kg of solifenacin succinate and 5.0 kg of dolasetron mesylate, 0.3 kg of gelatin, 0.3 kg of magnesium stearate and 10 kg of corn starch and forming the mixture into tablets containing 15 mg of solifenacin succinate and 50 mg of dolasetron mesylate by a conventional tableting machine. Similarly, tablets containing 17.5 mg or 10 mg of solifenacin succinate and 50 mg of dolasetron mesylate are prepared.

Example 4

Tablets for IR oral administration containing 2 mg of glycopyrronium bromide formulated with a pharmaceutical carrier and tablets containing 10 mg of metoclopramide (as monohydrochloride monohydrate) formulated with a pharmaceutical carrier are distributed in capsules as described in GB 1,254,580, such that unit dosage forms containing 2 mg of glycopyrronium bromide and 10 mg of metoclopramide (as monohydrochloride monohydrate are prepared.

Example 5

Maximum Tolerated Dose and Plasma Levels of Rivastigmine Increase Enabled by Co-Administered Trospium In this single-blind crossover study, healthy volunteers were hospitalized at a Phase I Center (Forenap, Rouffach, France) for the once daily oral administration of ascending doses of rivastigmine hydrogen tartrate ("rivastigmine"), (3 mg to a possible maximum of 24 mg in 3 mg increments as tolerated) together with placebo trospium and then with ascending amounts of rivastigmine (3 mg to a possible maximum of 24 mg as tolerated) together with active trospium. Placebo trospium or active trospium (at a fixed dose of 40 mg per day) were given orally once daily 3 hours before rivastigmine administration. Venous blood was collected for the measurement of plasma drug levels at their nominal peaks (approximately 1 hour after rivastigmine administration). Subjects were monitored clinically for 4 hours after drug administration or until all adverse events had subsided. Safety and tolerability were evaluated based on subject reports, physician observations and examinations, and the performance of standard laboratory tests.

Subject (a) Age 43 years, weight 84 kg. The subject tolerated a dose of 9 mg of rivastigmine when given with placebo trospium and of 24 mg when given with 40 mg of trospium. Adverse events at the rivastigmine dose of 9 mg when given with placebo trospium were limited to mild nausea. Adverse events at the rivastigmine dose of 24 mg when given with 40 mg of trospium also were mild nausea as well as abdominal pain, headache and respiratory difficulty in addition to moderate anorexia. The peak plasma (maximum tolerated) concentration of rivastigmine measured in venous blood collected approximately 1 hour after the administration of 24 mg of rivastigmine together with 40 mg of trospium was 39 ng/ml. Blood samples were not obtained after the 9 mg dose of rivastigmine given with placebo trospium.

Subject (b) Age 26 years, weight 86 kg. The subject tolerated a dose of 15 mg of rivastigmine when given with trospium placebo and of 18 mg given when given with 40 mg of trospium. Adverse events reported at the rivastigmine dose of 15 mg when given with placebo trospium were moderate nausea and mild somnolence. Adverse events at the rivastigmine dose of 18 mg when given with 40 mg of trospium were limited to mild dry mouth. The peak plasma (maximum tolerated) concentration of rivastigmine measured in venous blood collected approximately 1 hour after the administration of 15 mg of rivastigmine given with placebo trospium was 53 ng/ml and after the administration of 18 mg of rivastigmine given with 40 mg of trospium was 94 ng/ml.

Subject (c) Age 31 years, weight 64 kg. The subject tolerated a dose of 15 mg of rivastigmine when given with trospium placebo and of 18 mg when given with 40 of trospium. Adverse events reported at the rivastigmine dose of 15 mg when given with placebo trospium were limited to mild dry mouth. Adverse events reported at the rivastigmine dose of 18 mg when given with 40 mg of trospium were mild dry mouth and moderate urinary difficulty. The peak plasma (maximum tolerated) concentration of rivastigmine measured in venous blood collected approximately 1 hour after the administration of 15 mg of rivastigmine given with placebo trospium was 8.3 ng/ml and after the administration of 18 mg of rivastigmine given with 40 mg of trospium was 131 ng/ml.

Accordingly, when given with 40 mg of trospium, Subject (a) tolerated 4 times the maximum recommended single oral dose of rivastigmine (6 mg) and approximately 5.3 times the reported average maximum tolerated single oral dose of rivastigmine (about 4.5 mg) (Birks J, Grimley Evans J, Iakovidou V, Tsolaki M, Holt F E. Rivastigmine for Alzheimer's disease. Cochrane Database Syst Rev. 2009 Apr. 15; (2): CD001191; Forette F. Anand R. Gharabawi G. *"A phase II study in patients with Alzheimer's disease to assess the preliminary efficacy and maximum tolerated dose of rivastigmine (Exelon)"*. Eur J Neurol. 1999 July; 6(4): 423-9). When given with 40 mg of trospium, Subjects (b) and (c) tolerated 3 times the maximum recommended single dose of rivastigmine and 4 times the average maximum tolerated single oral dose of rivastigmine. Similarly, peak plasma concentrations of rivastigmine in the 3 subjects given their maximum tolerated dose of this drug in combination with 40 mg of trospium averaged 88 ng/ml or 2.9 times the 30.7 ng/ml average measured in 2 of these individuals when rivastigmine was given without trospium and some 7.3 times those reported in the literature (about 12 ng/ml) (New Zealand Data Sheet, EXELON® Rivastigmine 5 and 10 cm² Transdermal Patch. Page 10, FIG. 2, www-.medsafe.govt.nz/profs/datasheet/e/Exelonpatch.pdf) when the maximum recommended single oral dose of rivastigmine (4.5 mg) was administered. The addition of trospium to rivastigmine therapy thus safely enables both an increase in the maximum tolerated dose and in the maximum tolerated plasma concentrations of the acetylcholinesterase inhibitor (AChEI).

Example 6

Tablets for IR oral administration containing 1.12 mg of granisetron hydrochloride formulated with a pharmaceutical carrier and tablets containing 10 mg of solifenacin succinate formulated with a pharmaceutical carrier are distributed in two-compartment capsules as described in GB 1,254,580, such that unit dosage forms containing 1.12 mg of granisetron hydrochloride and 10 mg of solifenacin succinate are prepared.

Similarly, unit dosage forms containing 2.24 mg of granisetron hydrochloride and 10 mg of solifenacin succinate are prepared.

Example 7

Tablets for IR oral administration containing 2 mg of glycopyrronium bromide formulated with a pharmaceutical carrier and tablets containing 10 mg of domperidone formulated with a pharmaceutical carrier are distributed in capsules as described in GB 1,254,580, such that unit dosage forms containing 2 mg of glycopyrronium bromide and 10 mg of domperidone are prepared.

Example 8

Maximum Tolerated Dose and Blood Level of Donepezil Increase Enabled by Co-Administered Solifenacin In this single-blind study, healthy male volunteers were hospitalized at a Phase I Center (MT3D, Rue d' Alsace, 68250 Rouffach, France) for the once daily oral administration of ascending doses of donepezil hydrochloride ("donepezil") per protocol (5 mg to a possible maximum of 40 mg in 5 mg increments as tolerated) together with placebo solifenacin succinate ("solifenacin") and then with ascending amounts of donepezil (5 mg to a possible maximum of 40 mg in 5 mg increments as tolerated) together with active solifenacin. Placebo solifenacin or active solifenacin (at a fixed dose of 10 mg per day) were given orally once daily 2 hours before donepezil administration. Venous blood was collected for the measurement of plasma drug levels at their nominal peaks (approximately 4 hour after donepezil administration). Subjects were carefully monitored following drug administration until all adverse effects had subsided. Safety and tolerability were evaluated based on subject reports, physician observations and examinations, and the performance of standard laboratory tests.

Subject (a) Age 25 years, weight 74 kg. The subject tolerated a dose of 5 mg of donepezil when given with placebo solifenacin and 10 mg of donepezil when given with 10 mg of solifenacin. There were no adverse events at 5 mg of donepezil given with placebo solifenacin. Adverse events at 10 mg of donepezil given with 10 mg of solifenacin were moderate abdominal pain and moderate headache. The peak plasma (maximum tolerated) concentration of donepezil after administration of 5 mg of donepezil with placebo solifenacin was 9.7 ng/ml and after 10 mg of donepezil given with 10 mg of solifenacin was 28.9 ng/ml.

Subject (b), Age 38 years, weight 71 kg. The subject tolerated a dose of 5 mg of donepezil when given with placebo solifenacin and 15 mg of donepezil when given with 10 mg of solifenacin. There were no adverse events at 5 mg of donepezil given with placebo solifenacin. Adverse events at 15 mg of donepezil given with 10 mg of solifenacin were moderate nausea and moderate dizziness. The peak plasma (maximum tolerated) concentration of donepezil after administration of 5 mg of donepezil with placebo solifenacin was 7.1 ng/ml and after 15 mg of donepezil with 10 mg of solifenacin was 36.5 ng/ml.

Subject (c), Age 27 years, weight 74 kgs. The subject tolerated a dose of 5 mg of donepezil when given with placebo solifenacin and 5 mg of donepezil when given with 10 mg of solifenacin. There were no adverse events at 5 mg of donepezil given with placebo solifenacin or given with solifenacin 10 mg. Adverse events with 10 mg of donepezil and placebo solifenacin consisted of severe anorexia, nausea, retching, vomiting, weakness, headache, moderate diarrhea, and mild sweating, dizziness, somnolence, hypersalivation, muscular cramps. Adverse events with 10 mg of donepezil when given with 10 mg of solifenacin consisted of severe nausea and retching. The peak plasma (maximum tolerated) concentration of donepezil after administration of 5 mg of donepezil with placebo solifenacin was 7.8 ng/ml and after 5 mg of donepezil given with 10 mg of solifenacin was 9.31 mg/ml.

Subject (d), Age 25 years, weight 79 kg. The subject tolerated a dose of 15 mg of donepezil when given with placebo solifenacin and 15 mg of donepezil when given with 10 mg of solifenacin. Adverse events with 15 mg of donepezil given with placebo solifenacin consisted of severe abdominal pain, weakness, moderate anorexia, sweating and dry mouth. Adverse events with 15 mg of donepezil given with 10 mg of solifenacin consisted of severe headache. The peak plasma (maximum tolerated) concentration of donepezil after administration of 15 mg of donepezil with placebo solifenacin was 41.7 ng/ml and after 15 mg of donepezil given with 10 mg of solifenacin was 48.9 mg/ml.

Subject (e), Age 29 years, weight 83 kg. The subject tolerated a dose of 30 mg of donepezil when given with placebo solifenacin and 40 mg of donepezil when given with 10 mg of solifenacin. Adverse events at 30 mg of donepezil given with placebo solifenacin were moderate weakness, mild dizziness and moderate hypersalivation. Adverse events at 40 mg of donepezil given with 10 mg of solifenacin were moderate abdominal pain and severe headache. The clinical trial protocol specified that doses higher than 40 mg of donepezil could not be administered. As a consequence, donepezil dose escalation in this subject was discontinued when he reached 40 mg of donepezil+solifenacin, although the subject had not reached maximum tolerated dose. The peak plasma (maximum tolerated) concentration of donepezil after administration of 30 mg of donepezil with placebo solifenacin was 77.5 ng/ml and after 40 mg of donepezil with 10 mg of solifenacin was 140 ng/ml.

Subject (f), Age 28 years, weight 57 kg. The subject tolerated a dose of 5 mg of donepezil when given with placebo solifenacin and 10 mg of donepezil when given with 10 mg of solifenacin. There were no adverse events at 5 mg of donepezil given with placebo solifenacin. Adverse events at 10 mg of donepezil given with 10 mg of solifenacin were limited to moderate dizziness. The peak plasma (maximum tolerated) concentration of donepezil after administration of 5 mg of donepezil with placebo solifenacin was 8.85 ng/ml and after 10 mg of donepezil with 10 mg of solifenacin was 30.5 ng/ml.

As these case reports indicate, in 4 out of 6 subjects, co-treatment with the peripheral anticholinergic, solifenacin, enabled the safe and tolerable administration of substantially higher daily doses of the AChEI, donepezil, than when the cholinesterase inhibitor was given without active solifenacin. Indeed in this controlled study, six healthy volunteers tolerated doses of donepezil combined with solifenacin, that ranged from 5 to (at least) 40 mg and averaged 16 mg or nearly 1.7-fold the maximum recommended dose of this donepezil formulation and nearly 2.2-times its average maximum tolerated dose (about 7.3 mg) in controlled clinical trials (Lockhart I A, Mitchell S A, Kelly S. Safety and tolerability of donepezil, rivastigmine and galantamine for patients with Alzheimer's disease: systematic review of the 'real-world' evidence. Dement Geriatr Cogn Disord. 2009; 28(5):389-403). Adverse events at the first intolerable dose of donepezil given without solifenacin substantially exceeded those at the same donepezil dose when given with the anticholinergic.

In addition, co-administration of the anticholinergic solifenacin, at its maximum recommended dose, permitted the AChEI to safely and tolerably attain peak plasma concentrations averaging 49 ng/ml, in comparison to only 26 ng/ml when maximum tolerated doses of donepezil were given with placebo solifenacin. Peak donepezil levels thus increased some 2.6 fold with combined therapy. The drug dose—plasma level relation (dose proportionality) for both AChEIs are reportedly linear in the relevant dose ranges. Thus the combined use of a peripheral anticholinergic and an AChEI is again shown to safely enable a substantial increase in peak circulating AChEI concentrations in human subjects. Based on previously cited results from multiple animal and human studies, the ability to safely increase the dose and thus exposure to AChEI can be expected to augment their cognitive benefit in patients with Alzheimer's type dementia.

Table 1 below summarizes the MTD and the plasma donepezil concentration of the six above subjects.

TABLE 1

Maximum Tolerated Dose (MTD) and Plasma Concentrations of Donepezil (Donep) Given Alone (MTD-1) or with Solifenacin (Solif) 10 mg/day (MTD-2)

| Subject No. | MTD-1 Donep alone | MTD-2 Donep + Solif | Ratio MTD-2/ MTD-1 | Donep Plasma Concentr. (ng/ml) MTD-1 | MTD-2 | Ratio of Concentr. |
|---|---|---|---|---|---|---|
| (a) | 5 | 10 | 2.0 | 9.7 | 28.9 | 2.98 |
| (b) | 5 | 15 | 3.0 | 7.11 | 36.5 | 5.13 |
| (c) | 5 | 5 | 1.0 | 7.8 | 9.31 | 1.19 |
| (d) | 15 | 15 | 1.0 | 41.7 | 48.9 | 1.17 |
| (e) | 30 | ≥40 | ≥1.4 | 77.5 | >140 | >1.81 |
| (f) | 5 | 10 | 2.0 | 8.85 | 30.5 | 3.45 |

In two subjects, (c) and (d), the MTD of donepezil with or without solifenacin did not change and the donepezil plasma concentrations increased by 20% only after its administration in combination with solifenacin. In the other subjects, after administration of donepezil/solifenacin combination a 33-300% increase of the donepezil MTD induced an 80%-500% increase of the plasma concentration, thus confirming that the AChEI plasma concentrations remarkably increase if the dose of said AChEI increases.

Example 9

(a) Tablets containing 10 mg of solifenacin succinate formulated with a pharmaceutical carrier and tablets containing 10 mg of domperidone formulated with a pharmaceutical carrier distributed in capsules as described in GB 1,254,580, such that unit dosage forms containing 10 mg of solifenacin succinate and 10 mg of domperidone are prepared.

(b) In the same manner, unit dosage forms consisting of capsules each containing one tablet wherein 5 mg of ondansetron hydrochloride dihydrate are formulated with a pharmaceutical carrier and one tablet wherein 10 mg of solifenacin succinate are formulated with a pharmaceutical carrier, are prepared.

(c) Similarly, unit dosage forms consisting of capsules each containing one film-coated tablet wherein 1.12 mg of granisetron hydrochloride are formulated with a pharmaceutical carrier and one tablet wherein 10 mg of solifenacin succinate are formulated with a pharmaceutical carrier, are prepared.

(d) Analogously, unit dosage forms consisting of capsules each containing one tablet wherein 10 mg of metoclopramide, as monohydrochloride monohydrate, are formulated with a pharmaceutical carrier and one tablet wherein 10 mg of solifenacin succinate are formulated with a pharmaceutical carrier, are prepared.

(e) Likewise, unit dosage forms consisting of capsules each containing one film-coated tablet wherein 1.12 mg of granisetron hydrochloride are formulated with a pharmaceutical carrier and one tablet wherein 10 mg of solifenacin succinate are formulated with a pharmaceutical carrier, are prepared.

Example 10

Capsules for oral administration are prepared by mixing the following ingredients:

| Ingredients | Parts by weight |
|---|---|
| Solifenacin succinate | 2,000 |
| Metoclopramide monohydrochloride monohydrate | 1,178 |
| Lactose USP | 7,500 |
| Colloidal silicon dioxide (Aerosil ®) | 50 |

After mixing, the mixture is screened through a 40 mesh screen and introduced in two-piece hard gelatin capsule No. 3 containing 10 mg of metoclopramide (as monohydrochloride monohydrate) and 20 mg of solifenacin succinate.

Similarly, capsules containing 15 mg of solifenacin succinate and 10 mg of metoclopramide (as monohydrochloride monohydrate) are prepared.

Example 11

Tablets for IR oral administration containing 2 mg of glycopyrronium bromide formulated with a pharmaceutical carrier and tablets containing 2 mg of granisetron hydrochloride formulated with a pharmaceutical carrier are distributed in capsules as described in GB 1,254,580, such that unit dosage forms containing 2 mg of glycopyrronium bromide and 2 mg of granisetron hydrochloride.

Example 12

Capsules for oral administration are prepared by mixing the following ingredients:

| Ingredients | Parts by weight |
| --- | --- |
| Trospium chloride | 2,000 |
| Ondansetron hydrochloride dihydrate | 1,000 |
| Lactose USP | 7,500 |
| Colloidal silicon dioxide (Aerosil ®) | 50 |

After mixing, the mixture is screened through a 40 mesh screen and introduced in two-piece hard gelatin capsule No. 3 containing 8 mg of ondansetron (as hydrochloride dihydrate) and 20 mg of trospium chloride.

Similarly, capsules containing 25 mg of trospium chloride and 8 mg of ondansetron (as hydrochloride dihydrate) are prepared.

Example 13

Capsules for oral administration are prepared by mixing the following ingredients:

| Ingredients | Parts by weight |
| --- | --- |
| Trospium chloride | 4,000 |
| Granisetron hydrochloride | 112 |
| Lactose USP | 7,500 |
| Colloidal silicon dioxide (Aerosil ®) | 88 |

After mixing, the mixture is screened through a 40 mesh screen and introduced in two-piece hard gelatin capsule No. 2 containing 40 mg of trospium chloride and 1 mg of granisetron (as hydrochloride).

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A pharmaceutical composition comprising (a) a non-selective, peripheral anticholinergic agent (nsPAChA) selected from the group consisting of propiverine and pharmaceutically acceptable salts thereof, in an amount which is equivalent to from 15 mg to 240 mg of propiverine hydrochloride; trospium and pharmaceutically acceptable salts thereof, in an amount which is equivalent to from 20 mg to 480 mg of trospium chloride; and glycopyrrolium and pharmaceutically acceptable salts thereof, in an amount which is equivalent to from 2 mg to 16 mg of glycopyrronium bromide; and (b) a non-anticholinergic antiemetic agent (naAEA) selected from the group consisting of a $5HT_3$-antagonist, a dopamine receptor (DA)-antagonist, a histamine receptor $H_1$-antagonist, and aprepitant as a substance P receptor antagonist.

2. The pharmaceutical composition according to claim 1, further comprising an acetylcholine esterase inhibitor (AChEI).

3. The pharmaceutical composition according to claim 2, wherein the AChEI at a dose level from 2.5 to 7 times the maximal recommended dose of said AChEI for treatment of Alzheimer type dementia.

4. The pharmaceutical composition according to claim 1, further comprising a pharmaceutical carrier.

5. The pharmaceutical composition according to claim 1, wherein said nsPAChA is propiverine hydrochloride, in an amount of from 31 mg to 240 mg.

6. The pharmaceutical composition according to claim 1, wherein said nsPAChA is trospium chloride, in an amount of from 61 mg to 480 mg.

7. The pharmaceutical composition according to claim 1, wherein said nsPAChA is glycopyrrolium bromide, in an amount of from 4.1 mg to 16 mg.

8. The pharmaceutical composition according to claim 1,
wherein said naAEA is selected from the group consisting of a $5HT_3$-antagonist, a dopamine receptor (DA)-antagonist, and aprepitant as a substance P receptor antagonist;
wherein said $5HT_3$-antagonist is selected from the group consisting of alosetron and pharmaceutically acceptable salts and solvates thereof, in an amount of from 0.5 mg to 3 mg; dolasetron and pharmaceutically acceptable salts thereof, in an amount of from 50 mg to 300 mg; granisetron and pharmaceutically acceptable salts thereof, in an amount of from 1 mg to 3 mg; ondansetron and pharmaceutically acceptable salts and solvates thereof, in an amount of from 4 mg to 24 mg; tropisetron and pharmaceutically acceptable salts thereof, in an amount of from 5 mg to 15 mg;
wherein said dopamine receptor (DA)-antagonist is selected from the group consisting of domperidone and pharmaceutically acceptable salts and solvates thereof, in an amount of from 10 mg to 30 mg; metoclopramide and pharmaceutically acceptable salts and solvates thereof, in an amount of from 10 mg to 30 mg; bromopride and pharmaceutically acceptable salts and solvates thereof, in an amount of from 10 mg to 30 mg; and clebopride and pharmaceutically acceptable salts thereof, in an amount of from 0.5 mg to 1.5 mg; and
wherein said aprepitant is in an amount of from 40 mg to 375 mg.

9. The pharmaceutical composition according to claim 1, wherein said naAEA is selected from the group consisting of a $5HT_3$-antagonist and a dopamine receptor (DA)-antagonist;

wherein said 5HT₃-antagonist is selected from the group consisting of alosetron and pharmaceutically acceptable salts and solvates thereof in an amount of from 0.5 mg to 3 mg; dolasetron and pharmaceutically acceptable salts and solvates thereof in an amount of from 50 mg to 300 mg; granisetron and pharmaceutically acceptable salts and solvates thereof in an amount of from 1 mg to 3 mg; ondansetron and pharmaceutically acceptable salts and solvates thereof in an amount from 4 mg to 24 mg; and tropisetron and pharmaceutically acceptable salts and solvates thereof in an amount of from 5 mg to 15 mg; and wherein said dopamine receptor (DA)-antagonist is selected from the group consisting of domperidone and pharmaceutically acceptable salts and solvates thereof, in an amount of from 10 mg to 30 mg; and metoclopramide and pharmaceutically acceptable salts and solvates thereof, in an amount of from 10 mg to 30 mg.

10. The pharmaceutical composition according to claim 1, wherein said naAEA is selected from the group consisting of a 5HT₃-antagonist and a dopamine receptor (DA)-antagonist;

wherein said 5HT₃-antagonist is selected from the group consisting of alosetron and pharmaceutically acceptable salts and solvates thereof, in an amount of from 0.5 mg to 3 mg; granisetron and pharmaceutically acceptable salts and solvates thereof in an amount of from 1 mg to 3 mg; ondansetron and pharmaceutically acceptable salts and solvates thereof, in an amount of from 4 mg to 24 mg; and tropisetron and pharmaceutically acceptable salts thereof, in an amount f from 5 mg to 15 mg;

wherein said dopamine receptor (DA)-antagonist is selected from the group consisting of domperidone and pharmaceutically acceptable salts and solvates thereof, in an amount of from 10 mg to 30 mg; and metoclopramide and pharmaceutically acceptable salts and solvates thereof, in an amount of from 10 mg to 30 mg.

11. A pharmaceutical composition comprising (a) a non-selective, peripheral anticholinergic agent (nsPAChA) selected from the group consisting of propiverine and pharmaceutically acceptable salts thereof, in an amount which is equivalent to from 15 mg to 120 mg of propiverine hydrochloride; trospium pharmaceutically acceptable salts, in an amount which is equivalent to from 20 mg to 480 mg of trospium chloride; and glycopyrrolium pharmaceutically acceptable salts, in an amount which is equivalent to from 2 mg to 16 mg of glycopyrronium bromide; and (b) a non-anticholinergic antiemetic agent (naAEA) selected from the group consisting of alosetron and pharmaceutically acceptable salts and solvates thereof, in an amount of from 0.5 mg to 3 mg; granisetron and pharmaceutically acceptable salts and solvates thereof in an amount of from 1 mg to 3 mg; ondansetron and pharmaceutically acceptable salts and solvates thereof, in an amount of from 4 mg to 24 mg; tropisetron and pharmaceutically acceptable salts thereof, in an amount of from 5 mg to 15 mg; domperidone and pharmaceutically acceptable salts and solvates thereof, in an amount of from 10 mg to 30 mg; and metoclopramide and pharmaceutically acceptable salts and solvates thereof, in an amount of from 10 mg to 30 mg.

* * * * *